(12) United States Patent
Berger et al.

(10) Patent No.: US 11,814,369 B2
(45) Date of Patent: *Nov. 14, 2023

(54) HIGH RELAXIVITY GADOLINIUM CHELATE COMPOUNDS FOR USE IN MAGNETIC RESONANCE IMAGING

(71) Applicant: BAYER PHARMA AKTIENGESELLSCHAFT, Berlin (DE)

(72) Inventors: Markus Berger, Berlin (DE); Jessica Lohrke, Berlin (DE); Christoph-Stephan Hilger, Berlin (DE); Gregor Jost, Berlin (DE); Thomas Frenzel, Berlin (DE); Olaf Panknin, Berlin (DE); Hubertus Pietsch, Kleinmachnow (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 379 days.

This patent is subject to a terminal disclaimer.

(21) Appl. No.: 17/218,907

(22) Filed: Mar. 31, 2021

(65) Prior Publication Data

US 2021/0221798 A1    Jul. 22, 2021

Related U.S. Application Data

(63) Continuation of application No. 16/463,076, filed as application No. PCT/EP2017/080306 on Nov. 24, 2017, now Pat. No. 10,975,060.

(30) Foreign Application Priority Data

Nov. 28, 2016 (EP) .................... 16200932

(51) Int. Cl.
*C07D 403/14* (2006.01)
*A61K 49/10* (2006.01)
*C07D 257/02* (2006.01)

(52) U.S. Cl.
CPC .......... *C07D 403/14* (2013.01); *A61K 49/106* (2013.01); *C07D 257/02* (2013.01)

(58) Field of Classification Search
CPC .. A61K 49/106; A61K 49/108; C07D 257/02; C07D 403/14
See application file for complete search history.

(56) References Cited

U.S. PATENT DOCUMENTS

| | | | |
|---|---|---|---|
| 4,485,237 A | 11/1984 | Willer | |
| 4,647,447 A | 3/1987 | Gries et al. | |
| 5,011,925 A | 4/1991 | Rajagopalan et al. | |
| 5,039,512 A | 8/1991 | Kraft et al. | |
| 5,141,740 A | 8/1992 | Rajagopalan et al. | |
| 5,281,704 A | 1/1994 | Love et al. | |
| 5,284,647 A | 2/1994 | Niedballa et al. | |
| 5,403,572 A | 4/1995 | Gries et al. | |
| 5,560,903 A | 10/1996 | Gries et al. | |
| 5,650,133 A | 7/1997 | Carvalho et al. | |
| 5,679,810 A | 10/1997 | Love et al. | |
| 5,863,518 A | 1/1999 | Hashiguchi et al. | |
| 5,866,562 A | 2/1999 | Schohe-Loop et al. | |
| 5,876,695 A | 3/1999 | Gries et al. | |
| 5,919,433 A | 7/1999 | Platzek et al. | |
| 6,019,959 A | 2/2000 | Platzek et al. | |
| 6,045,776 A | 4/2000 | Platzek et al. | |
| 6,056,939 A | 5/2000 | Desreux et al. | |
| 6,248,306 B1 | 6/2001 | Schmitt-Willich et al. | |
| 6,440,956 B1 | 8/2002 | Port | |
| 6,447,749 B1 | 9/2002 | Licha et al. | |
| 6,511,649 B1 | 1/2003 | Harris et al. | |
| 6,537,520 B1 | 3/2003 | Rajopadhye et al. | |
| 6,693,190 B1 | 2/2004 | Ranganathan et al. | |
| 7,294,615 B1 | 11/2007 | Bovin et al. | |
| 8,545,813 B2 | 10/2013 | Song et al. | |
| 11,021,451 B2 | 6/2021 | Lattuada et al. | |
| 11,110,185 B2 | 9/2021 | Meijer et al. | |
| 2002/0052354 A1 | 5/2002 | Platzek et al. | |
| 2002/0077456 A1 | 6/2002 | Takano et al. | |
| 2003/0004236 A1 | 1/2003 | Meade | |
| 2003/0171561 A1 | 9/2003 | Pillai et al. | |
| 2004/0170566 A1 | 9/2004 | Chang et al. | |
| 2006/0093554 A1 | 5/2006 | Platzek et al. | |
| 2006/0104908 A1 | 5/2006 | Grimmond et al. | |
| 2007/0202047 A1 | 8/2007 | Wolf et al. | |
| 2009/0196829 A1 | 8/2009 | Song et al. | |
| 2011/0081428 A1 | 4/2011 | Lithgow et al. | |

(Continued)

FOREIGN PATENT DOCUMENTS

CA    2274132 A1    6/1998
CN    102442996 A   5/2012

(Continued)

OTHER PUBLICATIONS

Morcos; S.K., "Extracellular gadolinium contrast agents: Differences in stability", European Journal of Radiology, May 2008, vol. 66/Issue 2, 175-179.

(Continued)

*Primary Examiner* — Michael G. Hartley
*Assistant Examiner* — Jagadishwar R Samala
(74) *Attorney, Agent, or Firm* — Joseph L. Kent; James R. Stevenson; David Schramm

(57) ABSTRACT

The present invention relates to a new class of high relaxivity extracellular gadolinium chelate complexes, to methods of preparing said compounds, and to the use of said compounds as MRI contrast agents.

11 Claims, 4 Drawing Sheets

(56) References Cited

U.S. PATENT DOCUMENTS

| | | |
|---|---|---|
| 2012/0244070 A1 | 9/2012 | Lu et al. |
| 2013/0302258 A1 | 11/2013 | Meade et al. |
| 2014/0363376 A1 | 12/2014 | Sun et al. |
| 2016/0101196 A1 | 4/2016 | Medina et al. |
| 2017/0293009 A1 | 10/2017 | Meade et al. |
| 2020/0017453 A1 | 1/2020 | Boi et al. |

FOREIGN PATENT DOCUMENTS

| | | |
|---|---|---|
| CN | 102614531 A | 8/2012 |
| CN | 102973955 A | 3/2013 |
| CN | 103554185 A | 2/2014 |
| CN | 103611171 A | 3/2014 |
| DE | 19525924 A1 | 1/1997 |
| DE | 19652386 A1 | 6/1998 |
| DE | 19652387 A1 | 6/1998 |
| DE | 102007058220 A1 | 6/2009 |
| DE | 102009053171 A1 | 5/2011 |
| EP | 0255471 A1 | 2/1988 |
| EP | 0305320 A2 | 3/1989 |
| EP | 0438206 A1 | 7/1991 |
| EP | 0454078 A2 | 10/1991 |
| EP | 0946525 A1 | 10/1999 |
| EP | 0946526 A1 | 10/1999 |
| EP | 1931673 A1 | 6/2008 |
| EP | 2457594 A1 | 5/2012 |
| EP | 2457914 A1 | 5/2012 |
| EP | 3101012 A1 | 12/2016 |
| EP | 3551614 B1 | 8/2021 |
| JP | 2008012596 A | 1/2008 |
| KR | 20130080245 A | 7/2013 |
| KR | 20140021742 A | 2/2014 |
| KR | 20140021743 A | 2/2014 |
| WO | 9002652 A1 | 3/1990 |
| WO | 9103200 A1 | 3/1991 |
| WO | 9105762 A1 | 5/1991 |
| WO | 9209527 A1 | 6/1992 |
| WO | 9209884 A1 | 6/1992 |
| WO | 9218536 A2 | 10/1992 |
| WO | 9221017 A1 | 11/1992 |
| WO | 9311120 A1 | 6/1993 |
| WO | 9311800 A1 | 6/1993 |
| WO | 9316375 A1 | 8/1993 |
| WO | 9407894 A1 | 4/1994 |
| WO | 9427644 A1 | 12/1994 |
| WO | 9501966 A1 | 1/1995 |
| WO | 9509848 A2 | 4/1995 |
| WO | 9520353 A1 | 8/1995 |
| WO | 9531444 A1 | 11/1995 |
| WO | 9601655 A1 | 1/1996 |
| WO | 9616677 A2 | 6/1996 |
| WO | 9638184 A2 | 12/1996 |
| WO | 9702051 A2 | 1/1997 |
| WO | 9718231 A1 | 5/1997 |
| WO | 9723245 A1 | 7/1997 |
| WO | 9726017 A2 | 7/1997 |
| WO | 9730969 A1 | 8/1997 |
| WO | 9732862 A1 | 9/1997 |
| WO | 9824775 A1 | 6/1998 |
| WO | 9901161 A1 | 1/1999 |
| WO | 9916757 A1 | 4/1999 |
| WO | 9921592 A1 | 5/1999 |
| WO | 0001698 A1 | 1/2000 |
| WO | 0009169 A1 | 2/2000 |
| WO | 0076616 A1 | 12/2000 |
| WO | 0076760 A1 | 12/2000 |
| WO | 0151095 A2 | 7/2001 |
| WO | 0152906 A2 | 7/2001 |
| WO | 0164708 A1 | 9/2001 |
| WO | 0197848 A2 | 12/2001 |
| WO | 0197860 A2 | 12/2001 |
| WO | 0213874 A2 | 2/2002 |
| WO | 0213875 A2 | 2/2002 |
| WO | 0214309 A1 | 2/2002 |
| WO | 02051854 A1 | 7/2002 |
| WO | 03009874 A1 | 2/2003 |
| WO | 03011115 A2 | 2/2003 |
| WO | 03013617 A2 | 2/2003 |
| WO | 03014157 A2 | 2/2003 |
| WO | 03074523 A2 | 9/2003 |
| WO | 03088823 A2 | 10/2003 |
| WO | 2004006965 A2 | 1/2004 |
| WO | 2004006979 A2 | 1/2004 |
| WO | 2004065407 A2 | 8/2004 |
| WO | 2004074267 A1 | 9/2004 |
| WO | 2005001415 A2 | 1/2005 |
| WO | 2005007200 A1 | 1/2005 |
| WO | 2005108379 A1 | 11/2005 |
| WO | 2005115997 A1 | 12/2005 |
| WO | 2006002873 A2 | 1/2006 |
| WO | 2006002874 A1 | 1/2006 |
| WO | 2006014530 A2 | 2/2006 |
| WO | 2006029560 A1 | 3/2006 |
| WO | 2006080022 A2 | 8/2006 |
| WO | 2006136460 A2 | 12/2006 |
| WO | 2007042506 A1 | 4/2007 |
| WO | 2007064226 A2 | 6/2007 |
| WO | 2007064227 A1 | 6/2007 |
| WO | 2007069909 A2 | 6/2007 |
| WO | 2007084264 A2 | 7/2007 |
| WO | 2007088129 A2 | 8/2007 |
| WO | 2007100563 A2 | 9/2007 |
| WO | 2007111514 A1 | 10/2007 |
| WO | 2007111515 A2 | 10/2007 |
| WO | 2007112100 A2 | 10/2007 |
| WO | 2007128567 A1 | 11/2007 |
| WO | 2007128873 A1 | 11/2007 |
| WO | 2008017122 A1 | 2/2008 |
| WO | 2008022263 A2 | 2/2008 |
| WO | 2008087017 A2 | 7/2008 |
| WO | 2008125594 A1 | 10/2008 |
| WO | 2009013350 A2 | 1/2009 |
| WO | 2009018332 A1 | 2/2009 |
| WO | 2009027388 A2 | 3/2009 |
| WO | 2009030735 A1 | 3/2009 |
| WO | 2009047245 A1 | 4/2009 |
| WO | 2009077575 A1 | 6/2009 |
| WO | 2009080739 A1 | 7/2009 |
| WO | 2009093082 A1 | 7/2009 |
| WO | 2009098191 A2 | 8/2009 |
| WO | 2009098192 A1 | 8/2009 |
| WO | 2009103744 A2 | 8/2009 |
| WO | 2009127715 A1 | 10/2009 |
| WO | 2009143101 A2 | 11/2009 |
| WO | 2010006755 A2 | 1/2010 |
| WO | 2010039609 A2 | 4/2010 |
| WO | 2010056590 A2 | 5/2010 |
| WO | 2010066815 A2 | 6/2010 |
| WO | 2010108125 A2 | 9/2010 |
| WO | 2010147666 A1 | 12/2010 |
| WO | 2011031740 A1 | 3/2011 |
| WO | 2011073371 A1 | 6/2011 |
| WO | 2011088193 A2 | 7/2011 |
| WO | 2011124672 A1 | 10/2011 |
| WO | 2011158189 A1 | 12/2011 |
| WO | 2012059576 A1 | 5/2012 |
| WO | 2012142702 A1 | 10/2012 |
| WO | 2012143355 A1 | 10/2012 |
| WO | 2013022797 A1 | 2/2013 |
| WO | 2013087965 A1 | 6/2013 |
| WO | 2014052471 A1 | 4/2014 |
| WO | 2014075079 A1 | 5/2014 |
| WO | 2014110372 A1 | 7/2014 |
| WO | 2014124943 A1 | 8/2014 |
| WO | 2014197763 A1 | 12/2014 |
| WO | 2015071856 A1 | 5/2015 |
| WO | 2015071857 A1 | 5/2015 |
| WO | 2015171792 A1 | 11/2015 |
| WO | 2016050210 A1 | 4/2016 |
| WO | 2016149363 A1 | 9/2016 |
| WO | 2016193190 A1 | 12/2016 |
| WO | 2017004220 A1 | 1/2017 |
| WO | 2017030728 A1 | 2/2017 |
| WO | 2017098038 A1 | 6/2017 |

(56) References Cited

FOREIGN PATENT DOCUMENTS

| | | |
|---|---|---|
| WO | 2017098044 A1 | 6/2017 |
| WO | 2017178301 A1 | 10/2017 |
| WO | 2018096082 A1 | 5/2018 |
| WO | 2018108780 A1 | 6/2018 |

OTHER PUBLICATIONS

Aime S., et al., "Biodistribution of Gadolinium-Based Contrast Agents, Including Gadolinium Deposition," Journal of Magnetic Resonance Imaging, Dec. 2009, vol. 30 (6), pp. 1259-1267.
Becker S., et al., "Application of Gadolinium-Based Contrast Agents and Prevalence of Nephrogenic Systemic Fibrosis in a Cohort of End-Stage Renal Disease Patients on Hemodialysis," Nephron Clinical Practice, Nov. 2012, vol. 121 (1-2), pp. C91-C94.
Berge S.M., et al., "Pharmaceutical Salts," Journal of Pharmaceutical Sciences, Jan. 1977, vol. 66 (1), pp. 1-19.
Caravan P., "Strategies for Increasing the Sensitivity of Gadolinium Based Mri Contrast Agents," Chemical Society Reviews, Jun. 2006, vol. 35 (6), pp. 512-523.
Chen Liu Qi; et al., "Evaluating pH in the Extracellular Tumor Microenvironment Using CEST MRI and Other Imaging Methods", Adv. Radiol., 2015, 1-39.
Cross L.C., et al., "IUPAC Commission on Nomenclature of Organic Chemistry, Rules for Nomenclature of Organic Chemistry Section E: Stereochemistry, ," Pure and Applied Chemistry, 1976, vol. 45, pp. 11-30.
Di Gregorio E., et al., "Gd Loading by Hypotonic Swelling: an Efficient and Safe Route for Cellular Labeling," Contrast Media & Molecular Imaging, Nov.-Dec. 2013, vol. 8 (6), pp. 475-486.
Frenzel T., et al., "Stability of Gadolinium-Based Magnetic Resonance Imaging Contrast Agents in Human Serum at 37° C.," Investigative Radiology, Dec. 2008, vol. 43 (12), pp. 817-828.
Giesel F.L., et al., "High-relaxivity Contrast-enhanced Magnetic Resonance Neuroimaging: a Review," European Radiology, Oct. 2010, vol. 20 (10), pp. 2461-2474.
Greene; And Wuts., "Chapter 7: Protection for the Amino Group", Protective Groups in Organic Synthesis, John Wiley & Sons, Inc., 1999, Third Edition, 494-653.
Helm L., "Optimization of Gadolinium-based MRI Contrast Agents for High Magnetic-field Applications," Future Medicinal Chemistry, Mar. 2010, vol. 2 (3), pp. 385-396.
Hermann P., et al., "Gadolinium(III) Complexes as MRI Contrast Agents: Ligand Design and Properties of the Complexes," Dalton Transactions, Jun. 2008, pp. 3027-3047.
"International Search Report and Written Opinion from PCT Application No. PCT/EP2017/080306", dated Mar. 6, 2018.
Jacques V., et al., "High-relaxivity Magnetic Resonance Imaging Contrast Agents. Part 2. Optimization of Inner- and Second-sphere Relaxivity," Investigative Radiology, Oct. 2010, vol. 45 (10), pp. 613-624.
Jagadish B.; et al., "On the synthesis of 1,4,7-tris(tert-butoxycarbonylmethyl)-1,4,7,10-tetraazacyclododecane", Tetrahedron Letters, 2011, 52, 2058-2061.
Jebasingh B., et al., "Synthesis and Relaxivity Studies of a Tetranuclear Gadolinium(III) Complex of DO3A as a Contrast-Enhancing Agent for MRI," Inorganic Chemistry, Nov. 2005, vol. 44 (25), pp. 9434-9443.
Merbach; Andre et al, "The Chemistry of Contrast Agents in Medical Magnetic Resonance Imaging, 2nd Edition", John Wiley & Sons Ltd., 2013, 31-32, 194.
Montalbetti C.A., et al., "Amide Bond Formation and Peptide Coupling," Tetrahedron, 2005, vol. 61, pp. 10827-10852.
Ranganathan R.S., et al., "New Multimeric Magnetic Resonance Imaging Agents," Investigative Radiology, Nov. 1998, vol. 33 (11), pp. 779-797.
Rohrer M., et al., "Comparison of Magnetic Properties of MRI Contrast Media Solutions at Different Magnetic Field Strengths," Investigative Radiology, Nov. 2005, vol. 40 (11), pp. 715-724.

Roy O. et al., "The tert-Butyl Side Chain: A Powerful Means to Lock Peptoid Amide Bonds in the Cis Conformation", Organic Letters, 2013, vol. 15, No. 9, 2246-2249.
Sherry A. Dean; et al., "Chemical Exchange Saturation Transfer Contrast Agents For Magnetic Resonance Imaging", Annu Rev Biomed Eng , 2008,10, 391-411.
Suh John T.; et al., "Angiotensin-Convertin Enzyme Inhibitors. New Orally Active Antihypertensive Mercaptoalkanoyl)- and [(Acylthio)alkanoyl]glycine Derivatives", Journal of Medicinal Chemistry, 1985, vol. 28, No. 1, 57-66.
Toth E.; et al., "Chapter 2: Relaxivity of Gadolinium(III) Complexes: Theory and Mechanism", The Chemistry of Contrast Agents in Medical Magnetic Resonance Imaging, John Wiley & Sons, Ltd , 2013, Second Edition, 25-81.
Wang Y., et al., "Incidence of Nephrogenic Systemic Fibrosis After Adoption of Restrictive Gadolinium-based Contrast Agent Guidelines," Radiology, Jul. 2011, vol. 260 (1), pp. 105-111.
Xiao; Yu-Dong et al., "MRI contrast agents: Classification and application (Review)", International Journal of Molecular Medicine, 2016, 38, 1319-1326.
Yang L., et al., "Nephrogenic Systemic Fibrosis and Class Labeling of Gadolinium-based Contrast Agents by the Food and Drug Administration," Radiology, Oct. 2012, vol. 265 (1), pp. 248-253.
Zhang W., et al., "A Tetranuclear Gadolinium(III) Macrocyclic Complex: Towards High Relaxivity with the Rigid Linkers for Magnetic Resonance Imaging Contrast Agent," Zeitschrift Fur Anorganische Und Allgemeine Chemie, Mar. 2015, vol. 641 (3-4), pp. 578-585.
Zhao G., et al., "Two Multinuclear GdIII Macrocyclic Complexes as Contrast Agents with High Relaxivity and Stability Using Rigid Linkers," Inorganica Chimica Acta, Sep. 2013, vol. 406, pp. 146-152.
Averin A.D., et al., "Synthesis of a New Family of bi- and Polycyclic Compounds via Pd-catalyzed Amination of 1,7-di (3-bromobenzyl)cyclen," Tetrahedron Letters, Jun. 2008, vol. 49 (24), pp. 3950-3954.
Banerjee S.R., et al., "Synthesis and Evaluation of Gd(III) -Based Magnetic Resonance Contrast Agents for Molecular Imaging of Prostate-Specific Membrane Antigen," Angewandte Chemie, Sep. 2015, vol. 54 (37), pp. 10778-10782.
Bazzicalupi C., et al., "Tren-based Tris-macrocycles as Anion Hosts. Encapsulation of Benzenetricarboxylate Anions within Bowl-shaped Polyammonium Receptors," The Journal of Organic Chemistry, May 2005, vol. 70 (11), pp. 4257-4266.
Bazzicalupi C., et al., "Synthesis of New Tren-based Tris-macrocycles. Anion Cluster Assembling Inside the Cavity Generated by a Bowl-shaped Receptor," The Journal of Organic Chemistry, Dec. 2002, vol. 67 (25), pp. 9107-9110.
Bazzicalupi C., et al., "Zn(II) Coordination to Tren-based Tris-macrocycles. Activity of their Trinuclear Zn(II) Complexes in Carboxy- and Phosphate-ester Hydrolysis," Dalton Transactions, Aug. 2003, pp. 3574-3580.
Bencini A., et al., "A Tris-Macrocycle with Proton Sponge Characteristics as Efficient Receptor for Inorganic Phosphate and Nucleotide Anions," European Journal of Organic Chemistry, Nov. 2009, vol. 2009 (32), pp. 5610-5621.
Bencini A., et al., "Proton and Cu(II) Binding to Tren-based Tris-macrocycles Affinity Towards Nucleic Acids and Nuclease Activity," Dalton Transactions, Feb. 2003, pp. 793-800.
Besenius P., et al., "Controlling the Growth and Shape of Chiral Supramolecular Polymers in Water," Proceedings of the National Academy of Sciences of the United States of America, Oct. 2010, vol. 107 (42), Pp. 17888-17893.
Besenius P., et al., "Peptide Functionalised Discotic Amphiphiles and their Self-assembly into Supramolecular Nanofibres," Soft Matter, 2011, vol. 7, pp. 7980-7983.
Bhuniya S., et al., "Uridine-based Paramagnetic Supramolecular Nanoaggregate with High Relaxivity Capable of Detecting Primitive Liver Tumor Lesions," Biomaterials, Sep. 2011, vol. 32 (27), pp. 6533-6540.
Bhuyan M., et al., "BiomaterialsRigid Luminescent Bis-Zinc(II)-Bis-Cyclen Complexes for the Detection of Phosphate Anions and

(56) References Cited

OTHER PUBLICATIONS

Non-Covalent Protein Labeling in Aqueous Solution," European Journal of Organic Chemistry, May 2011, vol. 2011(15), pp. 2807-2817.

Boldrini V., et al., "Expeditious N-monoalkylation of 1,4,7,10-tetraazacyclododecane (Cyclen) via Formamido Protection," Tetrahedron Letters, Aug. 2000, vol. 41 (33), pp. 6527-6530.

Boros E., et al., "Gd(DOTAla): A Single Amino Acid Gd-complex as a Modular Tool for High Relaxivity MR Contrast Agent Development," Journal of the American Chemical Society, Dec. 2012, vol. 134 (48), pp. 19858-19868.

Bruckner K., et al., "Solid Phase Synthesis of Short Peptide-Based Multimetal Tags for Biomolecule Labeling," Bioconjugate Chemistry, May 2014, vol. 25 (6), pp. 1069-1077.

Bumb et al.;, "Macromolecular and Dendrimer Based Magnetic Resonance Contrast Agents", Acta Radiol., Sep. 2010, vol. 51/Issue 7, 751-767.

Carney C.E., et al., "Cell Labeling via Membrane-Anchored Lipophilic MR Contrast Agents," Bioconjugate Chemistry, May 2014, vol. 25 (5), pp. 945-954.

Carney C.E., et al., "Nanodiscs as a Modular Platform for Multimodal MR-Optical Imaginga," Bioconjugate Chemistry, May 2015, vol. 26 (5), pp. 899-905.

Chang C.A., et al., "Synthesis, Characterization, and Crystal Structures of M(D03A) (M=Fe, Gd) and Na[M(DOTA)] (M=Fe, Y, Gd)," Inorganic Chemistry, Aug. 1993, vol. 32 (16), pp. 3501-3508.

Chen Z., et al., "Fullerenes Cn 36 (n=0, 2+, 2−) and their B- and N-doped Analogues," Chemical Physics Letters, Oct. 2000, vol. 329 (2000), pp. 47-51.

Coderre J.A., et al., "Selective Delivery of Boron by the Melanin Precursor Analogue p-Boronophenylalanine to Tumors Other Than Melanoma," Cancer Research, Jan. 1990, vol. 50, pp. 138-141.

Cui P., et al., "An Ion Pair Scandium Hydride Supported by a Dianionic (NNNN)-type Macrocycle Ligand," Chemical Communications, 2014, vol. 50, pp. 424-426.

Cui P., et al., "Dehydrogenation of Amine-borane Me2NH-BH3 Catalyzed by a Lanthanum-hydride Complex," Chemistry a European Journal, Sep. 2013, vol. 19 (40), pp. 13437-13444.

Cui P., et al., "Heterometallic Potassium Rare-Earth-Metal Allyl and Hydrido Complexes Stabilized by a Dianionic (NNNN)-Type Macrocyclic Ancillary Ligand," Organometallics, 2013, vol. 32 (5), pp. 1176-1182.

Cvrtila I., et al., "Redox Control over Acyl Hydrazone Photoswitches," Journal of the American Chemical Society, Jul. 2017, vol. 139 (36), pp. 12459-12465.

"Decision of the Opposition Division on EP3303307B1", Dec. 20, 2021.

"Declaration by Dr. Markus Berger, Senior Scientist and Dr. Thomas Frenzel, Senior Scientist, Bayer AG", Jul. 2, 2021.

Delepine A., et al., "Selective Mono-n-alkylation of Triethylenetetraamine. A New Versatile Route to Polylinear Azaligands," Tetrahedron Letters, May 2009, vol. 50 (21), pp. 2521-2524.

Delepine A., et al., "From Flexible to Constrained Tris(tetraamine) Ligands: Synthesis, Acid-Base Properties, and Structural Effect on the Coordination Process with Nucleotides," European Journal of Organic Chemistry, Oct. 2010, vol. 2010 (28), pp. 5380-5390.

Eggenspiller A., et al., "Design of Porphyrin-dota-Like Scaffolds as All-in-One Multimodal Heterometallic Complexes for Medical Imaging," European Journal of Organic Chemistry, Oct. 2013, vol. 2013 (29), pp. 6629-6643.

European Search Report for Application No. EP15170658.7, dated Dec. 4, 2015, 6 pages.

Faulkner S., et al., "Lanthanide-Sensitized Lanthanide Luminescence: Terbium-Sensitized Ytterbium Luminescence in A Trinuclear Complex," Journal of the American Chemical Society, Aug. 2003, vol. 125 (35), pp. 10526-10527.

Fischer; Gunter, "Chemical aspects of peptide bond isomerisation", The Royal Society of Chemistry, Chem Soc Rev, 2000, 29, 119-127.

Fisher M.J., et al., "Trivalent Gd-DOTA Reagents for Modification of Proteins," RSC Advances, Dec. 2015, vol. 5 (116), pp. 96194-96200.

Fleischer E.B., et al., "Conversion of Aliphatic and Alicyclic Polyalcohols to the Corresponding Primary Polyamines," The Journal of Organic Chemistry, Oct. 1971, vol. 36 (20), pp. 3042-3044.

Fries Peter; MD, et al, "P03277—A New Approach to Achieve High-Contrast Enhancement", Investigative Radiology, Dec. 2015, vol. 50 No. 12, 835-842.

Galibert M., et al., "RGD-cyclam Conjugate: Synthesis and Potential Application for Positron Emission Tomography," Bioorganic & Medicinal Chemistry Letters, Sep. 2010, vol. 20 (18), pp. 5422-5425.

Ganb A., et al., "Synthesis and Structural Characterization of a Cyclen-Derived Molecular Cage," Organic Letters, Nov. 2015, vol. 17 (23), pp. 5850-5853.

Grauer A., et al., "Synthetic Receptors for the Differentiation of Phosphorylated Peptides with Nanomolar Affinities," Chemistry a European Journal, Oct. 2008, vol. 14 (29), pp. 8922-8927.

Grunberg J., et al., "DOTA-Functionalized Polylysine: A High Number of DOTA Chelates Positively Influences the Biodistribution of Enzymatic Conjugated Anti-Tumor Antibody chCE7agl," PLoS One, 2013, vol. 8 (4), pp. 1-11.

Harrison V.S.R., et al., "A Multimeric MR-optical Contrast Agent for Multimodal Imaging," Chemical Communications, Aug. 2014, vol. 50, pp. 11469-11471.

Harrison V.S.R., et al., "Multimeric Near IR-MR Contrast Agent for Multimodal In Vivo Imaging," Journal of the American Chemical Society, Jul. 2015, vol. 137 (28), pp. 9108-9116.

Hayes W., et al., "One-pot Synthesis of Multivalent Arrays of Mannose Monoand Disaccharides," Tetrahedron, Sep. 2003, vol. 59 (40), pp. 7983-7996.

Hill L.R., et al., "Ternary Self-assemblies in Water: Forming a Pentanuclear ReLn4 Assembly by Association of Binuclear Lanthanide Binding Pockets With Fac-Re(CO)3(Dinicotinate)2cl," Dalton Transactions, Aug. 2013, vol. 42, pp. 16255-16258.

Huang Z., et al., "A Fluorinated Dendrimer-Based Nanotechnology Platform: New Contrast Agents for High Field Imaging," Investigative Radiology, Oct. 2010, vol. 45 (10), pp. 641-654.

"International Preliminary Report on Patentability from PCT Application No. PCT/EP2019/082117", dated May 25, 2021.

International Search Report and Written Opinion for Application No. PCT/EP2016/062105, dated Jul. 13, 2016, 10 pages.

Iwaki S., et al., "A Design Strategy for Small Molecule-based Targeted MRI Contrast Agents: Their Application for Detection of Atherosclerotic Plaques," Organic & Biomolecular Chemistry, Nov. 2014, vol. 12 (43), pp. 8611-8618.

Jacques V., et al., Synthesis of MRI Contrast Agents IL Macrocyclic Ligands, Table of Contents.

Kimura E., et al., "A Tris(ZnII-1,4,7,10-tetraazacyclododecane) Complex as a New Receptor for Phosphate Dianions in Aqueous Solution," Journal of the American Chemical Society, Apr. 1997, vol. 119 (13), pp. 3068-3076.

Kimura E., et al., "Selective and Efficient Recognition of Thymidylylthymidine (TpT) by Bis(ZnII-cyclen) and Thymidylylthymidylylthymidine (TpTpT) by Tris(ZnII-cyclen) at Neutral pH in Aqueous Solution," Chemistry a European Journal, Nov. 1999, vol. 5 (11), pp. 3113-3123.

Rompp; Kompakt., "Basislexikon Chemie", 1999, 2436.

Scarso A., et al., "Tripodal, Cooperative, and Allosteric Transphosphorylation Metallocatalysts," The Journal of Organic Chemistry, Jan. 2007, vol. 72 (2), pp. 376-385.

Schmidek H.H., et al., "Morphological Studies of Rat Brain Tumors Induced by N-nitrosomethylurea," Mar. 1971, vol. 34 (3), pp. 335-340.

Schuhle D.T., et al., "Calix[4]arenes as Molecular Platforms for Magnetic Resonance Imaging (MRI) Contrast Agents," Chemistry a European Journal, 2009, vol. 15 (13), pp. 3290-3296.

Schuhle D.T., et al., "Densely Packed Gd(III)-chelates with Fast Water Exchange on a Calix[4]arene Scaffold: a Potential MRI Contrast Agent," Dalton Transactions, Jan. 2010, vol. 39, pp. 185-191.

(56) References Cited

OTHER PUBLICATIONS

Schuhle D.T., et al., "Liposomes with Conjugates of a Calix[4]arene and a Gd-DOTA Derivative on the Outside Surface; an Efficient Potential Contrast Agent for MRI," Chemical Communications, 2010, vol. 46, pp. 4399-4401.
Schurink H.B., "Pentaerythrityl Bromide and Iodide," Organic Syntheses, 1937, vol. 17, p. 73.
Siegfried L., et al., "Homo- and Heteropolynuclear Ni2+ and Cu2+ Complexes of Polytopic Ligands, Consisting of a Tren Unit Substituted with Three 12-membered Tetraazamacrocycles," Dalton Transactions, Nov. 2007, pp. 4797-4810.
Song Y., et al., "Synthesis of Multimeric MR Contrast Agents for Cellular Imaging," Journal of the American Chemical Society, May 2008, vol. 130 (21), pp. 6662-6663.
Sorensen T.J., et al., "Preparation and Study of an f,f,f′,f″ Covalently Linked Tetranuclear Hetero-trimetallic Complex—a Europium, Terbium, Dysprosium Triad," Chemical Communications, 2013, vol. 49 (8), pp. 783-785.
Sorensen T.J., et al., "Triheterometallic Lanthanide Complexes Prepared from Kinetically Inert Lanthanide Building Blocks," European Journal of Inorganic Chemistry, Apr. 2017, vol. 2017 (15), pp. 2165-2172.
Suchy; et al., "A paramagnetic chemical exchange-based MRI probe metabolized by cathepsin D: design, synthesis and cellular uptake studies", Organic Biomolecular Chemistry, Mar. 26, 2010, vol. 8, 2560-2566.
Sung S., et al., "Multimetallic Complexes and Functionalized Gold Nanoparticles Based on a Combination of d- and f-Elements," Inorganic Chemistry, Feb. 2014, vol. 53 (4), pp. 1989-2005.
Sy M., et al., "Spectroscopic Properties of a Family of Mono- to Trinuclear Lanthanide Complexes," European Journal of Inorganic Chemistry, Apr. 2017, vol. 2017 (14), pp. 2122-2129.
Takemura H., et al., "Synthesis and Inclusion Properties of Pyridinophane-linked Macrocycles," Journal of the Chemical Society, Perkin Transactions 1, Jan. 1996, pp. 277-280.
Tamain C., et al., "Coordination of Tetravalent Actinides (An=ThIV, UIV, NpIV, PuIV) with DOTA: from Dimers to Hexamers," Chemistry a European Journal, May 2017, vol. 23 (28), pp. 6864-6875.
Tamain C., et al., "First Evidence of a Water-Soluble Plutonium(IV) Hexanuclear Cluster," European Journal of Inorganic Chemistry, Aug. 2016, vol. 2016 (22), pp. 3536-3540.
Tanaka T., et al., "11B NMR Probes of Copper(II): Finding and Implications of the Cu2+-Promoted Decomposition of ortho-Carborane Derivatives," European Journal of Inorganic Chemistry, Apr. 2016, vol. 2016 (12), pp. 1819-1834.
Tei L., et al., "Target Visualization by MRI Using the Avidin/Biotin Amplification Route: Synthesis and Testing of a Biotin-Gd-DOTA Monoamide Trimer," Chemistry a European Journal, Jul. 2010, vol. 16 (27), pp. 8080-8087.
Terreno E., et al., "Highly Shifted LIPOCEST Agents Based on the Encapsulation of Neutral Polynuclear Paramagnetic Shift Reagents," Chemical Communications, 2008, pp. 600-602.
Thompson M.K., et al., "Cooperative Processes Governing Formation of Small Pentanuclear Lanthanide(II) Nanoclusters and Energy Transport within and between Them," Inorganic Chemistry, Aug. 2001, vol. 40 (17), pp. 4332-4341.
Thompson M.K., et al., "Formation of Two Diverse Classes of Poly(amino-alkoxide) Chelates and their Mononuclear and Polynuclear Lanthanide(III) Complexes," Inorganic Chemistry, Jul. 2003, vol. 42 (16), pp. 4828-4841.
Tombach B., et al., "Value of 1.0-M Gadolinium Chelates: Review of Preclinical and Clinical Data on Gadobutrol," European Radiology, Jun. 2002, vol. 12 (6), pp. 1550-1556.
Tremblay M.S., et al., "Synthesis of Luminescent Heterometallic Bis-lanthanide Complexes via Selective, Sequential Metallation," Chemical Communications, Sep. 2006, pp. 4116-4118.
Tropiano M., et al., "Using Remote Substituents to Control Solution Structure and Anion Binding in Lanthanide Complexes," Chemistry a European Journal, Dec. 2013, vol. 19 (49), pp. 16566-16571.

Van Alphen J., et al., "On Aliphatic Polyamines VII," 1938, vol. 57 (3), pp. 265-276.
Verwilst P., et al., "A Tripodal Ruthenium-Gadolinium Metallostar as a Potential alphavBeta3 Integrin Specific Bimodal Imaging Contrast Agent," Inorganic Chemistry, May 2012, vol. 51 (11), pp. 6405-6411.
Verwilst P., et al., "Recent Advances in Gd-chelate Based Bimodal Optical/MRI Contrast Agents," Chemical Society Reviews, Jan. 2015, vol. 44 (7), pp. 1791-1806.
Vetterlein K., et al., "Capillary Electrophoresis for the Characterization of the Complex Dendrimeric Contrast Agent Gadomer," Electrophoresis, Jun. 2006, vol. 27 (12), pp. 2400-2412.
Vetterlein K., et al., "Comprehensive Profiling of the Complex Dendrimeric Contrast Agent Gadomer Using a Combined Approach of CE, MS, and CE-MS," Electrophoresis, Aug. 2007, vol. 28 (17), pp. 3088-3099.
Wang J., et al., "Anion Separation and Preconcentration with Cyclen and Cyclen-Resorcinarene Derivatives," Journal of Chromatographic Science, Aug. 2009, vol. 47 (7), pp. 510-515.
Wang J., et al., "Multiple Anion Binding by a Zinc-containing Tetratopic Cyclen-resorcinarene," Journal of Inclusion Phenomena and Macrocyclic Chemistry, Jun. 2010, vol. 67 (1), pp. 55-61.
Wang J., et al., "Synthesis, Characterization, and Activity of Cyclotriphosphazene-Cyclene Conjugates," Phosphorus, Sulfur, and Silicon and the Related Elements, 2013, vol. 188 (1-3), pp. 54-58.
Wang L., et al., "A Multiple Gadolinium Complex Decorated Fullerene as a Highly Sensitive T(1) Contrast Agent," Chemical Communications, Mar. 2015, vol. 51 (21), pp. 4390-4393.
Wang L., et al., "Catalytic Cooperativity, Nuclearity, and O2/H2O2 Specificity of Multi-Copper(II) Complexes of Cyclen-Tethered Cyclotriphosphazene Ligands in Aqueous Media," European Journal of Inorganic Chemistry, Nov. 2017, vol. 2017 (42), pp. 4899-4908.
Wangler C., et al., "Antibody-dendrimer Conjugates: the Number, Not the Size of the Dendrimers, Determines the Immunoreactivity," Bioconjugate Chemistry, Apr. 2008, vol. 19 (4), pp. 813-820.
Wangler C., et al., "Improved Syntheses and Applicability of Different DOTA Building Blocks for Multiply Derivatized Scaffolds," Bioorganic & Medicinal Chemistry, Mar. 2008, vol. 16 (5), pp. 2606-2616.
Werner E.J., et al., "High-Relaxivity MRI Contrast Agents: Where Coordination Chemistry Meets Medical Imaging," Angewandte Chemie, 2008, vol. 47 (45), pp. 8568-8580.
Wischnjow A., et al., "Renal Targeting: Peptide-Based Drug Delivery to Proximal Tubule Cells," Bioconjugate Chemistry, Apr. 2016, vol. 27 (4), pp. 1050-1057.
Wu X., et al., "Synthesis and Evaluation of a Peptide Targeted Small Molecular Gd-DOTA Monoamide Conjugate for MR Molecular Imaging of Prostate Cancer," Bioconjugate Chemistry, Aug. 2012, vol. 23 (8), pp. 1548-1556.
Xu H., et al., "Tetraphenylethene Based Zinc Complexes as Fluorescent Chemosensors for Pyrophosphate Sensing," Chinese Chemical Letters, Jul. 2015, vol. 26 (7), pp. 877-880.
Yang X., et al., "Synthesis and Characterization of Side Group-Modified Tetradentate Cyclotriphosphazene Derivatives," Phosphorus, Sulfur, and Silicon and the Related Elements, 2012, vol. 187 (6), pp. 722-727.
Yoo C.E., et al., "Degradation of Myoglobin by Polymeric Artificial Metalloproteases Containing Catalytic Modules with Various Catalytic Group Densities: Site Selectivity in Peptide Bond Cleavage," Journal of the American Chemical Society, Nov. 2003, vol. 125 (47), pp. 14580-14589.
Zhang Y., et al., "Small Cyclenylmidazolium-Containing Molecules and Their Interactions with DNA," Chemistry & Biodiversity, 2014, vol. 11, pp. 233-244.
Zhou Z., et al., "Peptide Targeted Tripod Macrocyclic Gd(III) Chelates for Cancer Molecular MRI," Biomaterials, Oct. 2013, vol. 34 (31), pp. 7683-7693.
Zompa L.J., et al., "Equilibrium Studies of Polynucleating Ligands. I. The Interaction of Tetrakis(aminomethyl)methane with Copper(II) and Hydrogen Ions," Journal of the American Chemical Society, Nov. 1966, vol. 88 (22), pp. 5186-5191.

(56) References Cited

OTHER PUBLICATIONS

Zulkefeli M., et al., "Design and Synthesis of a Stable Supramolecular Trigonal Prism Formed by the Self-assembly of a Linear Tetrakis(Zn2+-cyclen) Complex and Trianionic Trithiocyanuric Acid in Aqueous Solution and its Complexation with DNA (Cyclen=1,4,7,10-tetraazacyclododecane)," Inorganic Chemistry, Oct. 2009, vol. 48 (19), pp. 9567-9578.

Kobelev S.M., et al., "Macrobicycles Based on Cyclen and Cyclam Containing 1,3-disubstituted Adamantane Moieties," Archive for Organic Chemistry, Sep. 2012, vol. 2012 (7), pp. 196-209.

Kobelev S.M., et al., "Synthesis of Macrobi- and Macrotricyclic Compounds Comprising Pyrimidyl Substituted Cyclen and Cyclam," Heterocycles, 2011, vol. 82 (2), pp. 1447-1476.

Kompp; Kompakt., "Basislexikon Chemie", 1999, 2586.

Konig B., et al., "Synthesis of Functionalized Aza-macrocycles and the Application of their Metal Complexes in Binding Processes," Journal of Inclusion Phenomena and Macrocyclic Chemistry, May 2000, vol. 37 (1-4), pp. 39-57.

Kriemen E., et al., "Synthesis and Structural Analysis of 1,4,7,10-Tetraazacyclododecane-1,4,7,10-tetraazidoethylacetic Acid (DOTAZA) Complexes," European Journal of Inorganic Chemistry, Nov. 2015, vol. 2015 (32), pp. 5368-5378.

Kriemen E., et al., "Synthesis of 1,4,7,10-Tetra-azacyclododecan-1,4,7,10-tetra-azidoethylacetic Acid (DOTAZA) and Related "Clickable" DOTA Derivatives," Chemistry an Asian Journal, Aug. 2014, vol. 9 (8), pp. 2197-2204.

Krishan Kumar., et al., "Synthesis, Stability, and Crystal Structure Studies of Some Ca2+, Cu2+, and Zn2+ Complexes of Macrocyclic Polyamino Carboxylates," Inorganic Chemistry, Dec. 1995, vol. 34 (26), pp. 6472-6480.

Kumar A., et al., "Molecular Platform for Design and Synthesis of Targeted Dual-Modality Imaging Probes," Bioconjugate Chemistry, Jan. 2015, vol. 26 (3), pp. 549-558.

Laurent S., et al., "Stability of MRI Paramagnetic Contrast Media: a Proton Relaxometric Protocol for Transmetallation Assessment," Investigative Radiology, Feb. 2001, vol. 36 (2), pp. 115-122.

Leich V., et al., "Formation of a Cationic Calcium Hydride Cluster with a "Naked" Triphenylsilyl Anion by Hydrogenolysis of Bis(triphenylsilyl)calcium," Inorganic Chemistry, May 2015, vol. 54 (10), pp. 4927-4933.

Li C., et al., "Multimodal Image-Guided Enzyme/Prodrug Cancer Therapy," Journal of the American Chemical Society, Nov. 2006, vol. 128 (47), pp. 15072-15073.

Li N., et al., "Cation Separation and Preconcentration Using Columns Containing Cyclen and Cyclen-resorcinarene Derivatives," Journal of Chromatography, Jul. 2012, vol. 1245 (2012), pp. 83-89.

Li W.S., et al., "A Gd3Al Tetranuclear Complex as a Potential Bimodal MRI/optical Imaging Agent," Dalton Transactions, Aug. 2012, vol. 41 (31), pp. 9405-9410.

Liu J., etal., "Molecular Engineering of Aqueous Soluble Triarylboron-Compound-Based Two-Photon Fluorescent Probe for Mitochondria H2S with Analyte-Induced Finite Aggregation and Excellent Membrane Permeability," Analytical Chemistry, 2016, vol. 88 (1), pp. 1052-1057.

Livramento; et al., "A benzene-core trinuclear Gdlll complex: towards the optimization of relaxivity for MRI contrast agent applications at hight magnetic field", The Royal Society of Chemistry 2008, 2008, 1195-1202.

Lopez-Martinez L.M., et al., "Synthesis, Characterization, and Cu2+ Coordination Studies of a 3-Hydroxy-4-pyndinone Aza Scorpiand Derivative," Inorganic Chemistry, Jul. 2016, vol. 55 (15), pp. 7564-7575.

Maindron N., et al., "Near-Infrared-Emitting BODIPY-trisDOTA(111) in as a Monomolecular Multifunctional Imaging Probe: from Synthesis to In Vivo Investigations," Chemistry a European Journal, Aug. 2016, vol. 22 (36), pp. 12670-12674.

Mamedov I., et al., "Structure-related Variable Responses of Calcium Sensitive MRI Probes," Organic & Biomolecular Chemistry, Aug. 2011, vol. 9 (16), pp. 5816-5824.

Martin D., et al., "Discrete Magnesium Hydride Aggregates: A Cationic Mg13H18 Cluster Stabilized by NNNN-Type Macrocycles," Angewandte Chemie, Mar. 2015, vol. 54 (13), pp. 4115-4118.

Martin D., et al., "Hydrido and Allyl/Hydrido Complexes of Early Lanthanides Supported by an NNNN-Type Macrocyclic Ligand," European Journal of Inorganic Chemistry, Aug. 2013, vol. 2013 (22-23), pp. 3987-3992.

Martinez G.V., et al., "Demonstration of a Sucrose-derived Contrast Agent for Magnetic Resonance Imaging of the GI Tract," Bioorganic & Medicinal Chemistry Letters, Apr. 2013, vol. 23 (7), pp. 2061-2064.

Mastarone D.J., et al., "A Modular System for the Synthesis of Multiplexed Magnetic Resonance Probes," Journal of the American Chemical Society, Mar. 2011, vol. 133 (14), pp. 5329-5337.

Merbach A.E., et al.,"Chapter II: Relaxivity of Gadolinium(III) Complexes: Theory and Mechanism" in: The Chemistry of Contrast Agents in Medical Magnetic Resonance Imaging, 2nd Edition, 2013, Table of Contents.

Mier W., et al., "Synthesis of Peptide Conjugated Chelator Oligomers for Endoradiotherapy and MRT Imaging," Tetrahedron Letters, Jul. 2004, vol. 45 (28), pp. 5453-5455.

Mieville P., et al., "Synthesis, Complexation and NMR Relaxation Properties of Gd3+ Complexes of Mes(DO3A)3," Dalton Transactions, Mar. 2011, vol. 40, pp. 4260-4267.

Mishra A., et al., "Facile Synthesis and Relaxation Properties of Novel Bispolyazamacrocyclic Gd3+ Complexes: an Attempt Towards Calcium-sensitive MRI Contrast Agents," Inorganic Chemistry, Feb. 2008, vol. 47 (8), p. 3460.

Muller A., et al., "Preparation of Luminescent Chemosensors by Post-functionalization of Vesicle Surfaces," Organic & Biomolecular Chemistry, 2015, vol. 13 (6), pp. 1690-1699.

Napolitano R., et al., "Synthesis and Relaxometric Characterization of a MRI Gd-Based Probe Responsive to Glutamic Acid Decarboxylase Enzymatic Activity," Journal of Medical Chemistry, Mar. 2013, vol. 56 (6), pp. 2466-2477.

Niedbalski P., et al., "13C Dynamic Nuclear Polarization Using a Trimeric Gd3+ Complex as an Additive," The Journal of Physical Chemistry, Jul. 2017, vol. 121 (27), pp. 5127-5135.

Nithyakumar A., et al., "Tri- and Tetranuclear RuII-GdIII2 and RuII-GdIII3 d-f Heterometallic Complexes as Potential Bimodal Imaging Probes for MRI and Optical Imaging," New Journal of Chemistry, Mar. 2016, vol. 40, pp. 4606-4616.

"NMRD measurements—final report and Sample characteristics of the samples used in the experimental report", Dec. 19, 2014.

Notni J., et al., "Convenient Synthesis of 68Ga-Labeled Gadolinium(III) Complexes: Towards Bimodal Responsive Probes for Functional Imaging with PET/MRI," Chemistry a European Journal, Sep. 2013, vol. 19 (38), pp. 12602-12606.

Olga Capasso "Letter accompanying Notice of OppositionAgainst EP 3303307B1" and "Notice of Opposition Against EP 3303307B1",submitted to European Patent Office, Jun. 4, 2020.

Oltmanns D., et al., "Zn(II)-bis(cyclen) Complexes and the Imaging of Apoptosis/Necrosis," Bioconjugate Chemistry, Oct. 2011, vol. 22 (12), pp. 2611-2624.

Overoye-Chan K., et al., "EP-2104R: A Fibrin-Specific Gadolinium-Based MRI Contrast Agent for Detection of Thrombus," Journal of the American Chemical Society, May 2008, vol. 130 (18), pp. 6025-6039.

Pang X., et al., "Bimetallic Schiff-base Aluminum Complexes Based on Pentaerythrityl Tetramine and their Stereoselective Polymerization of Racemic Lactide," RSC Advances, May 2014, vol. 4, pp. 22561-22566.

Paris J., et al., "Auto-assembling of Ditopic Macrocyclic Lanthanide Chelates with Transition-metal Ions. Rigid Multimetallic High Relaxivity Contrast Agents for Magnetic Resonance Imaging," Inorganic Chemistry, Jun. 2006, vol. 45 (13), pp. 5092-5102.

Pikkemaat J.A., et al., "Dendritic PARACEST Contrast Agents for Magnetic Resonance Imaging," Contrast Media & Molecular Imaging, Sep.-Oct. 2007, vol. 2 (5), pp. 229-239.

Pittman C.U., et al., "Columns: Polymer Supports in Synthesis," Polymer News, 2005, vol. 30 (1), pp. 14-15.

(56) References Cited

OTHER PUBLICATIONS

Polyanichko K.V., et al., "Synthesis of Dendronized Polymeric Chelating Agents using Hydrazone Ligation Strategy," European Polymer Journal, Jul. 2017, vol. 92, pp. 117-125.

Preslar A.T., et al., "Correction to Gd(III)-Labeled Peptide Nanofibers for Reporting on Biomaterial Localization in Vivo," ACS Nano, Nov. 2015, vol. 9 (11), p. 11502.

Preslar A.T., et al., "Gd(III)-Labeled Peptide Nanofibers for Reporting on Biomaterial Localization in Vivo," ACS Nano, Jun. 2014, vol. 8 (7), pp. 7325-7332.

Raymond Kenneth N.; et al., "Next Generation, Hight Relaxivity Gadolinium MRI Agents", Bioconjugate Chern., 2005, vol. 16, Issue 1, 3-8.

Regueiro-Figueroa M., et al., "Structure and Dynamics of Lanthanide(III) Complexes with an N-Alkylated do3a Ligand (H3do3a=1,4,7,10-Tetraazacyclododecane-1,4,7-triacetic Acid): A Combined Experimental and DFT Study," European Journal of Inorganic Chemistry, Aug. 2010, vol. 2010 (23), pp. 3586-3595.

Reichert D.E., et al., "Molecular Mechanics Investigation of Gadolinium(III) Complexes," Inorganic Chemistry, Nov. 1996, vol. 35 (24), pp. 7013-7020.

Revesz L., et al., "Synthesis of Novel Piperazine Based Building Blocks: 3,7,9-triazabicyclo[3.3.1]nonane, 3,6,8-triazabicyclo[3.2.2]nonane, 3-oxa-7,9-diazabicyclo[3.3.1]nonane and 3-oxa-6,8-diazabicyclo[3.2.2]nonane," Tetrahedron Letters, Aug. 2005, vol. 46 (33), pp. 5577-5580.

Riechers A., et al., "Binding of Phosphorylated Peptides and Inhibition of their Interaction with Disease-relevant Human Proteins by Synthetic Metal-chelate Receptors," Journal of Molecular Recognition, May-Jun. 2010, vol. 23 (3), pp. 329-334.

Rinck; et al., "Field strength and dose dependence of contrast enhancement by gadolinium-based MR contrast agents", European Radiology, 1999, vol. 9, 998-1004.

Rodriguez-Rodriguez A., et al., "Stable Mn2+, Cu2+ and Ln3+ Complexes with Cyclen-based Ligands Functionalized with Picolinate Pendant Arms," Dalton Transactions, 2015, vol. 44, pp. 5017-5031.

Rompp; Kompakt., "Basislexikon Chemie", 1998, 1213-1214.

HIGH RELAXIVITY GADOLINIUM CHELATE COMPOUNDS FOR USE IN MAGNETIC RESONANCE IMAGING

CROSS REFERENCE TO RELATED APPLICATIONS

The present application is a Continuation of U.S. Ser. No. 16/463,076, filed 22 Mar. 2019 which is a U.S. national stage filing under 35 U.S.C. § 371 of International Application No. PCT/EP2017/080306, filed 24 Nov. 2017, which claims priority to European Patent Application No. EP 16200932.8, filed 28 Nov. 2016, the disclosures of each of which are incorporated in their entirety herein by this reference.

FIELD OF THE INVENTION

The present invention relates to the items characterized in the patent claims, namely to high relaxivity gadolinium chelate compounds based on a low molecular weight core polyamine to methods of preparing said compounds, to the use of said compounds as MRI contrast agents and to their use in a mammalian body.

BACKGROUND

1. Introduction

Nine gadolinium-based contrast agents (GBCAs) have been approved for clinical use: gadopentetate dimeglumine (Magnevist®), gadoterate meglumine (Dotarem®), gadoteridol (ProHance®), gadodiamide (Omniscan®), gadobutrol (Gadovist®), gadoversetamide (OptiMARK®), gadoxetic acid (Primovist®), gadobenate dimeglumine (MultiHance®), and gadofosveset trisodium (Vasovist®/ Ablavar®). With the exception of gadoxetic acid, gadobenate dimeglumine, and gadofosveset trisodium, the GBCAs exhibit a strictly extracellular passive distribution in the body and are excreted exclusively via the kidney.

Gadoxetic acid and gadobenate dimeglumine exhibit a different pharmacokinetic profile than the other agents. In addition to the extracellular distribution, they are taken up and are also excreted partially via the liver. This allows, besides the classical imaging possibilities (e.g. central nervous system, angiography, extremities, heart, head/face/neck, abdomen, and breast imaging), also liver imaging due to the enhancement of liver parenchyma caused by the GBCAs' uptake in hepatocytes.

In contrast to the other GBCAs gadofosveset trisodium shows no passive diffusion in the body and remains in the vascular space. The prolonged period in the blood vessels caused by the reversible binding to HSA (human serum albumin) allows high resolution MR angiographies.

The various GBCAs differ in their efficacy which is given by their longitudinal (r1) and transversal (r2) relaxivity and is dependent on magnetic field strengths, temperature, and different intrinsic factors of the metal chelates. The intrinsic relaxivity influencing parameters are mainly the number of water molecules directly bound to the gadolinium (so-called inner-sphere water, q), the mean residence time of the inner sphere water molecules ($\tau m$), the number and residence times of water molecules in the second hydration sphere (so-called second sphere water), and the rotational diffusion ($\tau r$) (Helm L. et. al., Future Med. Chem. 2010, 2, 385-396). In terms of their relaxivity all the commercially available GBCAs are very similar to each other and derived from a range of 4 to 7 L mmol$^{-1}$ s$^{-1}$.

Strategies for increasing the sensitivity of GBCAs are frequently described in the literature (Caravan P. et. al. Chem. Soc. Rev., 2006, 35, 512-523, Helm et.al. Future Med. Chem. 2010, 2,385-396, Jacques V. Invest. Radiol. 2010, 45, 613-624). One of the strategies is the increase of the inner sphere water molecules (q) that are water molecules which are directly coordinated to the gadolinium ion in the chelate. As the examples of AAZTA and HOPO-based ligands show, the increase of the inner sphere water molecules from one to two leads to a significant increase in relaxivity. Another strategy to increase the relaxivity is the slowing of the rotational diffusion of the molecule. The so-called tumbling rate ($\tau r$, see introduction) describes the tumbling of the molecule in solution and is mainly affected by the molecular size and protein binding of the GBCA (Merbach A. S. et. al., The Chemistry of Contrast Agents in Medical Magnetic Resonance Imaging, 2013, ISBN: 978-1-119-99176-2).

A further important characteristic of the GBCAs is their complex stability. The potential of the GBCAs to release free toxic Gd$^{3+}$ ions is a major safety issue and of utmost importance in particular for patients with end-stage renal disease. Nephrogenic systemic fibrosis (NSF) is a rare and serious syndrome that is associated with the exposure to GBCAs in patients with severe kidney failure. NSF involves fibrotic changes in the skin and many organs. In 2010, the U.S. Food and Drug Administration (FDA) published revised labeling recommendations for four GBCAs which have been principally implicated in NSF, including gadodiamide (Omniscan®), gadobenate dimeglumine (MultiHance®), gadopentetate dimeglumine (Magnevist®), and gadoversetamide (OptiMARK®) (Yang L et. al. Radiology. 2012, 265, 248-253). At first glance the stability of all GBCAs is very high, but significant differences exist between the linear and macrocyclic agents and between the ionic and nonionic representatives of the linear agents. The macrocyclic GBCAs possess the highest complex stabilities (Frenzel T. et. al. Invest. Radiol. 2008, 43, 817-828). Due to the better awareness of risk patients, the use of lower doses and more widespread use of the macrocyclic GBCAs the incidence of NSF has decreased in the last years (Wang Y. et.al. Radiology. 2011, 260, 105-111 and Becker S. et.al. Nephron. Clin. Pract. 2012, 121, c91-c94).

The crucial issue for clinical applications is in vivo stability. The kinetic inertness combined with the thermodynamic stability is particularly with regard to the risk of nephrogenic systemic fibrosis (NSF) the best predictor of the in vivo toxicity of q=2 chelates (Merbach A. S. et. al., The Chemistry of Contrast Agents in Medical Magnetic Resonance Imaging, 2013, ISBN: 978-1-119-99176-2, page 157-208). The complexes with q=2 show two-fold enhancement of relaxivity but, unfortunately, they have a lower stability than q=1 compounds (Hermann P. et.al. Dalton Trans., 2008, 3027-3047).

2. Description of the Prior Art, Problem to be Solved and its Solution

Several Macrocyclic Compounds are Described in the Prior Art.

EP1931673 B1 and EP2457914 B1 relate to pyDO3A (q=2), DO3A and DOTA compounds comprising short aminoalcohol chains and metal complexes for medical imaging.

Macrocyclic lanthanide DO3A- and DOTA-like GBCAs with high relaxivities are described in the prior art.

Ranganathan R. S. et.al. (Investigative Radiology 1998; 33:779-797) investigated the effect of multimerization on the relaxivity of macrocyclic gadolinium chelates. WO199531444 relates to monomeric and multimeric compounds having enhanced relaxivities.

U.S. Pat. No. 5,679,810 relates to linear oligomer polychelant compounds and chelates formed therewith, having alternating chelant and linker moieties bound together by amide or ester moieties, and to their use in diagnostic imaging.

U.S. Pat. No. 5,650,133 relates to dichelants, in particular compounds having two macrocyclic chelant groups linked by a bridge containing an ester or amide bond, and to metal chelates thereof, and to their use in diagnostic imaging.

U.S. Pat. No. 8,545,813 B2 relates to contrast agents for MRI and related methods of use and describes MR contrast agents via click chemistry with various number of Gd(III) complexes covalently attached to the substrates.

WO 2012/059576A1 relates to the field of Magnetic Resonance Imaging (MRI) based on Chemical Exchange-dependent Saturation Transfer (CEST).

Aime S. et.al. (Contrast Media Mol. Imaging 2013, 8, 475-486) describe the use of gadolinium complexes for in vitro cellular labeling.

WO2006/002873 relates to the field of diagnostic imaging and to novel contrast agents possessing high relaxivity.

Zhao G. et.al. (Inorganica Chimica Acta 406, (2013), 146-152) describe two multinuclear gadolinium macrocyclic complexes as contrast agents with high relaxivity.

Zhang W. et.al. (Z. Anorg. Allg. Chem. 2015, 641, (3-4), 578-585) describe a tetranuclear gadolinium macrocyclic complex with high relaxivity for MRI.

Alexander V. et.al. (Inorg. Chem. 2005, 44, 9434-9443) describe the synthesis and relaxivity studies of a tetranuclear gadolinium complex.

WO 97/32862 A1 describes gadolinium polychelants as magnetic resonance imaging agents which are linking at least two units of chelant to the amino groups of a target carrier structure (like e.g. a protein, aminoacid or peptide).

US Application Publication No. 2007/202047 relates to gadolinium chelate compounds for use in magnetic resonance imaging, which are derived from a chelating molecule selected from 1,4,7,10-tetraazacyclododecane-1,4,7,10-tetraacetic acid (DOTA) and diethylentriaminepentaacetic acid (DTPA), wherein at least one of the carboxylic groups of the chelating molecule is reacted with an amine.

GBCAs with higher relaxivity offer on the one hand the opportunity of a significant dose reduction and on the other an increased sensitivity in the MRI examination of many diseases using the standard dose (Giesel F L. et.al. Eur. Radiol. 2010, 20, 2461-2474).

However, there is an unmet medical need to provide GBCAs for general use in magnetic resonance imaging, which:

exhibit high relaxivity, show a favorable pharmacokinetic profile, are completely excreted, are chemically stable, exhibit high water solubility, offer the potential for a significant dose reduction, and are suitable for imaging of different body regions.

The state of the art described above does not describe the specific high relaxivity extracellular gadolinium chelate compounds of general formula (I) of the present invention as defined herein, or a stereoisomer, a tautomer, an N-oxide, a hydrate, a solvate, or a salt thereof, or a mixture of same, as described and defined herein, and as hereinafter referred to as "compounds of the present invention".

It has now been found, and this constitutes the basis of the present invention, that said compounds of the present invention have surprising and advantageous properties.

In particular, said compounds of the present invention have been found to exhibit a balanced profile of a high relaxivity, a favorable pharmacokinetic profile, a complete excretion, a high stability, a high solubility, the potential for a significant dose reduction and the potential for whole body imaging, and they may therefore be used as contrast agents for magnetic resonance imaging (MRI).

SUMMARY

The present invention describes a new class of high relaxivity extracellular gadolinium chelate complexes, methods for their preparation, and their use as MRI contrast agents.

BRIEF DESCRIPTION

In accordance with a first aspect, the present invention covers compounds of general formula (I),

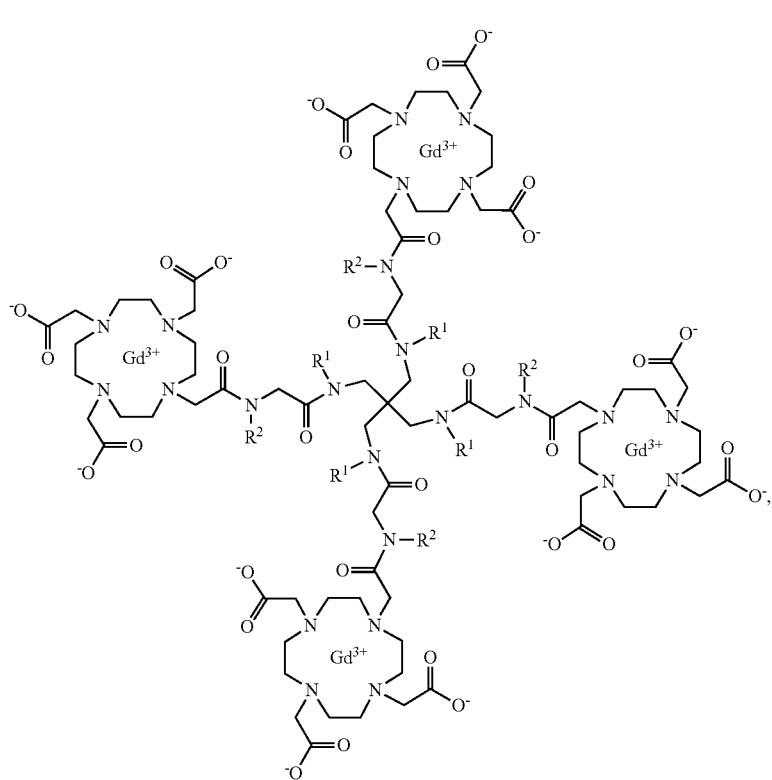

(I)

in which:

R¹ represents, independently from each other, a hydrogen atom or a methyl group;

R2 represents, independently from each other, a group selected from:

$C_1$-$C_6$-alkyl, $C_3$-$C_6$-cycloalkyl, $C_2$-$C_6$-hydroxyalkyl, ($C_1$-$C_3$-alkoxy)-($C_2$-$C_4$-alkyl)-, 2-(2-methoxyethoxy)ethyl, 2-(2-ethoxyethoxy)ethyl, oxetan-3-yl, tetrahydro-2H-pyran-4-yl, and phenyl, wherein said $C_1$-$C_6$-alkyl group is optionally substituted, identically or differently, with a phenyl group, which phenyl group is optionally substituted, one, two, or three times, identically or differently, with a halogen atom or a group selected from:

$C_1$-$C_3$-alkyl, $C_1$-$C_3$-haloalkyl, and $C_1$-$C_3$-alkoxy, and wherein said phenyl group is optionally substituted, one, two, or three times, identically or differently, with a halogen atom or a group selected from:

$C_1$-$C_3$-alkyl, $C_1$-$C_3$-haloalkyl, and $C_1$-$C_3$-alkoxy;

or a stereoisomer, a tautomer, an N-oxide, a hydrate, a solvate, or a salt thereof, or a mixture of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

Should a composite substituent be composed of more than one parts, e.g. ($C_1$-$C_3$-alkoxy)-($C_2$-$C_6$-alkyl)-, it is possible for the position of a given part to be at any suitable position of said composite substituent, i.e. the $C_1$-$C_3$-alkoxy part can be attached to any carbon atom of the $C_2$-$C_6$-alkyl part of said ($C_1$-$C_3$-alkoxy)-($C_2$-$C_6$-alkyl)- group. A hyphen at the beginning or at the end of such a composite substituent indicates the point of attachment of said composite substituent to the rest of the molecule.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5, or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl, or 1,3-dimethylbutyl group, or an isomer thereof. Particularly, said group has 1, 2, 3, or 4 carbon atoms ("$C_1$-$C_4$-alkyl"), e.g. a methyl, ethyl, propyl, isopropyl, butyl, sec-butyl isobutyl, or tert-butyl group, more particularly 1, 2, or 3 carbon atoms ("$C_1$-$C_3$-alkyl"), e.g. a methyl, ethyl, n-propyl, or isopropyl group.

The term "$C_1$-$C_3$-haloalkyl" means a linear or branched, saturated, monovalent hydrocarbon group in which the term "$C_1$-$C_3$-alkyl" is as defined supra, and in which one or more of the hydrogen atoms are replaced, identically or differently, with a halogen atom. Particularly, said halogen atom is a fluorine atom. Said $C_1$-$C_3$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl, or 1,3-difluoropropan-2-yl.

The term "$C_2$-$C_6$-hydroxyalkyl" means a linear or branched, saturated, monovalent hydrocarbon group in which the term "$C_2$-$C_6$-alkyl" is defined supra, and in which 1, 2, or 3 hydrogen atoms are replaced with a hydroxy group, e.g. a 2-hydroxyethyl, 3-hydroxypropyl, 2-hydroxypropyl, 1-hydroxypropan-2-yl, 2,3-dihydroxypropyl, 1,3-dihydroxypropan-2-yl, 1,3-dihydroxy-2-(hydroxymethyl)propan-2-yl, 3-hydroxy-2-methyl-propyl, or 2-hydroxy-2-methyl-propyl group.

The term "$C_1$-$C_3$-alkoxy" means a linear or branched, saturated, monovalent group of formula ($C_1$-$C_3$-alkyl)-O—, in which the term "$C_1$-$C_3$-alkyl" is as defined supra, e.g. a methoxy, ethoxy, n-propoxy, or isopropoxy group.

The term "$C_3$-$C_6$-cycloalkyl" means a saturated, monovalent, mono- or bicyclic hydrocarbon ring which contains 3, 4, 5, or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl, or cyclohexyl group.

The term "$C_1$-$C_6$", as used in the present text, e.g. in the context of the definition of "$C_1$-$C_6$-alkyl" means an alkyl group having a finite number of carbon atoms of 1 to 6, i.e. 1, 2, 3, 4, 5, or 6 carbon atoms.

Further, as used herein, the term "$C_3$-$C_6$", as used in the present text, e.g. in the context of the definition of "$C_3$-$C_6$-cycloalkyl", means a cycloalkyl group having a finite number of carbon atoms of 3 to 6, i.e. 3, 4, 5, or 6 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_1$-$C_3$" encompasses $C_1$, $C_2$, $C_3$, $C_1$-$C_3$, $C_1$-$C_2$, and $C_2$-$C_3$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$.

The compounds of this invention may contain one or more asymmetric center, depending upon the location and nature of the various substituents desired. Asymmetric carbon atoms may be present in the (R) or (S) configuration, which can result in racemic mixtures in the case of a single asymmetric center, and in diastereomeric mixtures in the case of multiple asymmetric centers. In certain instances, asymmetry may also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric, and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivatization, optimally chosen to maximize the separation of the enantiomers. Suitable chiral HPLC columns are manufactured by Daicel, e.g., Chiracel OD and Chiracel OJ among many others, all routinely selectable. Enzymatic separations, with or without derivatization, are also useful. The optically active compounds of this invention can likewise be obtained by chiral syntheses utilizing optically active starting materials.

In order to limit different types of isomers from each other reference is made to IUPAC Rules Section E (Pure Appl. Chem. 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention can exist as N-oxides, which are defined in that at least one nitrogen of the compounds of the present invention is oxidized. The present invention includes all such possible N-oxides.

The present invention also relates to useful forms of the compounds as disclosed herein, such as metabolites, hydrates, solvates, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-, etc. solvates or hydrates, respectively, are possible. The present invention includes all such hydrates or solvates.

Further, the compounds of the present invention can exist in the form of a salt. Said salt may be either an inorganic or organic addition salt, particularly any pharmaceutically acceptable inorganic or organic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. The production of especially neutral salts is described in U.S. Pat. No. 5,560,903.

Pharmaceutically acceptable salts of the compounds according to the invention include salts of mineral acids and carboxylic acids, for example, without being limited thereto, salts of hydrochloric acid, sulfuric acid, phosphoric acid, acetic acid, propionic acid, lactic acid, tartaric acid, malic acid, citric acid, fumaric acid, maleic acid, aspartic acid, and glutamic acid.

Those skilled in the art will further recognize that acid addition salts of the claimed compounds may be prepared by reaction of the compounds with the appropriate inorganic or organic acid via any of a number of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

This applies analogously to cases in which synthesis intermediates or example compounds or salts thereof have been obtained, by the preparation and/or purification processes described, as solvates, such as hydrates with (if defined) unknown stoichiometric composition.

In accordance with a second embodiment of the first aspect, the present invention covers compounds of general formula (I), supra, wherein:
$R^1$ represents a hydrogen atom;
$R^2$ represents a group selected from:
$C_1$-$C_6$-alkyl, $C_3$-$C_6$-cycloalkyl, $C_2$-$C_4$-hydroxyalkyl, ($C_1$-$C_3$-alkoxy)-($C_2$-$C_4$-alkyl)-, oxetan-3-yl, tetrahydro-2H-pyran-4-yl, and phenyl,
wherein said $C_1$-$C_6$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy;
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

In accordance with a third embodiment of the first aspect, the present invention covers compounds of general formula (I), supra, wherein:
$R^1$ represents a hydrogen atom;
$R^2$ represents a group selected from:
$C_1$-$C_6$-alkyl, $C_3$-$C_6$-cycloalkyl, ($C_1$-$C_3$-alkoxy)-($C_2$-$C_4$-alkyl)-, and phenyl,
wherein said $C_1$-$C_6$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

In accordance with a fourth embodiment of the first aspect, the present invention covers compounds of general formula (I), supra, wherein:
$R^1$ represents a hydrogen atom;
$R^2$ represents a group selected from:
$C_1$-$C_4$-alkyl, $C_3$-$C_5$-cycloalkyl, ($C_1$-$C_2$-alkoxy)-($C_2$-$C_3$-alkyl)-, and phenyl,
wherein said $C_1$-$C_4$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

In accordance with a fifth embodiment of the first aspect, the present invention covers compounds of general formula (I), supra, wherein:
$R^1$ represents a hydrogen atom;
$R^2$ represents a group selected from:
methyl, ethyl, isopropyl, 2-methylpropyl, benzyl, cyclopropyl, cyclopentyl, 2-methoxyethyl, 2-ethoxyethyl, and phenyl;
or a stereoisomer, a tautomer, an N-oxide, a hydrate, a solvate, or a salt thereof, or a mixture of same.

In a further embodiment of the above-mentioned aspect, the invention relates to compounds of formula (I), wherein:
$R^1$ represents, independently from each other, a hydrogen atom or a methyl group.

In a further embodiment of the above-mentioned aspect, the invention relates to compounds of formula (I), wherein:
$R^1$ represents a hydrogen atom.

In a further embodiment of the above-mentioned aspect, the invention relates to compounds of formula (I), wherein:
$R^2$ represents, independently from each other, a group selected from:
$C_1$-$C_6$-alkyl, $C_3$-$C_6$-cycloalkyl, $C_2$-$C_6$-hydroxyalkyl, ($C_1$-$C_3$-alkoxy)-($C_2$-$C_4$-alkyl)-, 2-(2-methoxyethoxy)ethyl, 2-(2-ethoxyethoxy)ethyl, oxetan-3-yl, tetrahydro-2H-pyran-4-yl, and phenyl,
wherein said $C_1$-$C_6$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy.

In a further embodiment of the above-mentioned aspect, the invention relates to compounds of formula (I), wherein: $R^2$ represents a group selected from:

$C_1$-$C_6$-alkyl, $C_3$-$C_6$-cycloalkyl, $C_2$-$C_4$-hydroxyalkyl, ($C_1$-$C_3$-alkoxy)-($C_2$-$C_4$-alkyl)-, oxetan-3-yl, tetrahydro-2H-pyran-4-yl, and phenyl, wherein said $C_1$-$C_6$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy.

In a further embodiment of the above-mentioned aspect, the invention relates to compounds of formula (I), wherein: $R^2$ represents a group selected from:

$C_1$-$C_6$-alkyl, $C_3$-$C_6$-cycloalkyl, ($C_1$-$C_3$-alkoxy)-($C_2$-$C_4$-alkyl)-, and phenyl, wherein said $C_1$-$C_6$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy.

In a further embodiment of the above-mentioned aspect, the invention relates to compounds of formula (I), wherein: $R^2$ represents a group selected from:

$C_1$-$C_4$-alkyl, $C_3$-$C_5$-cycloalkyl, ($C_1$-$C_2$-alkoxy)-($C_2$-$C_3$-alkyl)-, and phenyl, wherein said $C_1$-$C_4$-alkyl group is optionally substituted, identically or differently, with a phenyl group, which phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy,
and
wherein said phenyl group is optionally substituted, one, two, or three times, identically or differently, with a halogen atom or a group selected from:
$C_1$-$C_3$-alkyl, $C_1$-$C_3$-haloalkyl, and $C_1$-$C_3$-alkoxy.

In a further embodiment of the above-mentioned aspect, the invention relates to compounds of formula (I), wherein: $R^2$ represents a group selected from:

methyl, ethyl, isopropyl, 2-methylpropyl, benzyl, cyclopropyl, cyclopentyl, 2-methoxyethyl, 2-ethoxyethyl, and phenyl.

It is to be understood that the present invention relates also to any combination of the embodiments described above.

Another embodiment of the first aspect are compounds of formula (I) selected from the group consisting of:

Tetragadolinium [4,10-bis(carboxylatomethyl)-7-{3,13-dimethyl-8,8-bis({[(methyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl]-acetate, Tetragadolinium [4,10-bis(carboxylatomethyl)-7-{3,13-diethyl-8,8-bis({[(ethyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl]acetate, Tetragadolinium {4,10-bis(carboxylatomethyl)-7-[15-(2-methoxyethyl)-10,10-bis[({[(2-methoxyethyl){[4,7,10-tris(carboxylatomethyl)-1,4,7,10-tetraazacyclododecan-1-yl]-acetyl}amino]acetyl}amino)methyl]-7,13,16-trioxo-5-{[4,7,10-tris(carboxylatomethyl)-1,4,7,10-tetraazacyclododecan-1-yl]acetyl}-2-oxa-5,8,12,15-tetraazaheptadecan-17-yl]-1,4,7,10-tetraazacyclododecan-1-yl}acetate, Tetragadolinium {4,10-bis(carboxylatomethyl)-7-[16-(2-ethoxyethyl)-11,11-bis[({[(2-ethoxyethyl){[4,7,10-tris(carboxylatomethyl)-1,4,7,10-tetraazacyclododecan-1-yl]-acetyl}amino]acetyl}amino)methyl]-8,14,17-trioxo-6-{[4,7,10-tris(carboxylatomethyl)-1,4,7,10-tetraazacyclododecan-1-yl]acetyl}-3-oxa-6,9,13,16-tetraazaoctadecan-18-yl]-1,4,7,10-tetraazacyclododecan-1-yl}acetate, Tetragadolinium [4,10-bis(carboxylatomethyl)-7-{3,13-diisopropyl-8,8-bis({[(isopropyl-{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium {4,10-bis(carboxylatomethyl)-7-[3-isobutyl-8,8-bis({[(isobutyl{[4,7,10-tris(carboxylatomethyl)-1,4,7,10-tetraazacyclododecan-1-yl]acetyl}amino)acetyl]amino}-methyl)-15-methyl-2,5,11-trioxo-13-{[4,7,10-tris(carboxylatomethyl)-1,4,7,10-tetraazacyclododecan-1-yl]acetyl}-3,6,10,13-tetraazahexadec-1-yl]-1,4,7,10-tetraazacyclododecan-1-yl}acetate, Tetragadolinium [4,10-bis(carboxylatomethyl)-7-{3,13-dicyclopropyl-8,8-bis({[(cyclopropyl-{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{3,13-dicyclopentyl-8,8-bis({[(cyclopentyl-{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{2,5,11,14-tetraoxo-3,13-diphenyl-8,8-bis({[(phenyl{[4,7,10-tris(carboxylatomethyl)-1,4,7,10-tetraazacyclododecan-1-yl]acetyl}-amino)acetyl]amino}methyl)-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl]acetate, and Tetragadolinium [4,10-bis(carboxylatomethyl)-7-{3,13-dibenzyl-8,8-bis({[(benzyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl], acetate, or a stereoisomer, a tautomer, an N-oxide, a hydrate, a solvate, or a salt thereof, or a mixture of same.

In accordance with another aspect, the present invention covers methods of preparing compounds of the present invention, said methods comprising the steps as described in the Experimental Section herein.

In accordance with a further aspect, the present invention covers intermediate compounds which are useful for the preparation of the compounds of general formula (I), supra. Particularly, the invention covers intermediate compounds of general formula (VI):

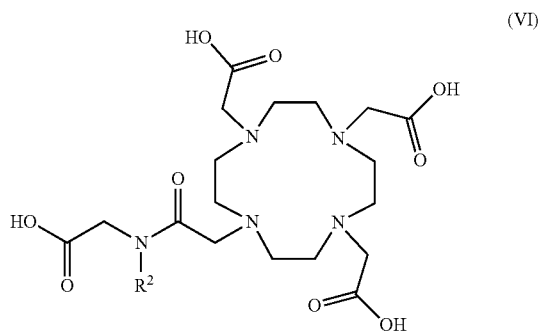

(VI)

in which $R^2$ is as defined for the compounds of general formula (I), supra.

Particularly, the inventions covers intermediate compounds of general formula (VII):

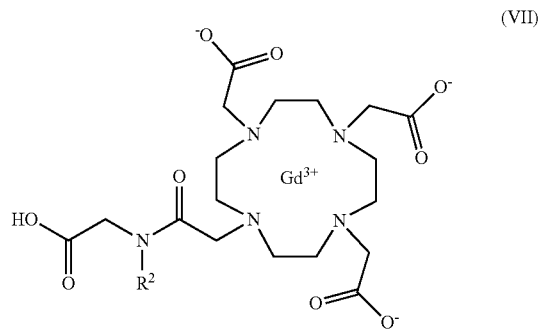

(VII)

in which $R^2$ is as defined for the compounds of general formula (I), supra.

Particularly, the inventions covers intermediate compounds of general formula (VIII):

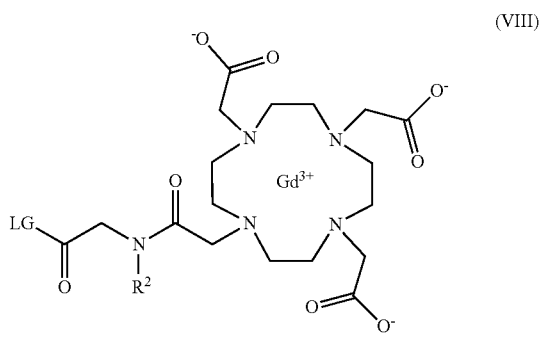

(VIII)

in which $R^2$ is as defined for the compounds of general formula (I), supra, and LG represents an activating leaving group, such as for example 4-nitrophenol, or a group as defined for the synthesis of the compounds of the general formula (I) infra, for the preparation of a compound of general formula (I) as defined supra.

In accordance with a further aspect, the present invention covers the use of said intermediate compounds for the preparation of a compound of general formula (I) as defined supra.

In accordance with a further aspect, the present invention covers the use of the intermediate compounds of general formula (VI):

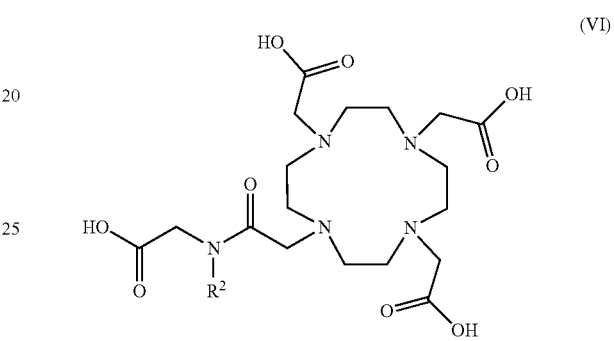

(VI)

in which $R^2$ is as defined for the compounds of general formula (I), supra, for the preparation of a compound of general formula (I) as defined supra.

In accordance with a further aspect, the present invention covers the use of the intermediate compounds of general formula (VII):

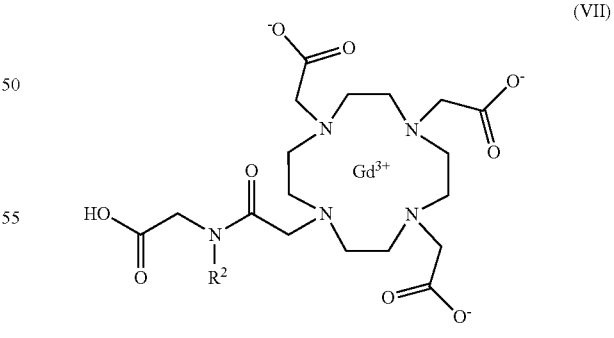

(VII)

in which $R^2$ is as defined for the compounds of general formula (I), supra, for the preparation of a compound of general formula (I) as defined supra.

In accordance with a further aspect, the present invention covers the use of the intermediate compounds of general formula (VIII):

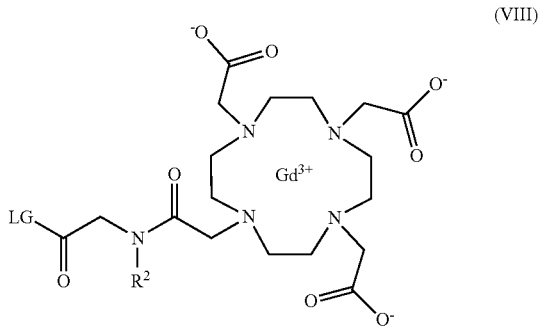

(VIII)

in which R² is as defined for the compounds of general formula (I), supra, and LG represents an activating leaving group, such as for example 4-nitrophenol, or a group as defined for the synthesis of the compounds of the general formula (I) infra, for the preparation of a compound of general formula (I) as defined supra.

In accordance with a further aspect, the present invention covers the use of the intermediate compounds of general formula (IX):

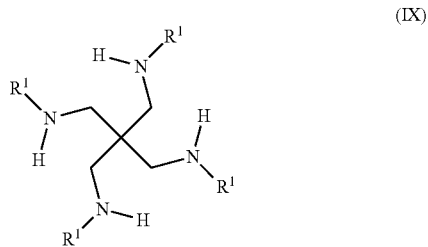

(IX)

in which R¹ is as defined for the compounds of general formula (I), supra, for the preparation of a compound of general formula (I) as defined supra.

More particularly still, the present invention covers the intermediate compounds which are disclosed in the example section of this text, infra.

Another aspect of the invention is the use of a compound of general formula (I) for diagnostic imaging.

Preferably, the use of a compound of the invention in the diagnosis is performed using magnetic resonance imaging (MRI).

Another aspect of the invention are compounds of general formula (I) for use in diagnostic imaging.

Another aspect of the invention are compounds of general formula (I) for use in magnetic resonance imaging (MRI).

The invention also contains compounds of general formula (I) for the manufacture of diagnostic agents.

Another aspect of the invention is the use of the compounds of general formula (I) or mixtures thereof for the manufacture of diagnostic agents.

Another aspect of the invention is the use of the compounds of general formula (I) or mixtures thereof for the manufacture of diagnostic agents for magnetic resonance imaging (MRI).

Another aspect of the invention is a method of imaging body tissue in a patient, comprising the steps of administering to the patient an effective amount of one or more compounds of general formula (I) in a pharmaceutically acceptable carrier, and subjecting the patient to NMR tomography. Such a method is described in U.S. Pat. No. 5,560,903.

For the manufacture of diagnostic agents, for example the administration to human or animal subjects, the compounds of general formula (I) or mixtures will conveniently be formulated together with pharmaceutical carriers or excipient. The contrast media of the invention may conveniently contain pharmaceutical formulation aids, for example stabilizers, antioxidants, pH adjusting agents, flavors, and the like. Production of the diagnostic media according to the invention is also performed in a way known in the art, see U.S. Pat. No. 5,560,903. They may be formulated for parenteral or enteral administration or for direct administration into body cavities. For example, parenteral formulations contain a sterile solution or suspension in a dose of 0.0001-5 mmol gadolinium/kg body weight, especially 0.005-0.5 mmol gadolinium/kg body weight of the compound of formula (I) according to this invention. Thus the media of the invention may be in conventional pharmaceutical formulations such as solutions, suspensions, dispersions, syrups, etc. in physiologically acceptable carrier media, preferably in water for injections. When the contrast medium is formulated for parenteral administration, it will be preferably isotonic or hypertonic and close to pH 7.4.

In a further aspect, the invention is directed to a method of diagnosing and health monitoring of patients. This method comprises a) administering to a human in need of such diagnosis a compound of the invention for detecting the compound in the human as described above and herein, and b) measuring the signal arising from the administration of the compound to the human, preferably by magnetic resonance imaging (MRI).

General Synthesis

The compounds according to the invention can be prepared according to the following schemes 1 and 2.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

The term "amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl, and N-silyl, and which is chosen from but not limited to those described in the textbook Greene and Wuts, Protecting groups in Organic Synthesis, third edition, page 494-653, included herewith by reference. The "amine-protecting group" is preferably carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT), or the protected amino group is a 1,3-dioxo-1,3-dihydro-2H-isoindol-2-yl (phthalimido) or an azido group.

The term "carboxyl-protecting group" as employed herein by itself or as part of another group is known or obvious to someone skilled in the art, which is chosen from but not limited to a class of protecting groups namely esters, amides, and hydrazides, and which is chosen from but not limited to those described in the textbook Greene and Wuts, Protecting groups in Organic Synthesis, third edition, page 369-453, included herewith by reference. The "carboxyl-protecting group" is preferably methyl, ethyl, propyl, butyl, tert-butyl, allyl, benzyl, 4-methoxybenzyl, or 4-methoxyphenyl.

The contents of the documents which are cited herein are hereby incorporated by reference.
A route for the preparation of compounds of general formula (VI) is described in Scheme 1.
Scheme 1
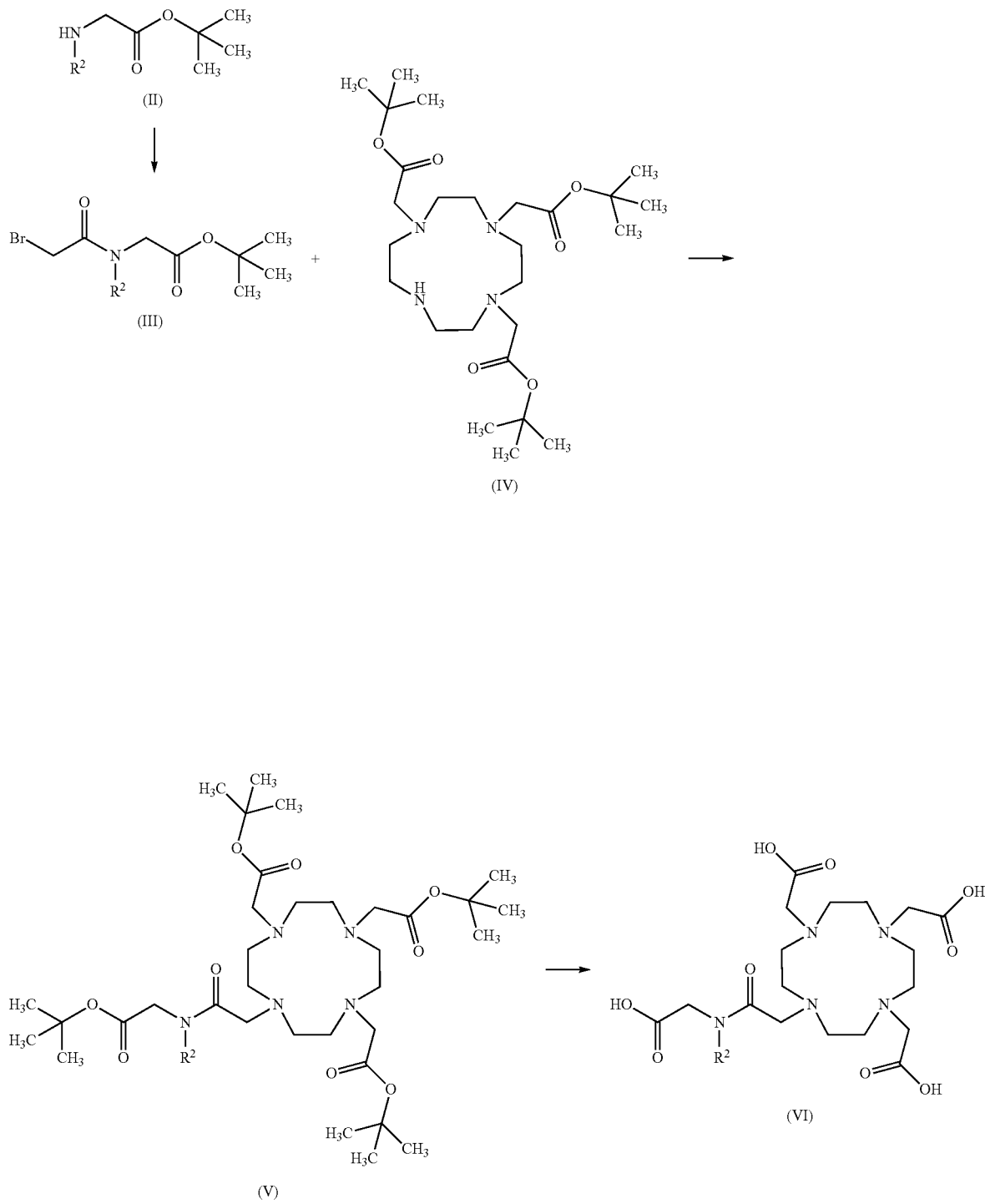
Scheme 1: Route for the preparation of compouds of general formula (VI), wherein $R^2$ has the meaning as given for general formula (I), supra.

Compounds (II) are either commercially available or can be prepared according to procedures available from the public domain, as understandable to the person skilled in the art. Specific examples are described in the Experimental Section.

A compound of general formula (II) is reacted with bromoacetyl bromide in the presence of a base, such as for example N,N-diisopropyl ethylamine, in a solvent such as for example dichloromethane, in a temperature range from −70° C. to 25° C., to yield a compound of general formula (III).

A compound of general formula (III) is reacted with compound (IV), tri-tert-butyl 2,2',2''-(1,4,7,10-tetraazacyclododecane-1,4,7-triyl)triacetate {CAS Registry Number: 122555-91-3; see B. Jagadish et al., THL 52(17), 2058-2061 (2011)}, in the presence of a base, such as for example potassium carbonate, in a solvent such as for example acetonitrile, in a temperature range from 25° C. to 80° C., preferably at 60° C., to yield a compound of general formula (V). Cleavage of the carboxyl-protecting groups of a compound of general formula (V) to yield an intermediate of general formula (VI) can be achieved as described in the textbook Greene and Wuts, Protecting groups in Organic Synthesis, second edition. The deprotection is, for example, performed by dissolving and stirring of a compound of general formula (V) in formic acid in a temperature range from 40° C. to 100° C., preferably at 80° C., to yield a compound of general formula (VI).

A route for the preparation of compounds of general formula (I) is described in Scheme 2

Scheme 2: Route for the preparaion of compounds of general formula (I), wherein $R^1$ and $R^2$ have the meaning as given for general formula (I), supra, and LG represents an activating leaving group, such as for example 4-nitrophenol.

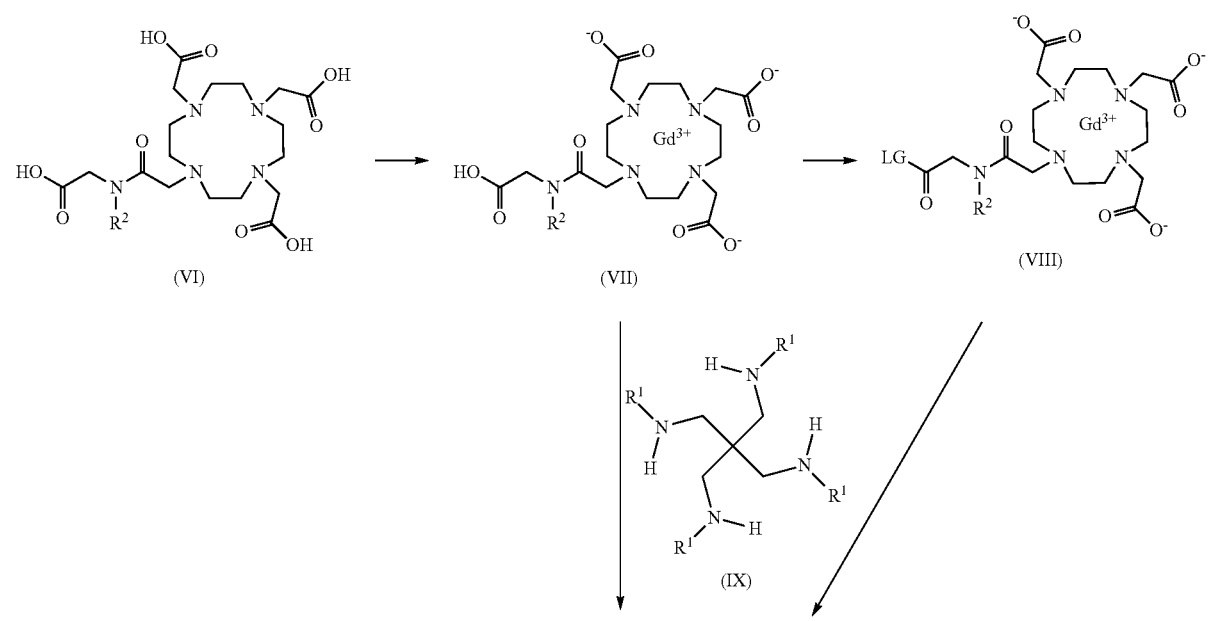

-continued

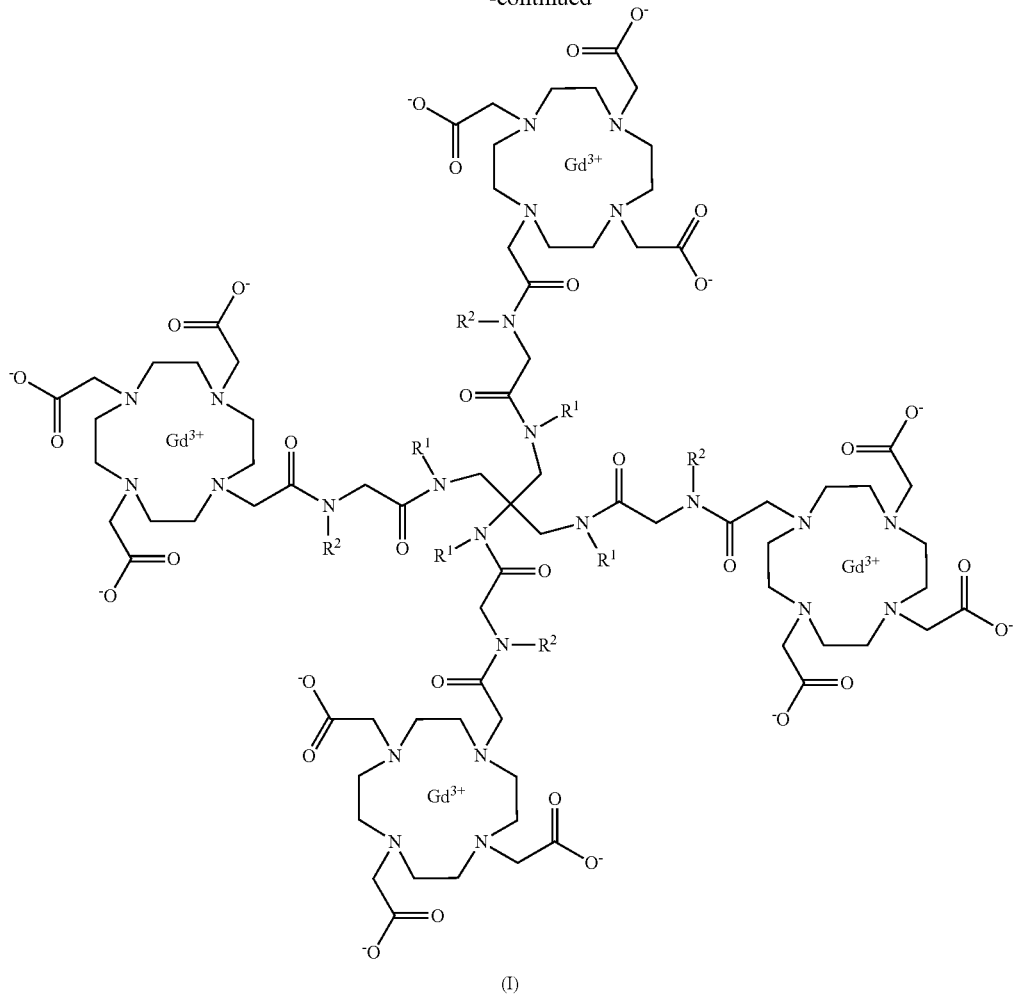

(I)

The complexation of intermediates of general formula (VI) with suitable gadolinium(III) compounds or salts, such as for example gadolinium trioxide, gadolinium triacetate, or hydrates of gadolinium triacetate, gadolinium trichloride, or gadolinium trinitrate, is well known to a person skilled in the art. The intermediates of general formula (VI) are dissolved in water and after adding of suitable gadolinium(III) compounds the resulting mixtures are stirred in a temperature range from room temperature up to 100°, to furnish the compounds of general formula (VII). Intermediates of general formula (VI) are, for example, dissolved in water, gadolinium(III) oxide is added, and the reaction mixture is stirred at 100° C., leading to compounds of general formula (VII).

The intermediates of general formula (VII) can be transformed into activated esters of general formula (VIII) by methods, which are well known to the person skilled in the art and which are described in detail for example by C. A. Montalbetti and V. Falque in Tetrahedron 61 (2005), page 10827-10852. For example, the intermediates of general formula (VII) are dissolved in a solvent such as formamide or THF or mixtures thereof, and are reacted with 4-nitrophenol in the presence of N,N'diisopropyl carbodiimide. The reaction is carried out in a temperature range from −10° C. to room temperature, preferably from 0° C. to 5° C., leading to an activated ester (VIII).

A tetraamine (IX) or a salt thereof (e.g. CAS Registry Numbers: 4742-00-1, 14302-75-1, 69898-47-1, 14259-94-0, 154074-32-5) is reacted with a Gd-complex of the general formula (VIII), which is activated by a leaving group (LG), such as for example pentafluorophenol, 4-nitrophenol, 1-hydroxypyrrolidine-2,5-dione, hydroxybenzotriazole, or 3H-[1,2,3]triazolo[4,5-b]pyridin-3-ol, leading to a compound of the general formula (I). The reaction of a tetraamine (IX) or a salt thereof with the activated Gd-complexes of general formula (VIII) is carried out in a suitable solvent, such as for example dimethyl sulfoxide, N,N-dimethylformamide, pyridine, or a mixture thereof, optionally the reaction is carried out in the presence of a base. Suitable bases are for example trialkylamines, such as for example triethylamine or N,N-diisopropylethylamine. The reaction is carried out at temperatures ranging from room temperature to 100° C., preferably the reaction is carried out at temperatures ranging from 40° C. to 60° C.

Alternatively, the compounds of general formula (I) can be obtained by standard amide coupling reactions of the carboxylic acids of general formula (VII) with the amines of general formula (IX), for example by choosing reaction conditions where activated esters of general formula (VIII) are generated in situ from carboxylic acids of general formula (VII).

In accordance with an embodiment, the present invention also relates to a method of preparing a compound of general formula (I) as defined supra, said method comprising the step of allowing an intermediate compound of general formula (VIII):

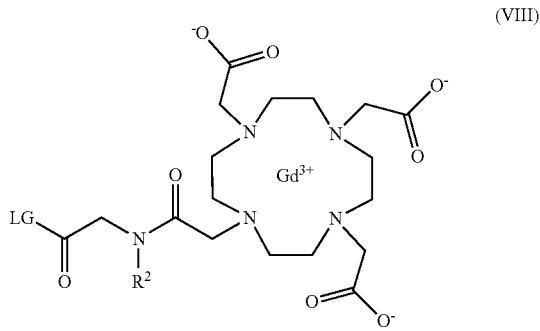

in which R² is as defined for the compound of general formula (I), supra, and LG represents an activating leaving group, such as for example 4-nitrophenol, or a group as defined for the synthesis of the compounds of the general formula (I) supra, to react with an intermediate compound of general formula (IX):

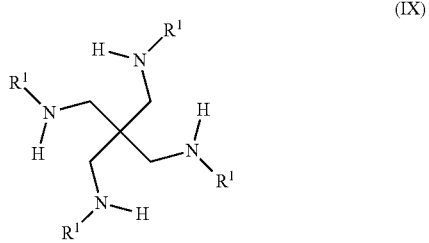

in which R¹ is as defined for the compound of general formula (I), supra, or a salt thereof, thereby giving a compound of general formula (I)

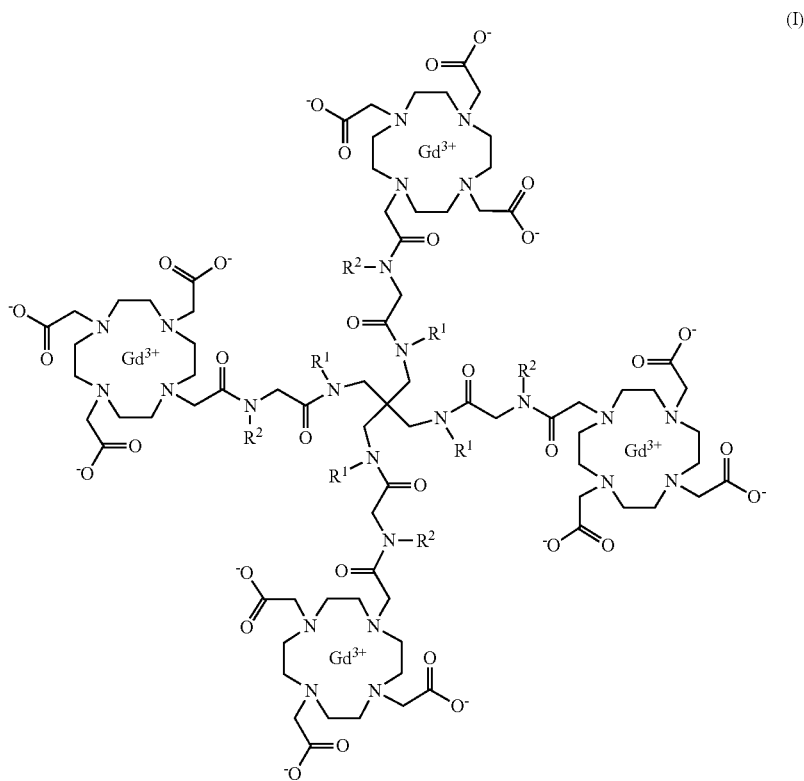

in which $R^1$ and $R^2$ are as defined for the compound of general formula (I) supra.

DESCRIPTION OF THE FIGURES

FIG. 3: Representative MR-Angiograms (maximum intensity projection) for

B (middle): example compound 6 at 25 µmol/kg, compared to

C (right): reference compound 1 (Gadovist) at standard dose (100 µmol/kg), and

A (left): reference compound 1 (Gadovist) at reduced dose (25 µmol/kg).

No qualitative difference in the vascular contrast was found for the example compound 6 at 25 µmol/kg compared to the reference compound 1 at 100 µmol/kg. The vascular contrast at the reduced dose of the reference compound is considerable lower.

Figure 4:
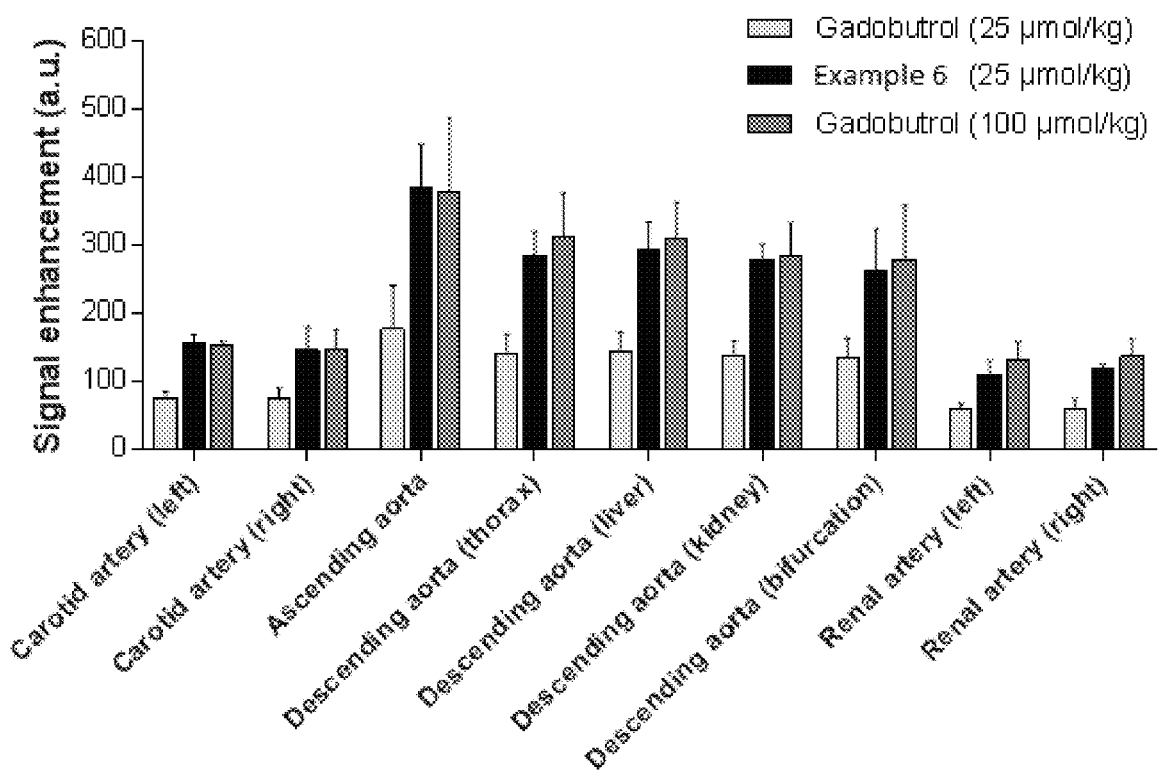

FIG. 4: Signal enhancement at representative vascular regions (mean±standard deviation) for example compound 6 at 25 µmol/kg compared to reference compound 1 (Gadovist) at standard dose (100 µmol/kg) and reduced dose (25 µmol/kg). No significant difference exist between compound 6 compared to the standard dose of the reference compound, while significantly ($p<0.001$) higher signal enhancements were found compared to the reduced dose of the reference compound.

EXPERIMENTAL SECTION

Abbreviations

| | |
|---|---|
| ACN | acetonitrile |
| AUC | area under the curve |
| bw | body weight |
| $CDCl_3$ | chloroform-d |
| CPMG | Carr-Purcell-Meiboom-Gill (MRI sequence) |
| $C_{Gd}$ | concentration of the compound normalized to the Gadolinium |
| $Cl_{tot}$ | total clearance |
| d | day(s) |
| $D_2O$ | deuterium oxide |
| DAD | diode array detector |
| DCM | dichloromethane |
| DMSO | dimethylsulfoxide |
| DMSO-$d_6$ | deuterated dimethylsulfoxide |
| ECCM | extracellular contrast media |
| EI | electron ionisation |
| ELSD | evaporative light scattering detector |
| ESI | electrospray ionisation |
| FBS | fetal bovine serum |
| h | hour |
| HCOOH | formic acid |
| HPLC | high performance liquid chromatography |
| HU | Hounsfield units |
| IR | inversion recovery |
| kDa | kilo Dalton |
| LCMS | liquid chromatography-mass spectroscopy |
| ICP-MS | inductively coupled plasma mass spectrometry |
| MRI | magnetic resonance imaging |
| MRT | mean residence time |
| MS | mass spectrometry |
| m | multiplet |
| min | minute(s) |
| NMR | nuclear magnetic resonance spectroscopy: chemical shifts (δ) are given in ppm. |
| q | quartet |
| $r_i$ | (where i = 1, 2) relaxivities in L mmol$^{-1}$ s$^{-1}$ |
| $R_t$ | retention time |
| s | singlet |
| RC | reference compound |
| $R_i$ | (where i = 1, 2) relaxation rates (1/$T_{1,2}$) |
| $R_{i(0)}$ | relaxation rate of the respective solvent |
| $T_{1,2}$ | relaxation time |
| T | Tesla |
| t | triplet |
| $t_{1/2}$ α | plasma half-life, compartment V1 |
| $t_{1/2}$ β | plasma half-life, compartment V2 |
| $t_{1/2}$ γ | plasma half-life, compartment V3 |
| TFA | trifluoroacetic acid |
| THF | tetrahydrofuran |
| TI | inversion time |
| UPLC | ultra performance liquid chromatography |
| V1 + V2 | volume, compartments V1 + V2 |
| $V_c$ (V1) | volume, central compartment V1 |
| $V_{d,ss}$ | volume of distribution at steady state |

Materials and Instrumentation

The chemicals used for the synthetic work were of reagent grade quality and were used as obtained.

All reagents, for which the synthesis is not described in the experimental section, are either commercially available, or are known compounds or may be formed from known compounds by known methods by a person skilled in the art.

$^1$H-NMR spectra were measured in $CDCl_3$, $D_2O$ or DMSO-$d_6$, respectively (room temperature, Bruker Avance 400 spectrometer, resonance frequency: 400.20 MHz for $^1$H or Bruker Avance 300 spectrometer, resonance frequency: 300.13 MHz for $^1$H. Chemical shifts are given in ppm relative to sodium (trimethylsilyl)propionate-$d_4$ ($D_2O$) or tetramethylsilane (DMSO-$d_6$) as external standards (δ=0 ppm).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

Examples were analyzed and characterized by the following HPLC based analytical methods to determine characteristic retention time and mass spectrum:

Method 1: UPLC (ACN-HCOOH):

Instrument: Waters Acquity UPLC-MS SQD 3001; column: Acquity UPLC BEH C18 1.7 μm, 50×2.1 mm; eluent A: water+0.1% formic acid, eluent B: acetonitrile; gradient: 0-1.6 min 1-99% B, 1.6-2.0 min 99% B; flow 0.8 mL/min; temperature: 60° C.; injection: 2 μl; DAD scan: 210-400 nm; ELSD.

Method 2: LC-MS:

Instrument: Agilent 1290 UHPLCMS Tof; column: BEH C 18 (Waters) 1.7 μm, 50×2.1 mm; eluent A: water+0.05 vol-% formic acid (99%), eluent B: acetonitrile+0.05% formic acid; gradient: 0-1.7 min 98-10% A, 1.7-2.0 min 10% A, 2.0-2.5 min 10-98% A, flow 1.2 mL/min; temperature: 60° C.; DAD scan: 210-400 nm.

EXAMPLE COMPOUNDS

Example 1

Tetragadolinium [4,10-bis(carboxylatomethyl)-7-{3,13-dimethyl-8,8-bis({[(methyl{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate

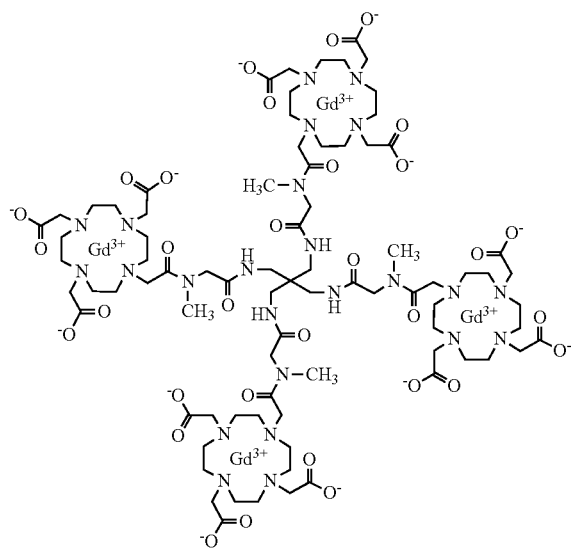

Example 1-1

Tert-butyl N-(bromoacetyl)-N-methylglycinate

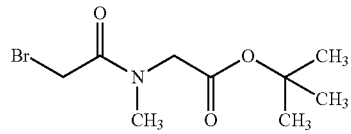

A stirred suspension of 30.00 g (165.1 mmol, 1 eq.) tert-butyl N-methylglycinate hydrochloride (1:1) and 44.82 g (346.8 mmol, 2.1 eq.) N,N-diisopropyl ethylamine in 250 ml dichloromethane was cooled to −70° C. After slow addition of 35.67 g (176.7 mmol, 1.07 eq.) bromoacetyl bromide, dissolved in 70 ml dichloromethane, the reaction mixture was warmed over night to room temperature. The organic layer was washed twice with 0.1 M aqueous hydrochloric acid, with saturated aqueous sodium bicarbonate solution and with half saturated sodium chloride solution. After drying over sodium sulfate, the solvent was evaporated under reduced pressure yielding 34.62 g (79%, 130.1 mmol) of the title compound.

$^1$H-NMR (400 MHz, DMSO-$d_6$): δ=1.36-1.47 (m, 9H), 2.80-3.08 (m, 3H), 3.94-4.47 (m, 4H) ppm.

LC-MS (ES$^+$): m/z=266.1 and 268.1 (M+H)$^+$; R$_t$=0.91 and 0.94 min.

Example 1-2

Tert-butyl N-methyl-N-{[4,7,10-tris(2-tert-butoxy-2-oxoethyl)-1,4,7,10-tetraazacyclo-dodecan-1-yl]acetyl}glycinate

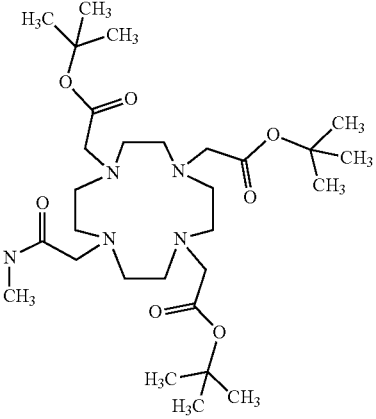

To a solution of 6.98 g (13.56 mmol, 1 eq.) tri-tert-butyl 2,2′,2″-(1,4,7,10-tetraazacyclododecane-1,4,7-triyl)triacetate {CAS No. [122555-91-3]; see B. Jagadish et al., THL 52(17), 2058-2061 (2011)} in 175 ml acetonitrile were added 5.62 g (40.69 mmol, 3 eq.) potassium carbonate and 3.80 g (13.56 mmol, 1 eq.) tert-butyl N-(bromoacetyl)-N-methylglycinate (example 1-1). The resulting reaction mixture was stirred over night at 60° C. After filtration, the solution was evaporated under reduced pressure to dryness. The residue was purified by chromatography yielding 6.63 g (70%, 9.48 mmol) of the title compound.

$^1$H-NMR (400 MHz, CDCl$_3$): δ=1.38-1.50 (m, 36H), 1.90-4.00 (m, 29H) ppm.
LC-MS (ES$^+$): m/z=700.5 (M+H)$^+$; R$_t$=1.01 min.

Example 1-3

N-methyl-N-{[4,7,10-tris(carboxymethyl)-1,4,7,10-tetraazacyclododecan-1-yl]acetyl}-glycine

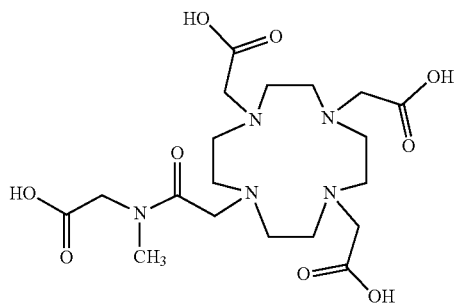 [SMILES: CN(CC(=O)O)C(=O)CN1CCN(CC(=O)O)CCN(CC(=O)O)CCN(CC(=O)O)CC1]

12.29 g (17.56 mmol) Tert-butyl N-methyl-N-{[4,7,10-tris(2-tert-butoxy-2-oxoethyl)-1,4,7,10-tetraazacyclododecan-1-yl]acetyl}glycinate (example 1-2) were dissolved in 300 ml formic acid. The solution was stirred for two hours at 80° C. After evaporation under reduced pressure, the residue was dissolved in 600 ml water and was washed repeatedly with dichloromethane. The aqueous layer was dried by lyophilization yielding 8.04 g (96%, 16.90 mmol) of the title compound.
$^1$H-NMR (400 MHz, D$_2$O): δ=2.81-2.94 (m, 3H), 2.95-4.05 (m, 26H) ppm.
LC-MS (ES$^+$): m/z=476.2 (M+H)$^+$; R$_t$=0.22 min.

Example 1-4

Gadolinium 2,2',2''-(10-{2-[(carboxymethyl)(methyl)amino]-2-oxoethyl}-1,4,7,10-tetra-azacyclododecane-1,4,7-triyl)triacetate

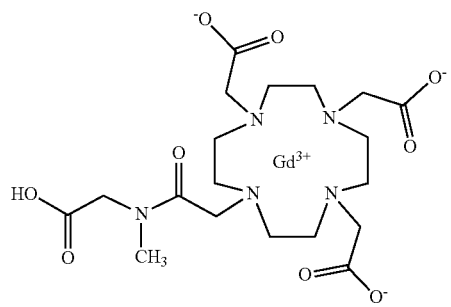

2.03 g (4.28 mmol, 1 eq.) N-Methyl-N-{[4,7,10-tris(carboxymethyl)-1,4,7,10-tetraazacyclodo-decan-1-yl]acetyl}glycine (example 1-3) were dissolved in 42 ml water. 697.8 mg (1.925 mmol, 0.45 eq.) Gadolinium(III) oxide were added and the resulting reaction mixture was stirred for 7.5 hours at 100° C. After cooling to room temperature, 260 mg of activated charcoal were added and the black suspension was stirred over night at room temperature. The filtrated solution was dried by lyophilization. The residue was dissolved in 50 ml water and the pH was adjusted to 2.4 by adding Dowex 50 W-X2 (H$^+$ form). The final product was isolated by lyophilization yielding 2.09 g (78%, 3.32 mmol).
LC-MS (ES$^+$): m/z=630.0 (M+H)$^+$; R$_t$=0.25 and 0.28 min.

Example 1-5

Gadolinium 2,2',2''-[10-(2-{methyl[2-(4-nitrophenoxy)-2-oxoethyl]amino}-2-oxoethyl)-1,4,7,10-tetraazacyclododecane-1,4,7-triyl]triacetate

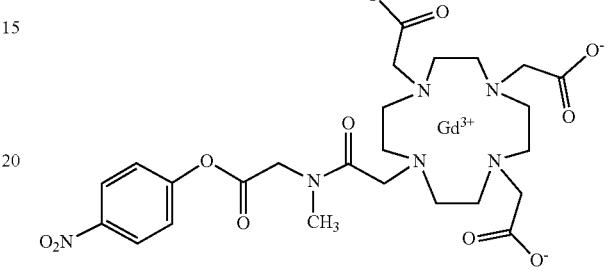

2.09 g (3.32 mmol, 1 eq.) Gadolinium 2,2',2''-(10-{2-[(carboxymethyl)(methyl)amino]-2-oxoethyl}-1,4,7,10-tetraazacyclododecane-1,4,7-triyl)triacetate (example 1-4) and 922.0 mg (6.64 mmol, 2 eq.) 4-nitrophenol were dissolved in 6 ml formamide and 4 ml THF. The solution was cooled to 0° C. and 628.0 mg (4.98 mmol, 1.5 eq.) N,N'diisopropyl carbodiimide, dissolved in 280 μl THF, were slowly added. The resulting reaction mixture was stirred for 5 hours at 0-5° C. Dropwise addition of 45 ml THF precipitated the desired product. 2.47 g (94%, 3.13 mmol) of title compound were isolated by filtration.
LC-MS (ES$^+$): m/z=752.5 (M+H)$^+$; R$_t$=0.59 and 0.62 min.

Example 1

Tetragadolinium [4,10-bis(carboxylatomethyl)-7-{3,13-dimethyl-8,8-bis({[(methyl{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate 30.9 mg (0.111 mmol, 1 eq.) 2,2-Bis(ammoniomethyl)propane-1,3-diaminium tetrachloride [see W. Hayes et al., Tetrahedron 59 (2003), 7983-7996 and S. Dutta et al., Inorg. Chem. Communications 13(9), 1074-1080 (2010)] were dissolved in 16 mL DMSO. After addition of 115.0 mg (0.888 mmol, 8 eq.) N,N-diisopropylethylamine and 1.0 g (1.332 mmol, 12 eq.) gadolinium 2,2',2''-[10-(2-{methyl[2-(4-nitrophenoxy)-2-oxoethyl]amino}-2-oxoethyl)-1,4,7,10-tetraazacyclododecane-1,4,7-triyl]triacetate (example 1-5), the resulting reaction mixture was stirred and heated for 8 hours at 50° C. The cooled solution was concentrated under reduced pressure. The concentrate was poured under stirring in an excess of ethyl acetate, the formed precipitate was filtered off and was dried in vacuo. The solid was dissolved in 30 ml 0.01 M aqueous sodium hydroxide solution and the pH was adjusted to 12 by adding of 1 M aqueous sodium hydroxide solution. After stirring for 1 hour at pH=12, the pH was adjusted to 7 by adding 1 M aqueous hydrochloric acid. The resulting solution was filtered, was ultrafiltrated with water using a 1 kDa membrane and the final retentate was lyophilized. The crude product was purified by RP-chromatography yielding 219 mg (77%, 0.085 mmol) of the title compound.

UPLC (ACN-HCOOH): $R_t$=0.39 min.

MS (ES$^+$): m/z (z=2)=1290.3 (M+H)$^{2+}$, m/z (z=3)=860.8 (M+H)$^{3+}$, m/z (z=4)=646.5 (M+H)$^{4+}$.

Example 2

Tetragadolinium [4,10-bis(carboxylatomethyl)-7-{3,13-diethyl-8,8-bis({[(ethyl{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraaza-cyclododecan-1-yl]-3,6,10,13-tetraazapentadec-1-yl}-1,4,7,10-tetraazacyclododecan-1-yl]acetate

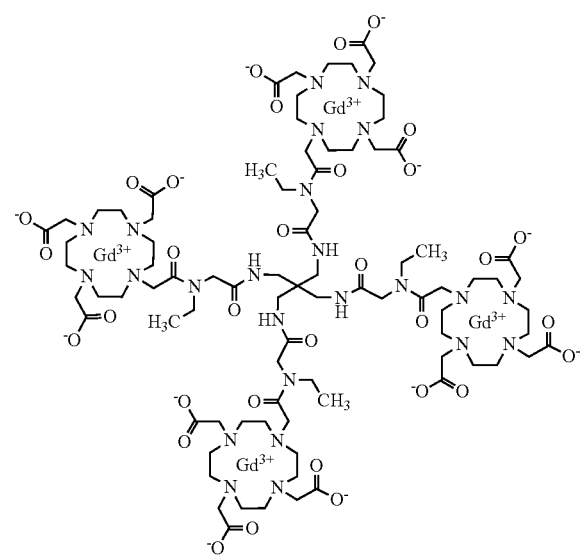

Example 2-1

Tert-butyl N-ethylglycinate

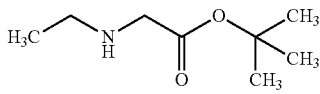

31.21 g (160.0 mmol) Tert-butyl bromoacetate, dissolved in 160 ml THF, were dropped in 800 ml of a 2 Methanamine solution in THF. The reaction mixture was stirred over night at room temperature. THF was distilled off, the residue was dissolved in dichloromethane and the organic layer was washed twice with 0.1 M aqueous sodium hydroxide solution, was dried over sodium sulfate and was evaporated yielding 23.4 g (92%, 147.0 mmol) of the title compound.

$^1$H-NMR (400 MHz, CDCl$_3$): δ=1.11 (t, 3H), 1.46 (s, 9H), 1.59 (s, 1H), 2.63 (q, 2H), 3.29 (s, 2H) ppm.

Example 2-2

Tert-butyl N-(bromoacetyl)-N-ethylglycinate

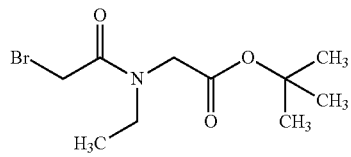

The compound was synthesized according to the procedure described in example 1-1 starting from 23.20 g (145.7 mmol, 1 eq.) tert-butyl N-ethylglycinate (example 2-1), 20.15 g (155.9 mmol, 1.07 eq.) N,N-diisopropyl ethylamine, and 31.47 g (155.9 mmol, 1.07 eq.) bromoacetyl bromide yielding 40.6 g (100%, 145 mmol).

$^1$H-NMR (400 MHz, CDCl$_3$): δ=1.08-1.29 (m, 3H), 1.42-1.53 (m, 9H), 3.41-3.53 (m, 2H), 3.77-4.02 (m, 4H) ppm.

LC-MS (ES$^+$): m/z=280.0 and 282.0 (M+H)$^+$; $R_t$=1.01 min.

Example 2-3

Tert-butyl N-ethyl-N-{[4,7,10-tris(2-tert-butoxy-2-oxoethyl)-1,4,7,10-tetraazacyclododecan-1-yl]acetyl}glycinate

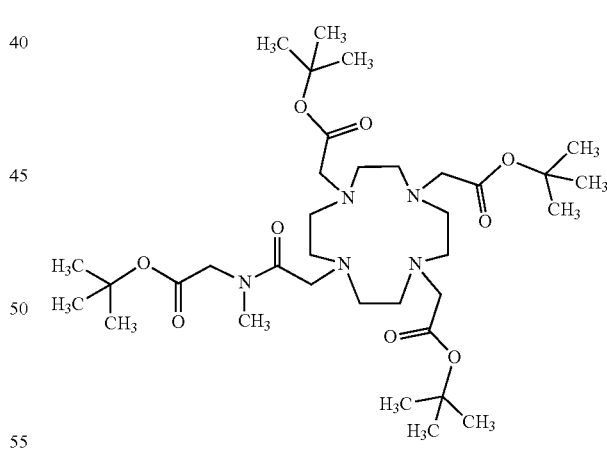

The compound was synthesized according to the procedure described in example 1-2 starting from 18.00 g (34.97 mmol, 1 eq.) tri-tert-butyl 2,2',2''-(1,4,7,10-tetraazacyclododecane-1,4,7-triyl)triacetate, 14.50 g (104.91 mmol, 3 eq.) potassium carbonate, and 9.80 g (34.97 mmol, 1 eq.) tert-butyl N-(bromoacetyl)-N-ethylglycinate (example 2-2) yielding 24.8 g (100%, 34.8 mmol).

$^1$H-NMR (400 MHz, CDCl$_3$): δ=1.02-1.23 (m, 3H), 1.39-1.54 (m, 36H), 1.65-4.90 (m, 28H) ppm.

LC-MS (ES$^+$): m/z=714.6 (M+H)$^+$; $R_t$=1.01 min.

Example 2-4

N-ethyl-N-{[4,7,10-tris(carboxymethyl)-1,4,7,10-tetraazacyclododecan-1-yl]acetyl}glycine

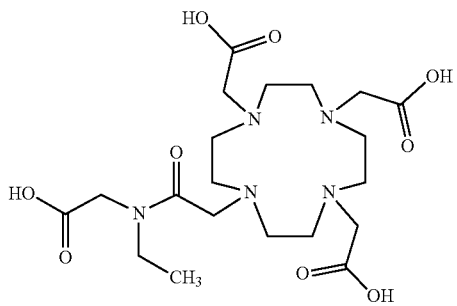 [SMILES: CCN(CC(=O)O)C(=O)CN1CCN(CC(=O)O)CCN(CC(=O)O)CCN(CC(=O)O)CC1]

The compound was synthesized according to the procedure described in example 1-3 starting from 24.83 g (34.78 mmol) tert-butyl N-ethyl-N-{[4,7,10-tris(2-tert-butoxy-2-oxoethyl)-1,4,7,10-tetraazacyclododecan-1-yl]acetyl}glycinate (example 2-3) in 515 ml formic acid yielding 18.33 g (108%, 37.44 mmol).

$^1$H-NMR (400 MHz, D$_2$O): δ=0.93-1.22 (m, 3H), 2.90-4.15 (m, 28H) ppm.

LC-MS (ES$^+$): m/z=490.2 (M+H)$^+$; R$_t$=0.29 min.

Example 2-5

Gadolinium 2,2',2''-(10-{2-[(carboxymethyl)(ethyl)amino]-2-oxoethyl}-1,4,7,10-tetra-azacyclododecane-1,4,7-triyl)triacetate

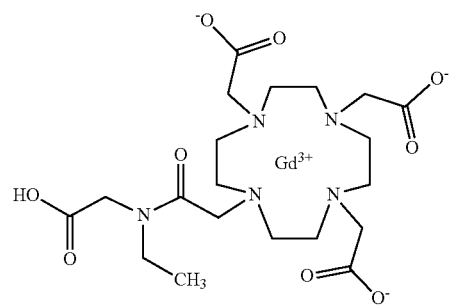

The compound was synthesized according to the procedure described in example 1-4 starting from 17.02 g (34.77 mmol, 1 eq.) N-ethyl-N-{[4,7,10-tris(carboxymethyl)-1,4,7, 10-tetraazacyclododecan-1-yl]acetyl}glycine (example 2-4) and 5.67 g (15.65 mmol, 0.45 eq.) gadolinium(III) oxide yielding 22.90 g (102%, 35.57 mmol).

LC-MS (ES$^+$): m/z=645.1 (M+H)$^+$; R$_t$=0.31 and 0.39 min.

Example 2-6

Gadolinium 2,2',2''-[10-(2-{ethyl[2-(4-nitrophenoxy)-2-oxoethyl]amino}-2-oxoethyl)-1,4,7,10-tetraazacyclododecane-1,4,7-triyl]triacetate

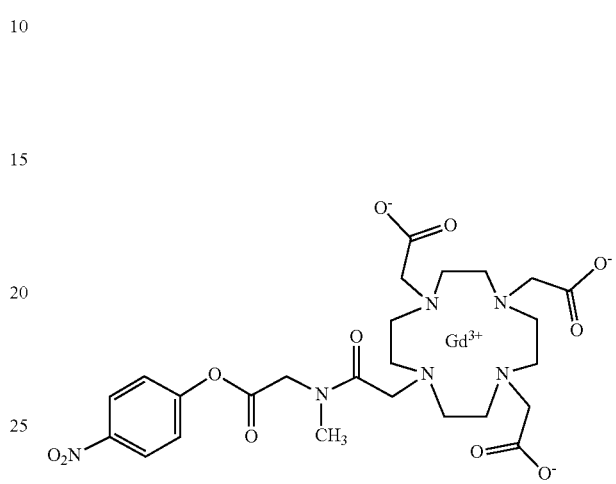

The compound was synthesized according to the procedure described in example 1-5 starting from 4.25 g (6.60 mmol, 1 eq.) gadolinium 2,2',2''-(10-{2-[(carboxymethyl)(ethyl)-amino]-2-oxoethyl}-1,4,7,10-tetraazacyclododecane-1,4,7-triyl)triacetate (example 2-5), 1.84 g (13.20 mmol, 2 eq.) 4-nitrophenol, and 1.25 g (9.90 mmol, 1.5 eq.) N,N'diisopropyl carbodiimide yielding 5.05 g (100%, 6.6 mmol).

LC-MS (ES$^+$): m/z=766.0 (M+H)$^+$; R$_t$=0.63 and 0.65 min.

Example 2

Tetragadolinium [4,10-bis(carboxylatomethyl)-7-{3,13-diethyl-8,8-bis({[(ethyl{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraaza-cyclododecan-1-yl]-3,6,10,13-tetraazapentadec-1-yl}-1,4,7,10-tetraazacyclododecan-1-yl]acetate The compound was synthesized according to the procedure described in example 1 starting from 151.5 mg (0.545 mmol, 1 eq.) 2,2-bis(ammoniomethyl)propane-1,3-diaminium tetrachloride, 563.0 mg (4.36 mmol, 8 eq.) N,N-diisopropyl ethylamine, and 5.00 g (6.54 mmol, 12 eq.) gadolinium 2,2',2''-[10-(2-{ethyl[2-(4-nitrophenoxy)-2-oxoethyl]amino}-2-oxoethyl)-1,4,7,10-tetraazacyclododecane-1,4,7-triyl]triacetate (example 2-6) yielding 413 mg (29%, 0.16 mmol).

UPLC (ACN-HCOOH): R$_t$=0.41 min.

MS (ES$^+$): m/z (z=2)=1318.0 (M+H)$^{2+}$, m/z (z=3)=878.9 (M+H)$^{3+}$.

Example 3

Tetragadolinium {4,10-bis(carboxylatomethyl)-7-[15-(2-methoxyethyl)-10,10-bis[({[(2-methoxyethyl){[4,7,10-tris(carboxylatomethyl)-1,4,7,10-tetraazacyclododecan-1-yl]-acetyl}amino]acetyl}amino)methyl]-7,13,16-trioxo-5-{[4,7,10-tris(carboxylatomethyl)-1,4,7,10-tetraazacyclododecan-1-yl]acetyl}-2-oxa-5,8,12,15-tetraazaheptadecan-17-yl]-1,4,7,10-tetraazacyclododecan-1-yl}acetate

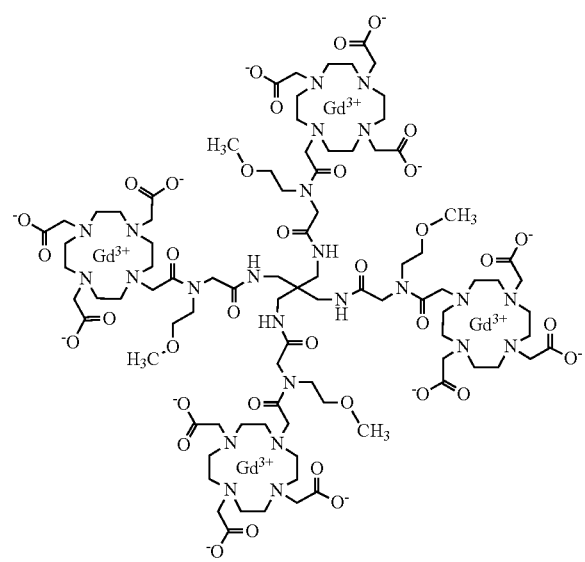

Example 3-1

Tert-butyl N-(bromoacetyl)-N-(2-methoxyethyl)glycinate

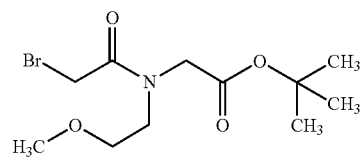

The compound was synthesized according to the procedure described in example 1-1 starting from 3.73 g (19.71 mmol, 1 eq.) tert-butyl N-(2-methoxyethyl)glycinate [see J. T. Suh et al., J. Med. Chem. 1985(28), 57-66], 2.73 g (21.09 mmol, 1.07 eq.) N,N-diisopropyl ethylamine, and 4.26 g (21.09 mmol, 1.07 eq.) bromoacetyl bromide yielding 6.10 g (100%, 19.67 mmol).

$^1$H-NMR (400 MHz, CDCl$_3$): δ=1.43-1.52 (m, 9H), 3.26-3.36 (m, 3H), 3.49-3.64 (m, 4H), 3.78-4.00 (m, 2H), 4.01-4.16 (m, 2H) ppm.

LC-MS (ES$^+$): m/z=310.0 and 312.0 (M+H)$^+$; R$_t$=1.04 min.

Example 3-2

Tert-butyl N-(2-methoxyethyl)-N-{[4,7,10-tris(2-tert-butoxy-2-oxoethyl)-1,4,7,10-tetra-azacyclododecan-1-yl]acetyl}glycinate

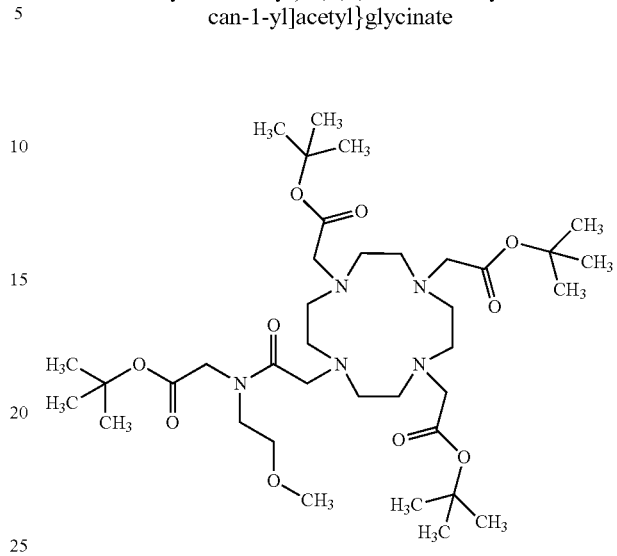

The compound was synthesized according to the procedure described in example 1-2 starting from 4.33 g (8.41 mmol, 1 eq.) tri-tert-butyl 2,2',2''-(1,4,7,10-tetraazacyclododecane-1,4,7-triyl)triacetate, 3.49 g (25.24 mmol, 3 eq.) potassium carbonate, and 2.61 g (8.41 mmol, 1 eq.) tert-butyl N-(bromoacetyl)-N-(2-methoxyethyl)glycinate (example 3-1) yielding 5.81 g (84%, 7.04 mmol).

$^1$H-NMR (400 MHz, CDCl$_3$): δ=1.36-1.55 (m, 36H), 1.89-4.95 (m, 33H) ppm.

LC-MS (ES$^+$): m/z=744.5 (M+H)$^+$; R$_t$=1.09 min.

Example 3-3

N-(2-methoxyethyl)-N-{[4,7,10-tris(carboxymethyl)-1,4,7,10-tetraazacyclododecan-1-yl]-acetyl}glycine

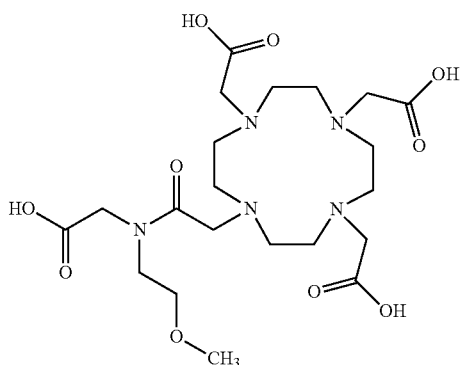

The compound was synthesized according to the procedure described in example 1-3 starting from 5.80 g (7.80 mmol) tert-butyl N-(2-methoxyethyl)-N-{[4,7,10-tris(2-tert-butoxy-2-oxoethyl)-1,4,7,10-tetraazacyclododecan-1-yl]acetyl}glycinate (example 3-2) in 120 ml formic acid yielding 4.19 g (93%, 7.26 mmol).

$^1$H-NMR (400 MHz, D$_2$O): δ=2.70-3.98 (m, 31H), 3.99-4.07 (m, 2H) ppm.

LC-MS (ES$^+$): m/z=520.2 (M+H)$^+$; R$_t$=0.32 min.

Example 3-4

Gadolinium 2,2',2"-(10-{2-[(carboxymethyl)(2-methoxyethyl)amino]-2-oxoethyl}-1,4,7,10-tetraazacyclododecane-1,4,7-triyl)triacetate

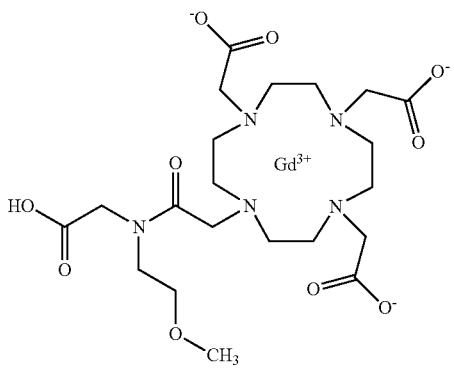

The compound was synthesized according to the procedure described in example 1-4 starting from 4.19 g (8.07 mmol, 1 eq.) N-(2-methoxyethyl)-N-{[4,7,10-tris(carboxymethyl)-1,4,7,10-tetraazacyclododecan-1-yl]acetyl}glycine (example 3-3) and 1.32 g (3.63 mmol, 0.45 eq.) gadolinium(III) oxide yielding 5.09 g (84%, 6.80 mmol).

LC-MS (ES$^+$): m/z=675.1 (M+H)$^+$; R$_t$=0.37 and 0.42 min.

Example 3-5

Gadolinium 2,2',2"-[10-(2-{(2-methoxyethyl)[2-(4-nitrophenoxy)-2-oxoethyl]amino}-2-oxoethyl)-1,4,7,10-tetraazacyclododecane-1,4,7-triyl]triacetate

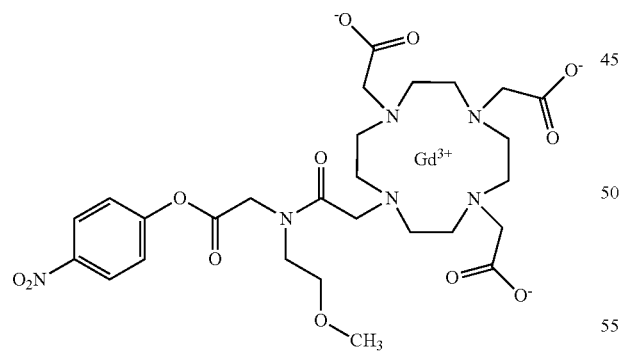

The compound was synthesized according to the procedure described in example 1-5 starting from 4.57 g (6.78 mmol, 1 eq.) gadolinium 2,2',2"-(10-{2-[(carboxymethyl)(2-methoxyethyl)amino]-2-oxoethyl}-1,4,7,10-tetraazacyclododecane-1,4,7-triyl)triacetate (example 3-4), 1.89 g (13.57 mmol, 2 eq.) 4-nitrophenol, and 1.28 g (10.17 mmol, 1.5 eq.) N,N'diisopropyl carbodiimide yielding 5.26 g (97.5%, 6.62 mmol).

LC-MS (ES$^+$): m/z=796.1 (M+H)$^+$; R$_t$=0.65 and 0.67 min.

Example 3

Tetragadolinium {4,10-bis(carboxylatomethyl)-7-[15-(2-methoxyethyl)-10,10-bis[({[(2-methoxyethyl){[4,7,10-tris(carboxylatomethyl)-1,4,7,10-tetraazacyclododecan-1-yl]-acetyl}amino]acetyl}amino)methyl]-7,13,16-trioxo-5-{[4,7,10-tris(carboxylatomethyl)-1,4,7,10-tetraazacyclododecan-1-yl]acetyl}-2-oxa-5,8,12,15-tetraazaheptadecan-17-yl]-1,4,7,10-tetraazacyclododecan-1-yl}acetate The compound was synthesized according to the procedure described in example 1 starting from 169.1 mg (0.61 mmol, 1 eq.) 2,2-bis(ammoniomethyl)propane-1,3-diaminium tetrachloride, 629.0 mg (4.86 mmol, 8 eq.) N,N-diisopropyl ethylamine, and 5.80 g (7.30 mmol, 12 eq.) gadolinium 2,2',2"-[10-(2-{(2-methoxyethyl)[2-(4-nitrophenoxy)-2-oxoethyl]amino}-2-oxoethyl)-1,4,7,10-tetraazacyclododecane-1,4,7-triyl]triacetate (example 3-5) yielding 462 mg (39%, 0.17 mmol).

UPLC (ACN-HCOOH): R$_t$=0.44 min.

MS (ES$^+$): m/z (z=2)=1377.7 (M+H)$^{2+}$, m/z (z=3)=919.7 (M+H)$^{3+}$.

Example 4

Tetragadolinium {4,10-bis(carboxylatomethyl)-7-[16-(2-ethoxyethyl)-11,11-bis[({[(2-ethoxyethyl){[4,7,10-tris(carboxylatomethyl)-1,4,7,10-tetraazacyclododecan-1-yl]-acetyl}amino]acetyl}amino)methyl]-8,14,17-trioxo-6-{[4,7,10-tris(carboxylatomethyl)-1,4,7,10-tetraazacyclododecan-1-yl]acetyl}-3-oxa-6,9,13,16-tetraazaoctadecan-18-yl]-1,4,7,10-tetraazacyclododecan-1-yl}acetate

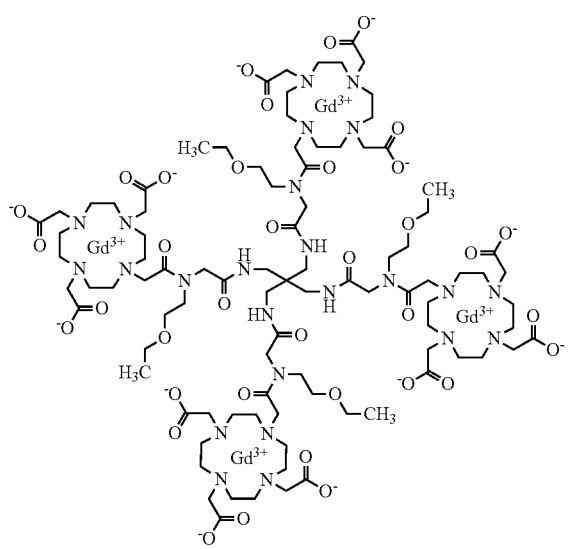

Example 4-1

Tert-butyl N-(2-ethoxyethyl)glycinate

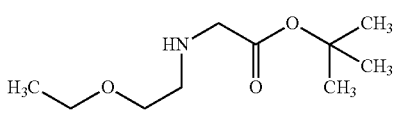

The compound was synthesized according to the procedure described in example 2-1 starting from 8.00 g (89.75 mmol, 10 eq.) 2-ethoxyethanamine and 1.75 g (8.98 mmol, 1 eq.) tert-butyl bromoacetate yielding 1.84 g (91%, 8.15 mmol).

$^1$H-NMR (400 MHz, CDCl$_3$): δ=1.20 (t, 3H), 1.46 (s, 9H), 1.95 (s, 1H), 2.78 (t, 2H), 3.33 (s, 2H), 3.50 (q, 2H), 3.53 (t, 2H) ppm.

Example 4-2

Tert-butyl N-(bromoacetyl)-N-(2-ethoxyethyl)glycinate

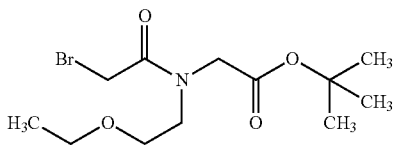 [SMILES: CCOCCN(CC(=O)OC(C)(C)C)C(=O)CBr]

The compound was synthesized according to the procedure described in example 1-1 starting from 1.80 g (8.86 mmol, 1 eq.) tert-butyl N-(2-ethoxyethyl)glycinate (example 4-1), 1.23 g (9.47 mmol, 1.07 eq.) N,N-diisopropyl ethylamine, and 1.91 g (9.47 mmol, 1.07 eq.) bromoacetyl bromide yielding 2.94 g (102%, 9.07 mmol).

$^1$H-NMR (400 MHz, CDCl$_3$): δ=1.13-1.21 (m, 3H), 1.43-1.51 (m, 9H), 3.42-3.52 (m, 2H), 3.53-3.64 (m, 4H), 3.76-4.20 (m, 4H) ppm.

LC-MS (ES$^+$): m/z=324.0 and 326.0 (M+H)$^+$; R$_t$=1.14 min.

Example 4-3

Tert-butyl N-(2-ethoxyethyl)-N-{[4,7,10-tris(2-tert-butoxy-2-oxoethyl)-1,4,7,10-tetraaza-cyclododecan-1-yl]acetyl}glycinate

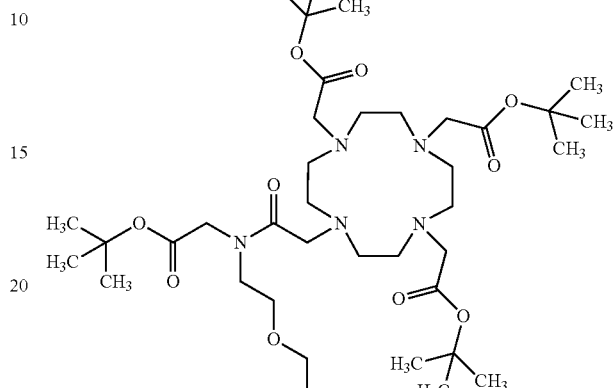

The compound was synthesized according to the procedure described in example 1-2 starting from 4.60 g (8.94 mmol, 1 eq.) tri-tert-butyl 2,2',2''-(1,4,7,10-tetraazacyclododecane-1,4,7-triyl)triacetate, 3.71 g (26.83 mmol, 3 eq.) potassium carbonate, and 2.90 g (8.94 mmol, 1 eq.) tert-butyl N-(bromoacetyl)-N-(2-ethoxyethyl)glycinate (example 4-2) yielding 6.04 g (89%, 7.97 mmol).

$^1$H-NMR (400 MHz, CDCl$_3$): δ=1.11-1.22 (m, 3H), 1.34-1.55 (m, 36H), 1.66-5.00 (m, 32H) ppm.

LC-MS (ES$^+$): m/z=758.8 (M+H)$^+$; R$_t$=1.02 min.

Example 4-4

N-(2-ethoxyethyl)-N-{[4,7,10-tris(carboxymethyl)-1,4,7,10-tetraazacyclododecan-1-yl]-acetyl}glycine

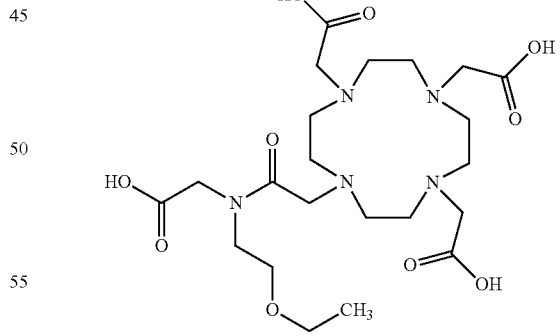

The compound was synthesized according to the procedure described in example 1-3 starting from 6.04 g (7.97 mmol) tert-butyl-(2-ethoxyethyl)-N-{[4,7,10-tris(2-tert-butoxy-2-oxoethyl)-1,4,7,10-tetraazacyclododecan-1-yl]acetyl}glycinate (example 4-3) in 125 ml formic acid yielding 4.49 g (106%, 8.41 mmol).

$^1$H-NMR (400 MHz, D$_2$O): δ=0.99-1.09 (m, 3H), 2.64-4.45 (m, 32H) ppm.

LC-MS (ES$^+$): m/z=534.2 (M+H)$^+$; R$_t$=0.41 min.

Example 4-5

Gadolinium 2,2',2''-(10-{2-[(carboxymethyl)(2-ethoxyethyl)amino]-2-oxoethyl}-1,4,7,10-tetraazacyclododecane-1,4,7-triyl)triacetate

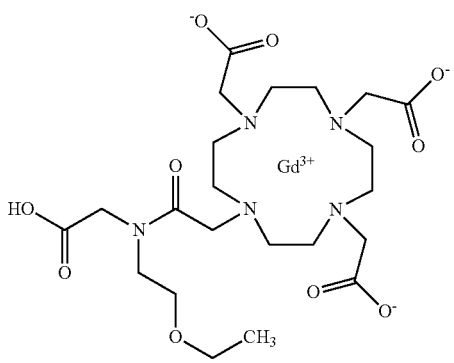

The compound was synthesized according to the procedure described in example 1-4 starting from 4.48 g (8.40 mmol, 1 eq.) N-(2-ethoxyethyl)-N-{[4,7,10-tris(carboxymethyl)-1,4,7,10-tetraazacyclododecan-1-yl]acetyl}glycine (example 4-4) and 1.37 g (3.78 mmol, 0.45 eq.) gadolinium (III) oxide yielding 5.56 g (96%, 8.08 mmol).

LC-MS (ES$^+$): m/z=689.9 (M+H)$^+$; R$_t$=0.41 and 0.46 min.

Example 4-6

Gadolinium 2,2',2''-[10-(2-{(2-ethoxyethyl)[2-(4-nitrophenoxy)-2-oxoethyl]amino}-2-oxo-ethyl)-1,4,7,10-tetraazacyclododecane-1,4,7-triyl]triacetate

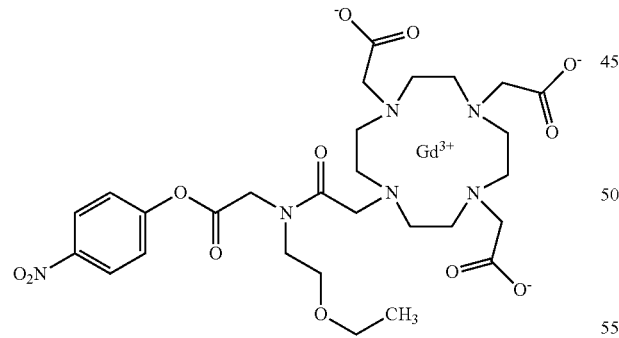

The compound was synthesized according to the procedure described in example 1-5 starting from 4.93 g (7.17 mmol, 1 eq.) gadolinium 2,2',2''-(10-{2-[(carboxymethyl)(2-ethoxyethyl)amino]-2-oxoethyl}-1,4,7,10-tetraazacyclododecane-1,4,7-triyl)triacetate (example 4-5), 2.00 g (14.35 mmol, 2 eq.) 4-nitrophenol, and 1.36 g (10.76 mmol, 1.5 eq.) N,N'diisopropyl carbodiimide yielding 5.05 g (87%, 6.24 mmol).

LC-MS (ES$^+$): m/z=810.3 (M+H)$^+$; R$_t$=0.72 and 0.74 min.

Example 4

Tetragadolinium {4,10-bis(carboxylatomethyl)-7-[16-(2-ethoxyethyl)-11,11-bis[({[(2-ethoxyethyl){[4,7,10-tris(carboxylatomethyl)-1,4,7,10-tetraazacyclododecan-1-yl]-acetyl}amino]acetyl}amino)methyl]-8,14,17-trioxo-6-{[4,7,10-tris(carboxylatomethyl)-1,4,7,10-tetraazacyclododecan-1-yl]acetyl}-3-oxa-6,9,13,16-tetraazaoctadecan-18-yl]-1,4,7,10-tetraazacyclododecan-1-yl}acetate The compound was synthesized according to the procedure described in example 1 starting from 158.4 mg (0.57 mmol, 1 eq.) 2,2-bis(ammoniomethyl)propane-1,3-diaminium tetrachloride, 589.0 mg (4.56 mmol, 8 eq.) N,N-diisopropyl ethylamine, and 5.53 g (6.84 mmol, 12 eq.) gadolinium 2,2',2''-[10-(2-{(2-ethoxyethyl)[2-(4-nitrophenoxy)-2-oxoethyl]amino}-2-oxoethyl)-1,4,7,10-tetraazacyclododecane-1,4,7-triyl]triacetate (example 4-6) yielding 365 mg (23%, 0.13 mmol).

UPLC (ACN-HCOOH): R$_t$=0.51 min.

MS (ES$^+$): m/z (z=2)=1406.5 (M+H)$^{2+}$, m/z (z=3)=938.3 (M+H)$^{3+}$.

Example 5

Tetragadolinium [4,10-bis(carboxylatomethyl)-7-{3,13-diisopropyl-8,8-bis({[(isopropyl-{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate

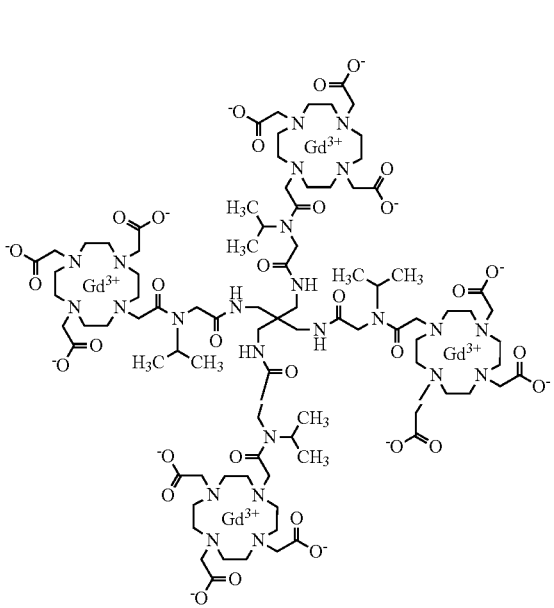

Example 5-1

Tert-butyl N-isopropyl-N-{[4,7,10-tris(2-tert-butoxy-2-oxoethyl)-1,4,7,10-tetraazacyclo-dodecan-1-yl]acetyl}glycinate

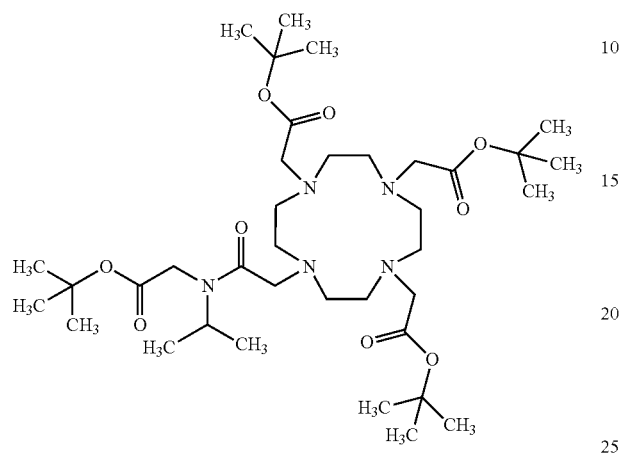

The compound was synthesized according to the procedure described in example 1-2 starting from 5.05 g (9.81 mmol, 1 eq.) tri-tert-butyl 2,2',2"-(1,4,7,10-tetraazacyclododecane-1,4,7-triyl)triacetate, 4.07 g (29.43 mmol, 3 eq.) potassium carbonate, and 2.89 g (9.81 mmol, 1 eq.) tert-butyl N-(bromoacetyl)-N-isopropylglycinate [see J. M. Kim et al., Carbohydrate Research, 298(3), 173-179 (1997)] yielding 6.83 g (86%, 8.44 mmol).

$^1$H-NMR (400 MHz, CDCl$_3$): δ=1.00-1.26 (m, 6H), 1.34-1.56 (m, 36H), 1.68-5.00 (m, 27H) ppm.
LC-MS (ES$^+$): m/z=728.6 (M+H)$^+$; R$_t$=1.04 min.

Example 5-2

N-isopropyl-N-{[4,7,10-tris(carboxymethyl)-1,4,7,10-tetraazacyclododecan-1-yl]acetyl}-glycine

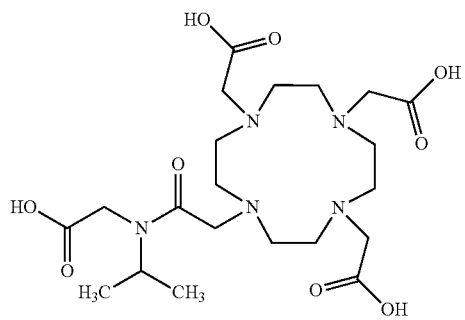 [SMILES: CC(C)N(CC(=O)O)C(=O)CN1CCN(CC(=O)O)CCN(CC(=O)O)CCN(CC(=O)O)CC1]

The compound was synthesized according to the procedure described in example 1-3 starting from 6.83 g (9.38 mmol) tert-butyl N-isopropyl-N-{[4,7,10-tris(2-tert-butoxy-2-oxoethyl)-1,4,7,10-tetraazacyclododecan-1-yl]acetyl}glycinate (example 5-1) in 140 ml formic acid yielding 5.17 g (109%, 10.27 mmol).

$^1$H-NMR (400 MHz, D$_2$O): δ=0.94-1.25 (m, 6H), 2.50-4.42 (m, 27H) ppm.
LC-MS (ES$^+$): m/z=504.2 (M+H)$^+$; R$_t$=0.41 min.

Example 5-3

Gadolinium 2,2',2"-(10-{2-[(carboxymethyl)(isopropyl)amino]-2-oxoethyl}-1,4,7,10-tetraazacyclododecane-1,4,7-triyl)triacetate

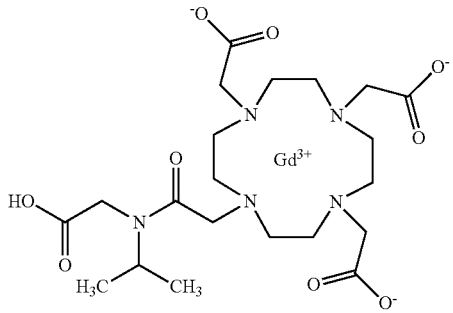

The compound was synthesized according to the procedure described in example 1-4 starting from 5.17 g (10.27 mmol, 1 eq.) N-isopropyl-N-{[4,7,10-tris(carboxymethyl)-1,4,7,10-tetraazacyclododecan-1-yl]acetyl}glycine (example 5-2) and 1.68 g (4.62 mmol, 0.45 eq.) gadolinium(III) oxide yielding 6.16 g (91%, 9.36 mmol).

LC-MS (ES$^+$): m/z=659.1 (M+H)$^+$; R$_t$=0.39 and 0.42 min.

Example 5-4

Gadolinium 2,2',2"-[10-(2-{isopropyl[2-(4-nitrophenoxy)-2-oxoethyl]amino}-2-oxoethyl)-1,4,7,10-tetraazacyclododecane-1,4,7-triyl]triacetate

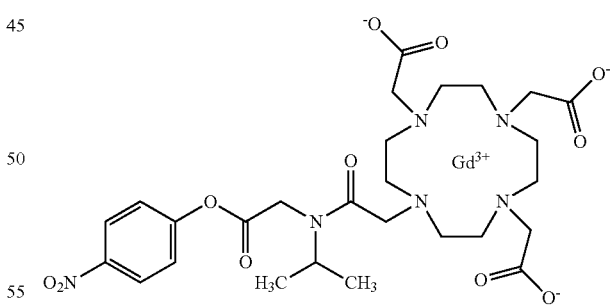

The compound was synthesized according to the procedure described in example 1-5 starting from 5.63 g (8.56 mmol, 1 eq.) gadolinium 2,2',2"-(10-{2-[(carboxymethyl)(iso-propyl)amino]-2-oxoethyl}-1,4,7,10-tetraazacyclododecane-1,4,7-triyl)triacetate (example 5-3), 2.38 g (17.12 mmol, 2 eq.) 4-nitrophenol, and 1.62 g (12.84 mmol, 1.5 eq.) N,N'diisopropyl carbodiimide yielding 6.26 g (94%, 8.04 mmol).

LC-MS (ES$^+$): m/z=779.4 (M+H)$^+$; R$_t$=0.63 and 0.68 min.

Example 5

Tetragadolinium [4,10-bis(carboxylatomethyl)-7-{3,13-diisopropyl-8,8-bis({[(isopropyl-{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate The compound was synthesized according to the procedure described in example 1 starting from 161.7 mg (0.58 mmol, 1 eq.) 2,2-bis(ammoniomethyl)propane-1,3-diaminium tetrachloride, 752.0 mg (4.65 mmol, 8 eq.) N,N-diisopropyl ethylamine, and 6.80 g (8.72 mmol, 12 eq.) gadolinium 2,2',2''-[10-(2-{isopropyl[2-(4-nitrophenoxy)-2-oxoethyl]amino}-2-oxoethyl)-1,4,7,10-tetraazacyclododecane-1,4,7-triyl]triacetate (example 5-4) yielding 262 mg (17%, 0.097 mmol).

UPLC (ACN-HCOOH): $R_f$=0.44 min.

MS (ES$^+$): m/z (z=2)=1347.5 (M+H)$^{2+}$, m/z (z=3)=897.9 (M+H)$^{3+}$.

Example 6

Tetragadolinium {4,10-bis(carboxylatomethyl)-7-[3-isobutyl-8,8-bis({[(isobutyl{[4,7,10-tris(carboxylatomethyl)-1,4,7,10-tetraazacyclododecan-1-yl]acetyl}amino)acetyl]-amino}methyl)-15-methyl-2,5,11-trioxo-13-{[4,7,10-tris(carboxylatomethyl)-1,4,7,10-tetraazacyclododecan-1-yl]acetyl}-3,6,10,13-tetraazahexadec-1-yl]-1,4,7,10-tetraazacyclododecan-1-yl}acetate

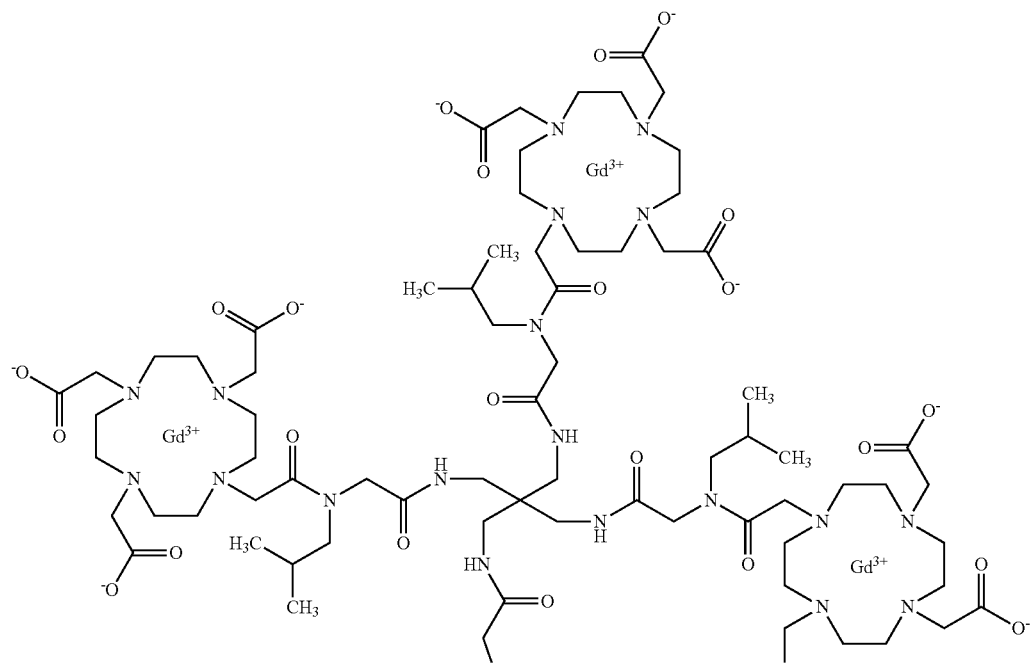

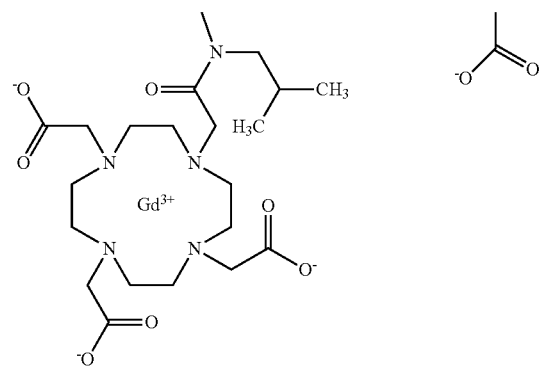

Example 6-1

Tert-butyl N-isobutyl-N-{[4,7,10-tris(2-tert-butoxy-2-oxoethyl)-1,4,7,10-tetraazacyclo-dodecan-1-yl]acetyl}glycinate

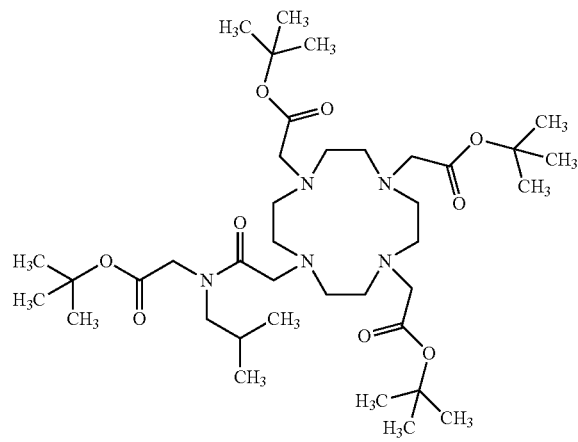 [SMILES: CC(C)CN(CC(=O)OC(C)(C)C)C(=O)CN1CCN(CC(=O)OC(C)(C)C)CCN(CC(=O)OC(C)(C)C)CCN(CC(=O)OC(C)(C)C)CC1]

The compound was synthesized according to the procedure described in example 1-2 starting from 13.73 g (26.67 mmol, 1 eq.) tri-tert-butyl 2,2',2"-(1,4,7,10-tetraazacyclododecane-1,4,7-triyl)triacetate, 11.06 g (80.01 mmol, 3 eq.) potassium carbonate, and 8.22 g (26.67 mmol, 1 eq.) tert-butyl N-(bromoacetyl)-N-isobutylglycinate [see U. K. Saha et al., Tetrahedron Letters 36(21), 3635-3638 (1995)] yielding 13.47 g (65%, 17.25 mmol).

$^1$H-NMR (400 MHz, CDCl$_3$): δ=0.80-1.04 (m, 6H), 1.24-1.57 (m, 36H), 1.61-4.40 (m, 29H) ppm.

LC-MS (ES$^+$): m/z=742.5 (M+H)$^+$; R$_t$=1.17 min.

Example 6-2

N-isobutyl-N-{[4,7,10-tris(carboxymethyl)-1,4,7,10-tetraazacyclododecan-1-yl]acetyl}-glycine

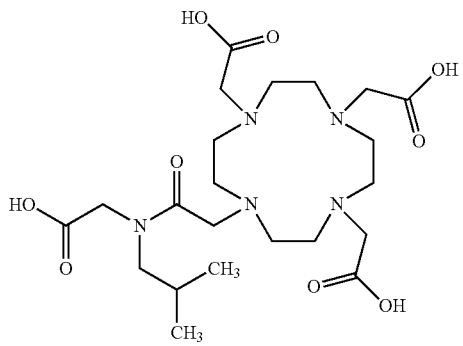 [SMILES: CC(C)CN(CC(=O)O)C(=O)CN1CCN(CC(=O)O)CCN(CC(=O)O)CCN(CC(=O)O)CC1]

The compound was synthesized according to the procedure described in example 1-3 starting from 13.47 g (18.15 mmol) tert-butyl N-isobutyl-N-{[4,7,10-tris(2-tert-butoxy-2-oxoethyl)-1,4,7,10-tetraazacyclododecan-1-yl]acetyl}glycinate (example 6-1) in 270 ml formic acid yielding 8.79 g (94%, 17.00 mmol).

$^1$H-NMR (400 MHz, D$_2$O): δ=0.71-0.92 (m, 6H), 1.67-1.97 (m, 1H), 2.96-4.03 (m, 28H) ppm.

LC-MS (ES$^+$): m/z=518.8 (M+H)$^+$; R$_t$=0.44 min.

Example 6-3

Gadolinium 2,2',2"-(10-{2-[(carboxymethyl)(isobutyl)amino]-2-oxoethyl}-1,4,7,10-tetra-azacyclododecane-1,4,7-triyl)triacetate

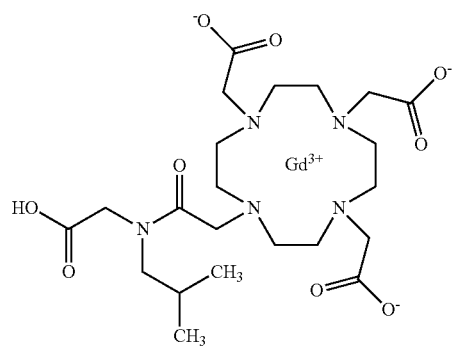

The compound was synthesized according to the procedure described in example 1-4 starting from 8.79 g (16.98 mmol, 1 eq.) N-isobutyl-N-{[4,7,10-tris(carboxymethyl)-1,4,7,10-tetraazacyclododecan-1-yl]acetyl}glycine (example 6-2) and 2.77 g (7.64 mmol, 0.45 eq.) gadolinium(III) oxide yielding 9.62 g (76%, 12.89 mmol).

LC-MS (ES$^+$): m/z=673.1 (M+H)$^+$; R$_t$=0.43 and 0.48 min.

Example 6-4

Gadolinium 2,2',2"-[10-(2-{isobutyl[2-(4-nitrophenoxy)-2-oxoethyl]amino}-2-oxoethyl)-1,4,7,10-tetraazacyclododecane-1,4,7-triyl]triacetate

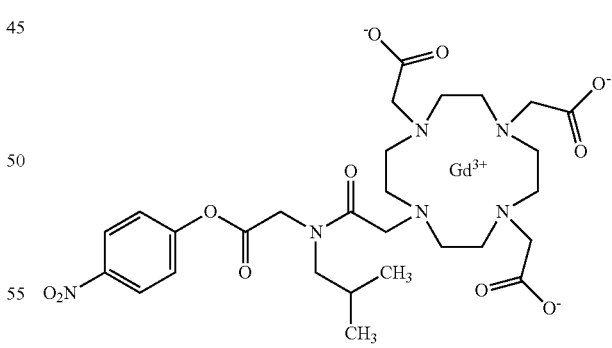

The compound was synthesized according to the procedure described in example 1-5 starting from 9.12 g (13.57 mmol, 1 eq.) gadolinium 2,2',2"-(10-{2-[(carboxymethyl)(isobutyl)amino]-2-oxoethyl}-1,4,7,10-tetraazacyclododecane-1,4,7-triyl)triacetate (example 6-3), 3.78 g (27.15 mmol, 2 eq.) 4-nitrophenol, and 2.57 g (20.36 mmol, 1.5 eq.) N,N'diisopropyl carbodiimide yielding 9.67 g (81%, 10.98 mmol).

LC-MS (ES$^+$): m/z=794.3 (M+H)$^+$; R$_t$=0.74 min.

Example 6

Tetragadolinium {4,10-bis(carboxylatomethyl)-7-[3-isobutyl-8,8-bis({[(isobutyl{[4,7,10-tris(carboxylatomethyl)-1,4,7,10-tetraazacyclododecan-1-yl]acetyl}amino)acetyl]-amino}methyl)-15-methyl-2,5,11-trioxo-13-{[4,7,10-tris(carboxylatomethyl)-1,4,7,10-tetraazacyclododecan-1-yl]acetyl}-3,6,10,13-tetraazahexadec-1-yl]-1,4,7,10-tetraazacyclododecan-1-yl}acetate The compound was synthesized according to the procedure described in example 1 starting from 269.0 mg (0.97 mmol, 0.9 eq.) 2,2-bis(ammoniomethyl)propane-1,3-diaminium tetrachloride, 1.11 g (8.58 mmol, 8 eq.) N,N-diisopropyl ethylamine, and 10.21 g (12.88 mmol, 12 eq.) gadolinium 2,2',2''-[10-(2-{isobutyl[2-(4-nitrophenoxy)-2-oxoethyl]amino}-2-oxoethyl)-1,4,7,10-tetraazacyclododecane-1,4,7-triyl]triacetate (example 6-4) yielding 674 mg (25%, 0.245 mmol).

UPLC (ACN-HCOOH): $R_t$=0.54 min.

MS (ES$^+$): m/z (z=2)=1373.4 (M+H)$^{2+}$, m/z (z=3)=916.0 (M+H)$^{3+}$.

Example 7

Tetragadolinium [4,10-bis(carboxylatomethyl)-7-{3,13-dicycopropyl-8,8-bis({[(cyclo-propyl{[4,7,10-tris(carboxylatomethyl)-1,4,7,10-tetraazacyclododecan-1-yl]acetyl}-amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate

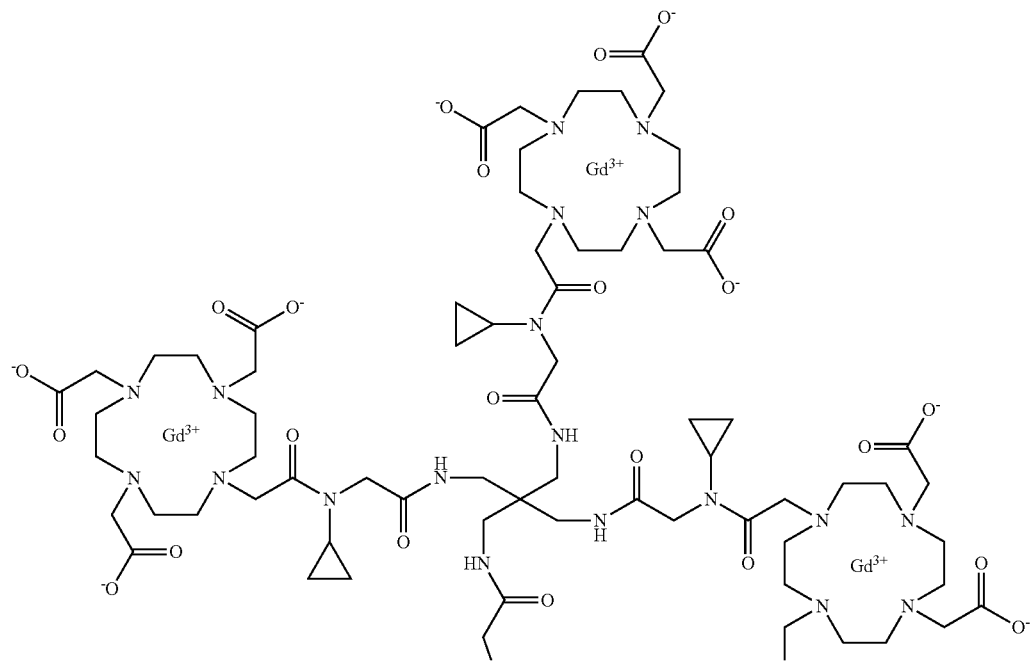

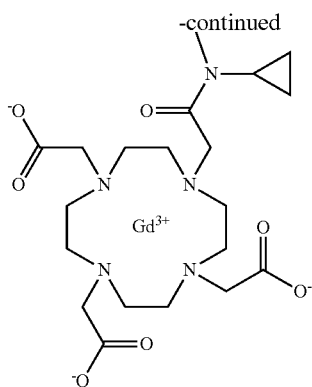 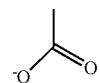

Example 7-1

Tert-butyl N-(bromoacetyl)-N-cyclopropylglycinate

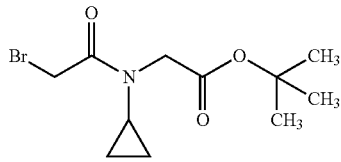 [SMILES: CC(C)(C)OC(=O)CN(C(=O)CBr)C1CC1]

The compound was synthesized according to the procedure described in example 1-1 starting from 1.98 g (11.56 mmol, 1 eq.) tert-butyl N-cyclopropylglycinate [see J. T. Suh et al., J. Med. Chem. 28(1), 57-66 (1985)], 1.60 g (12.37 mmol, 1.07 eq.) N,N-diisopropyl ethylamine, and 2.50 g (12.37 mmol, 1.07 eq.) bromoacetyl bromide yielding 3.24 g (96%, 11.09 mmol).

$^1$H-NMR (400 MHz, CDCl$_3$): δ=0.83-1.00 (m, 4H), 1.46 (s, 9H), 2.95-3.04 (m, 1H), 4.00 (s, 2H), 4.16 (s, 2H) ppm.

LC-MS (ES$^+$): m/z=292.3 and 294.3 (M+H)$^+$; R$_t$=1.09 min.

Example 7-2

Tert-butyl N-cyclopropyl-N-{[4,7,10-tris(2-tert-butoxy-2-oxoethyl)-1,4,7,10-tetraaza-cyclododecan-1-yl]acetyl}glycinate

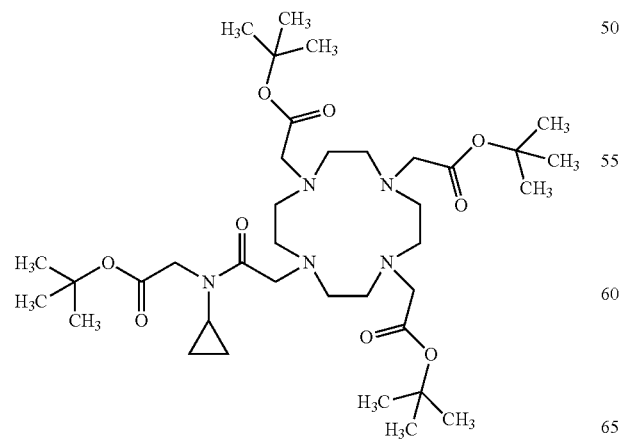

The compound was synthesized according to the procedure described in example 1-2 starting from 5.00 g (9.71 mmol, 1 eq.) tri-tert-butyl 2,2',2''-(1,4,7,10-tetraazacyclododecane-1,4,7-triyl)triacetate, 4.03 g (29.14 mmol, 3 eq.) potassium carbonate, and 2.84 g (8.41 mmol, 1 eq.) tert-butyl N-(bromoacetyl)-N-cyclopropylglycinate (example 7-1) yielding 6.38 g (91%, 8.79 mmol).

$^1$H-NMR (400 MHz, CDCl$_3$): δ=0.63-1.02 (m, 4H), 1.35-1.54 (m, 36H), 1.75-4.50 (m, 27H) ppm.

LC-MS (ES$^+$): m/z=726.7 (M+H)$^+$; R$_t$=0.98 min.

Example 7-3

N-cyclopropyl-N-{[4,7,10-tris(carboxymethyl)-1,4,7,10-tetraazacyclododecan-1-yl]-acetyl}glycine

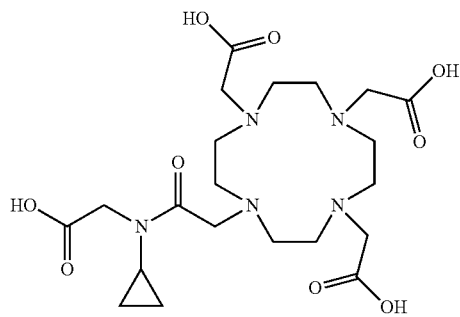 [SMILES: O=C(O)CN1CCN(CC(=O)O)CCN(CC(=O)N(CC(=O)O)C2CC2)CCN(CC(=O)O)CC1]

The compound was synthesized according to the procedure described in example 1-3 starting from 6.38 g (8.79 mmol) tert-butyl N-cyclopropyl-N-{[4,7,10-tris(2-tert-butoxy-2-oxoethyl)-1,4,7,10-tetraazacyclododecan-1-yl]acetyl}glycinate (example 7-2) in 132 ml formic acid yielding 4.70 g (107%, 9.37 mmol).

$^1$H-NMR (400 MHz, D$_2$O): δ=0.67-0.88 (m, 4H), 2.71-2.79 (m, 1H), 2.88-4.31 (m, 26H) ppm.

LC-MS (ES$^+$): m/z=502.2 (M+H)$^+$; R$_t$=0.34 min.

Example 7-4

Gadolinium 2,2',2"-(10-{2-[(carboxymethyl)(cyclopropyl)amino]-2-oxoethyl}-1,4,7,10-tetraazacyclododecane-1,4,7-triyl)triacetate The compound was synthesized according to the procedure described in example 1-4 starting from 4.68 g (9.33 mmol, 1 eq.) N-cyclopropyl-N-{[4,7,10-tris(carboxymethyl)-1,4,7,10-tetraazacyclododecan-1-yl]acetyl}glycine (example 7-3) and 1.52 g (4.20 mmol, 0.45 eq.) gadolinium (III) oxide yielding 5.46 g (89%, 8.33 mmol).

LC-MS (ES$^+$): m/z=657.1 (M+H)$^+$; R$_t$=0.41 min.

Example 7-5

Gadolinium 2,2',2"-[10-(2-{cyclopropyl[2-(4-nitrophenoxy)-2-oxoethyl]amino}-2-oxoethyl)-1,4,7,10-tetraazacyclododecane-1,4,7-triyl]triacetate

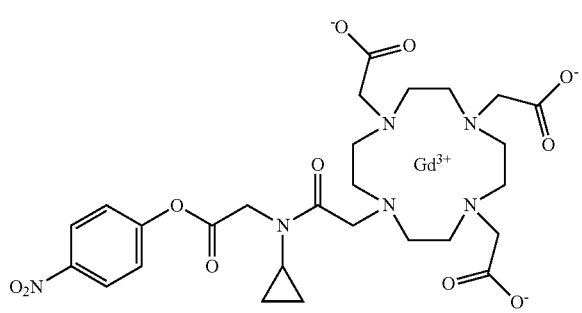

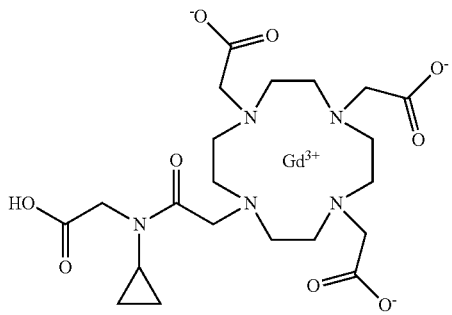

The compound was synthesized according to the procedure described in example 1-5 starting from 4.95 g (7.55 mmol, 1 eq.) gadolinium 2,2',2"-(10-{2-[(carboxymethyl)(cyclopropyl)amino]-2-oxoethyl}-1,4,7,10-tetraazacyclododecane-1,4,7-triyl)triacetate (example 7-4), 2.10 g (15.10 mmol, 2 eq.) 4-nitrophenol, and 1.43 g (11.32 mmol, 1.5 eq.) N,N'diisopropyl carbodiimide yielding 5.76 g (98%, 7.41 mmol).

LC-MS (ES$^+$): m/z=778.0 (M+H)$^+$; R$_t$=0.66 min.

Example 7

Tetragadolinium [4,10-bis(carboxylatomethyl)-7-{3,13-dicycopropyl-8,8-bis({[(cyclo-propyl{[4,7,10-tris(carboxylatomethyl)-1,4,7,10-tetraazacyclododecan-1-yl]acetyl}-amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate The compound was synthesized according to the procedure described in example 1 starting from 188.2 mg (0.68 mmol, 1 eq.) 2,2-bis(ammoniomethyl)propane-1,3-diaminium tetrachloride, 700.0 mg (5.42 mmol, 8 eq.) N,N-diisopropyl ethylamine, and 6.31 g (8.12 mmol, 12 eq.) gadolinium 2,2',2''-[10-(2-{cyclopropyl[2-(4-nitrophenoxy)-2-oxoethyl]amino}-2-oxoethyl)-1,4,7,10-tetraazacyclododecane-1,4,7-triyl]triacetate (example 7-5) yielding 627 mg (35%, 0.234 mmol).

UPLC (ACN-HCOOH): $R_f$=0.44 min.

MS (ES$^+$): m/z (z=2)=1343.4 (M+H)$^{2+}$, m/z (z=3)=895.8 (M+H)$^{3+}$

Example 8

Tetragadolinium[4,10-bis(carboxylatomethyl)-7-{3,13-dicyclopentyl-8,8-bis({[(cyclo-pentyl{[4,7,10-tris(carboxylatomethyl)-1,4,7,10-tetraazacyclododecan-1-yl]acetyl}-amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate

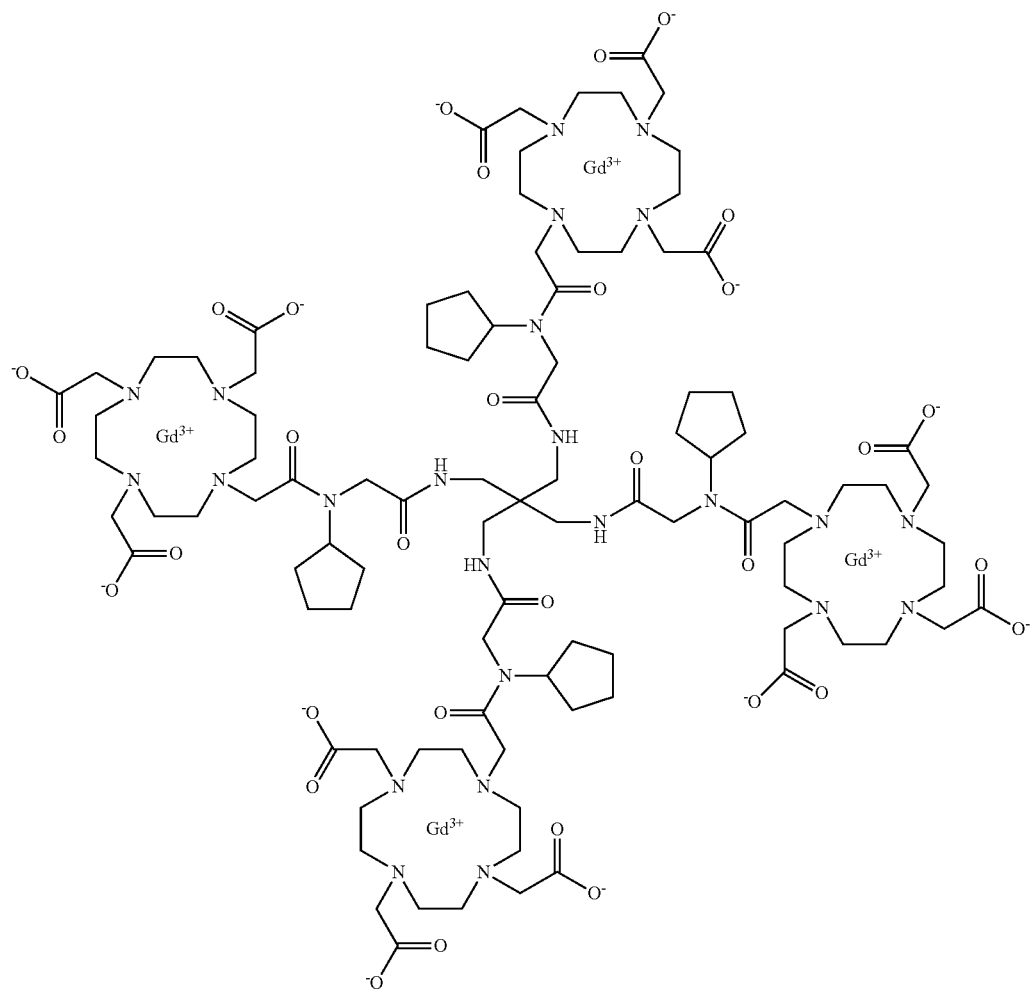

Example 8-1

Tert-butyl N-(bromoacetyl)-N-cyclopentylglycinate

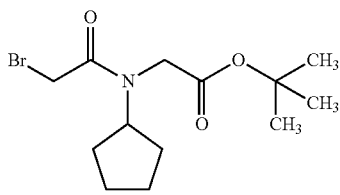 [SMILES: CC(C)(C)OC(=O)CN(C(=O)CBr)C1CCCC1]

The compound was synthesized according to the procedure described in example 1-1 starting from 5.24 g (26.29 mmol, 1 eq.) tert-butyl N-cyclopentylglycinate [see J. T. Suh et al., J. Med. Chem. 28(1), 57-66 (1985)], 3.64 g (28.13 mmol, 1.07 eq.) N,N-diisopropyl ethylamine, and 5.68 g (28.13 mmol, 1.07 eq.) bromoacetyl bromide yielding 8.40 g (89%, 23.61 mmol).

$^1$H-NMR (400 MHz, CDCl$_3$): δ=1.21-2.12 (m, 17H), 3.73-3.86 (m, 2H), 3.94 (s, 2H), 4.14-4.87 (m, 1H) ppm.

LC-MS (ES$^+$): m/z=320.1 and 322.1 (M+H)$^+$; R$_t$=1.25 min.

Example 8-2

Tert-butyl N-cyclopentyl-N-{[4,7,10-tris(2-tert-butoxy-2-oxoethyl)-1,4,7,10-tetraaza-cyclododecan-1-yl]acetyl}glycinate

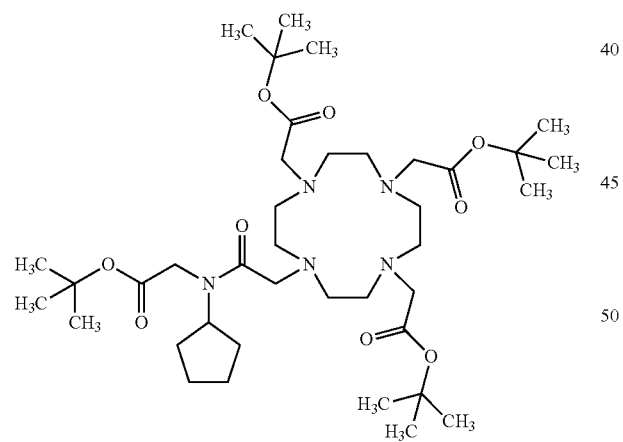

The compound was synthesized according to the procedure described in example 1-2 starting from 8.07 g (15.68 mmol, 1 eq.) tri-tert-butyl 2,2',2''-(1,4,7,10-tetraazacyclododecane-1,4,7-triyl)triacetate, 6.50 g (47.03 mmol, 3 eq.) potassium carbonate, and 5.02 g (15.68 mmol, 1 eq.) tert-butyl N-(bromoacetyl)-N-cyclopentylglycinate (example 8-1) yielding 8.95 g (76%, 11.87 mmol).

$^1$H-NMR (400 MHz, CDCl$_3$): δ=1.33-1.51 (m, 36H), 1.55-5.00 (m, 35H) ppm.

LC-MS (ES$^+$): m/z=754.5 (M+H)$^+$; R$_t$=1.15 min.

Example 8-3

N-cyclopentyl-N-{[4,7,10-tris(carboxymethyl)-1,4,7,10-tetraazacyclododecan-1-yl]-acetyl}glycine

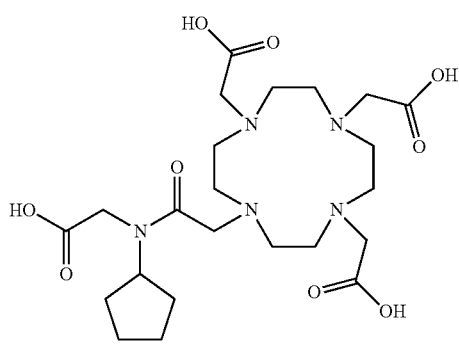 [SMILES: O=C(O)CN1CCN(CC(=O)O)CCN(CC(=O)N(CC(=O)O)C2CCCC2)CCN(CC(=O)O)CC1]

The compound was synthesized according to the procedure described in example 1-3 starting from 8.94 g (11.86 mmol) tert-butyl N-cyclopentyl-N-{[4,7,10-tris(2-tert-butoxy-2-oxoethyl)-1,4,7,10-tetraazacyclododecan-1-yl] acetyl}glycinate (example 8-2) in 180 ml formic acid yielding 6.20 g (74%, 8.78 mmol).

LC-MS (ES$^+$): m/z=530.2 (M+H)$^+$; R$_t$=0.40 and 0.46 min.

Example 8-4

Gadolinium 2,2',2''-(10-{2-[(carboxymethyl)(cyclopentyl)amino]-2-oxoethyl}-1,4,7,10-tetraazacyclododecane-1,4,7-triyl)triacetate

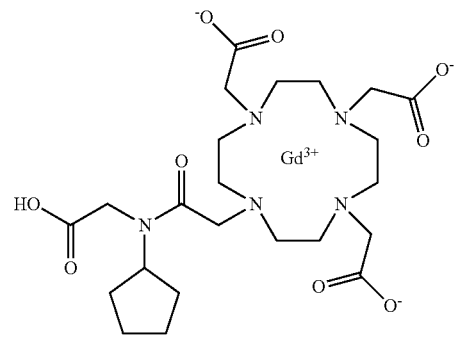

The compound was synthesized according to the procedure described in example 1-4 starting from 6.20 g (11.71 mmol, 1 eq.) N-cyclopentyl-N-{[4,7,10-tris(carboxymethyl)-1,4,7,10-tetraazacyclododecan-1-yl]acetyl}glycine (example 8-3) and 1.91 g (5.27 mmol, 0.45 eq.) gadolinium (III) oxide yielding 7.21 g (90%, 10.54 mmol).

LC-MS (ES$^+$): m/z=685.0 (M+H)$^+$; R$_t$=0.44 and 0.50 min.

Example 8-5

Gadolinium 2,2',2''-[10-(2-{cyclopentyl[2-(4-nitrophenoxy)-2-oxoethyl]amino}-2-oxoethyl)-1,4,7,10-tetraazacyclododecane-1,4,7-triyl]triacetate

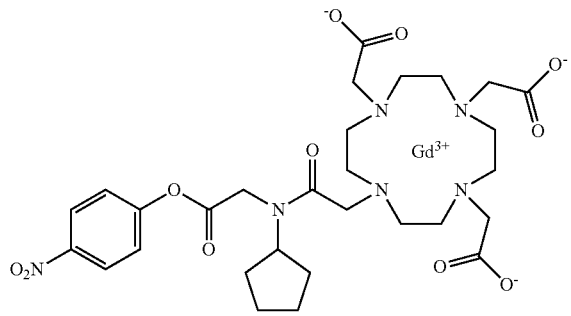

The compound was synthesized according to the procedure described in example 1-5 starting from 6.70 g (9.80 mmol, 1 eq.) gadolinium 2,2',2''-(10-{2-[(carboxymethyl)(cyclopentyl)amino]-2-oxoethyl}-1,4,7,10-tetraazacyclododecane-1,4,7-triyl)triacetate (example 8-4), 2.73 g (19.60 mmol, 2 eq.) 4-nitrophenol, and 1.86 g (14.70 mmol, 1.5 eq.) N,N'diisopropyl carbodiimide yielding 7.08 g (90%, 8.79 mmol).

LC-MS (ES$^+$): m/z=806.1 (M+H)$^+$; R$_t$=0.71 and 0.77 min.

Example 8

Tetragadolinium [4,10-bis(carboxylatomethyl)-7-{3,13-dicyclopentyl-8,8-bis({[(cyclo-pentyl{[4,7,10-tris(carboxylatomethyl)-1,4,7,10-tetraazacyclododecan-1-yl]acetyl}-amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetra-azacyclododecan-1-yl]acetate The compound was synthesized according to the procedure described in example 1 starting from 130.4 mg (0.47 mmol, 0.6 eq.) 2,2-bis(ammoniomethyl)propane-1,3-diaminium tetrachloride, 808.0 mg (6.25 mmol, 8 eq.) N,N-diisopropyl ethylamine, and 7.55 g (9.38 mmol, 12 eq.) gadolinium 2,2',2''-[10-(2-{cyclopentyl[2-(4-nitrophenoxy)-2-oxoethyl]amino}-2-oxoethyl)-1,4,7,10-tetraazacyclododecane-1,4,7-triyl]triacetate (example 8-5) yielding 222 mg (17%, 0.08 mmol).

UPLC (ACN-HCOOH): R$_t$=0.56 min.
MS (ES$^+$): m/z (z=2)=1400.0 (M+H)$^{2+}$, m/z (z=3)=933.0 (M+H)$^{3+}$

Example 9

Tetragadolinium [4,10-bis(carboxylatomethyl)-7-{2,5,11,14-tetraoxo-3,13-diphenyl-8,8-bis({[(phenyl{[4,7,10-tris(carboxylatomethyl)-1,4,7,10-tetraazacyclododecan-1-yl]-acetyl}amino)acetyl]amino}methyl)-15-[4,7,10-tris(carboxylatomethyl)-1,4,7,10-tetra-azacyclododecan-1-yl]-3,6,10,13-tetraazapentadec-1-yl]-1,4,7,10-tetraaza1cyclododecan-1-yl]acetate

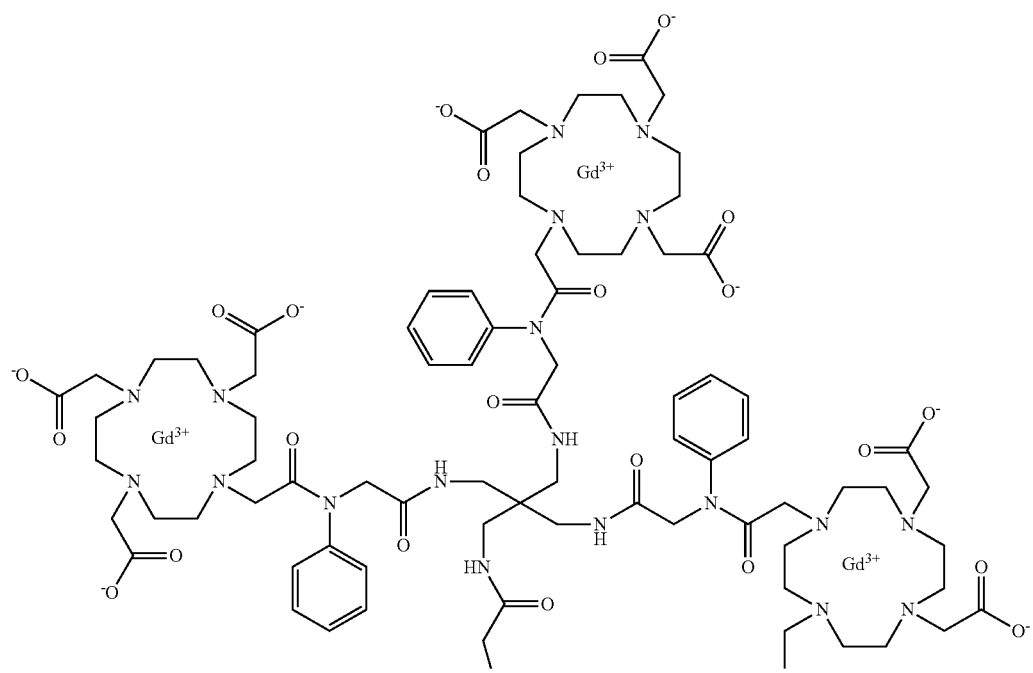

Example 9-1

Tert-butyl N-phenyl-N-{[4,7,10-tris(2-tert-butoxy-2-oxoethyl)-1,4,7,10-tetraazacyclo-dodecan-1-yl]acetyl}glycinate Example 9-2

N-phenyl-N-{[4,7,10-tris(carboxymethyl)-1,4,7,10-tetraazacyclododecan-1-yl]acetyl}-glycine

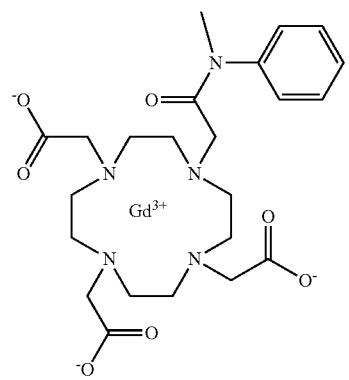
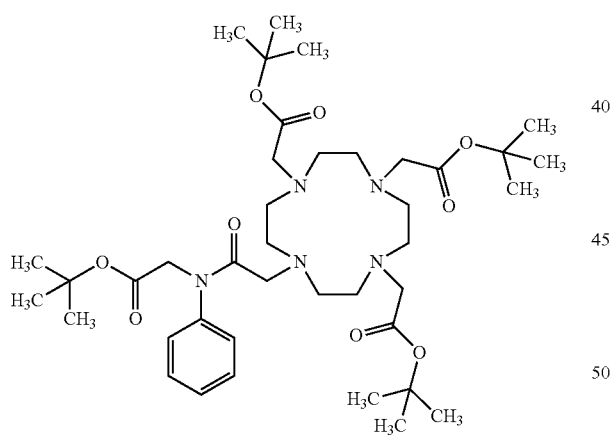
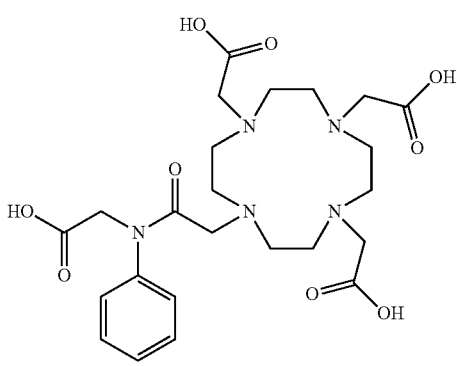 [SMILES: O=C(O)CN1CCN(CC(=O)O)CCN(CC(=O)N(CC(=O)O)c2ccccc2)CCN(CC(=O)O)CC1]

The compound was synthesized according to the procedure described in example 1-2 starting from 9.00 g (17.49 mmol, 1 eq.) tri-tert-butyl 2,2',2"-(1,4,7,10-tetraazacyclododecane-1,4,7-triyl)triacetate, 7.25 g (52.46 mmol, 3 eq.) potassium carbonate, and 5.74 g (17.49 mmol, 1 eq.) tert-butyl N-(bromoacetyl)-N-phenylglycinate [see C. Roy et al., Organic Letters 15(9), 2246-2249 (2013)] yielding 7.74 g (58%, 10.16 mmol).

$^1$H-NMR (400 MHz, CDCl$_3$): δ=1.30-1.64 (m, 36H), 1.67-4.78 (m, 26H), 7.22-7.26 (m, 2H), 7.36-7.46 (m, 3H) ppm.

LC-MS (ES$^+$): m/z=763.5 (M+H)$^+$; R$_t$=1.11 min.

The compound was synthesized according to the procedure described in example 1-3 starting from 7.20 g (9.45 mmol) tert-butyl N-phenyl-N-{[4,7,10-tris(2-tert-butoxy-2-oxoethyl)-1,4,7,10-tetraazacyclododecan-1-yl]acetyl}glycinate (example 9-1) in 144 ml formic acid yielding 5.54 g (109%, 10.31 mmol).

$^1$H-NMR (400 MHz, D$_2$O): δ=2.65-4.42 (m, 26H), 7.12-7.59 (m, 5H) ppm.

LC-MS (ES$^+$): m/z=538.2 (M+H)$^+$; R$_t$=0.45 min.

Example 9-3

Gadolinium 2,2',2''-(10-{2-[(carboxymethyl)(phenyl)amino]-2-oxoethyl}-1,4,7,10-tetra-azacyclododecane-1,4,7-triyl)triacetate

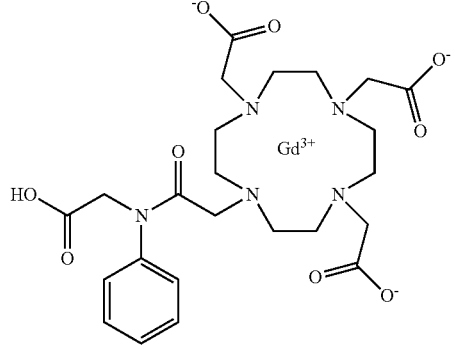

The compound was synthesized according to the procedure described in example 1-4 starting from 5.54 g (10.31 mmol, 1 eq.) N-phenyl-N-{[4,7,10-tris(carboxymethyl)-1,4,7,10-tetraazacyclododecan-1-yl]acetyl}glycine (example 9-2) and 1.68 g (4.64 mmol, 0.45 eq.) gadolinium(III) oxide yielding 7.10 g (100%, 10.26 mmol).

LC-MS (ES$^+$): m/z=693.1 (M+H)$^+$; R$_t$=0.51 min.

Example 9-4

Gadolinium 2,2',2''-[10-(2-{[2-(4-nitrophenoxy)-2-oxoethyl](phenyl)amino}-2-oxoethyl)-1,4,7,10-tetraazacyclododecane-1,4,7-triyl]triacetate The compound was synthesized according to the procedure described in example 1-5 starting from 3.93 g (5.68 mmol, 1 eq.) gadolinium 2,2',2''-(10-{2-[(carboxymethyl)(phenyl)amino]-2-oxoethyl}-1,4,7,10-tetraazacyclododecane-1,4,7-triyl)triacetate (example 9-3), 1.58 g (11.36 mmol, 2 eq.) 4-nitrophenol, and 1.08 g (8.52 mmol, 1.5 eq.) N,N'diisopropyl carbodiimide yielding 4.06 g (88%, 4.99 mmol).

LC-MS (ES$^+$): m/z=814.3 (M+H)$^+$; R$_t$=0.77 min.

Example 9

Tetragadolinium [4,10-bis(carboxylatomethyl)-7-{2,5,11,14-tetraoxo-3,13-diphenyl-8,8-bis({[(phenyl{[4,7,10-tris(carboxylatomethyl)-1,4,7,10-tetraazacyclododecan-1-yl]-acetyl}amino)acetyl]amino}methyl)-15-[4,7,10-tris(carboxylatomethyl)-1,4,7,10-tetra-azacyclododecan-1-yl]-3,6,10,13-tetraazapentadec-1-yl}-1,4,7,10-tetraazacyclododecan-1-yl]acetate The compound was synthesized according to the procedure described in example 1 starting from 129.4 mg (0.47 mmol, 1 eq.) 2,2-bis(ammoniomethyl)propane-1,3-diaminium tetrachloride, 481.0 mg (3.72 mmol, 8 eq.) N,N-diisopropyl ethylamine, and 4.54 g (5.59 mmol, 12 eq.) gadolinium 2,2',2''-[10-(2-{[2-(4-nitrophenoxy)-2-oxoethyl](phenyl)amino}-2-oxoethyl)-1,4,7,10-tetraazacyclododecane-1,4,7-triyl]triacetate (example 9-4) yielding 663 mg (50%, 0.23 mmol).

UPLC (ACN-HCOOH): R$_t$=0.61 min.

MS (ES$^+$): m/z (z=2)=1415.0 (M+H)$^{2+}$, m/z (z=3)=944.4 (M+H)$^{3+}$.

Example 10
Tetragadolinium [4,10-bis(carboxylatomethyl)-7-{3,13-dibenzyl-8,8-bis({[(benzyl{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate
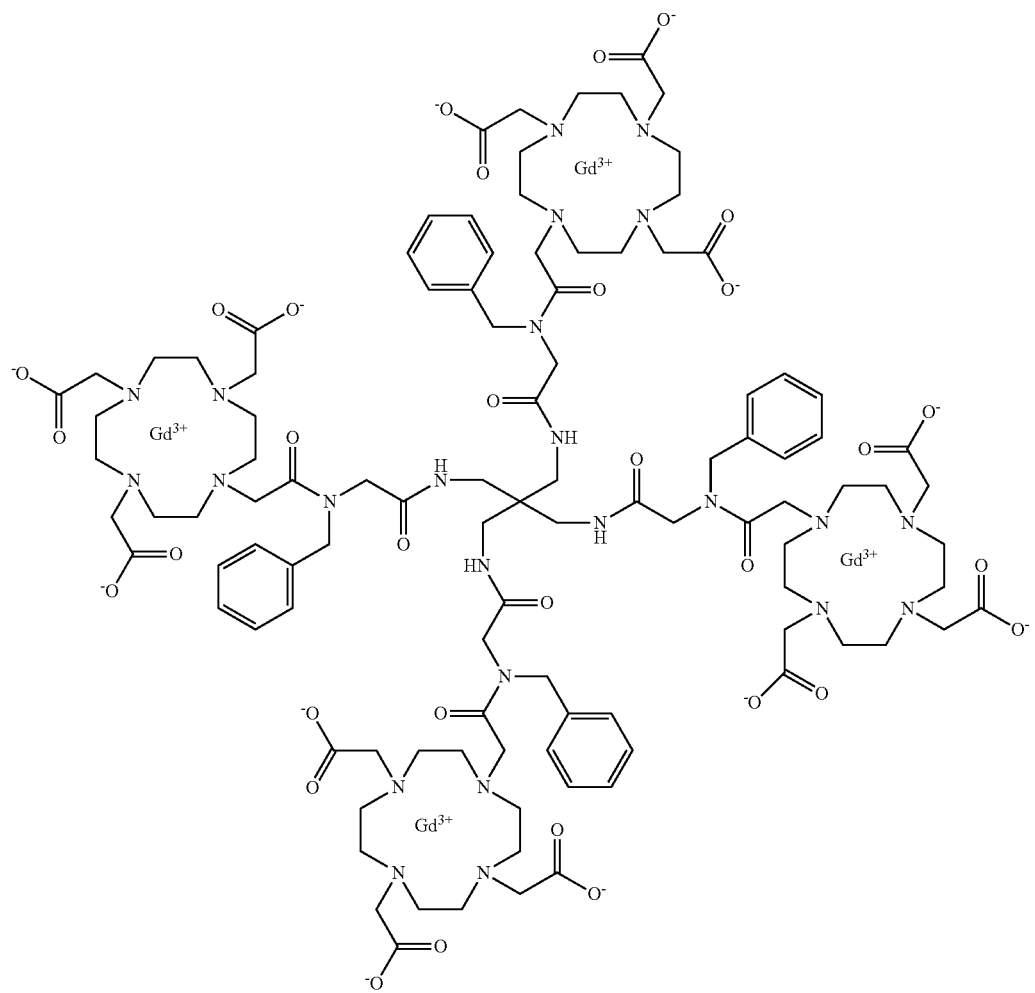

Example 10-1

Tert-butyl N-benzyl-N-{[4,7,10-tris(2-tert-butoxy-2-oxoethyl)-1,4,7,10-tetraazacyclo-dodecan-1-yl]acetyl}glycinate

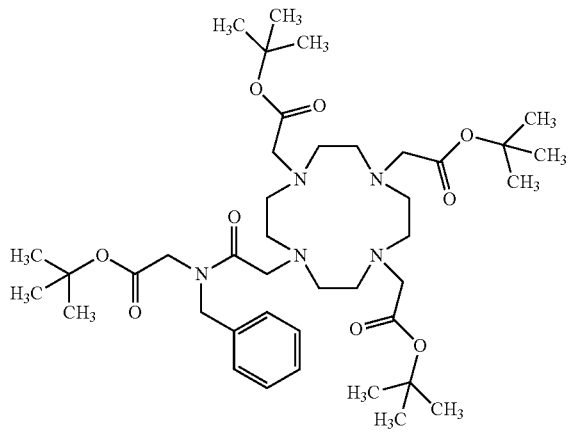 [SMILES: CC(C)(C)OC(=O)CN1CCN(CC(=O)OC(C)(C)C)CCN(CC(=O)N(CC(=O)OC(C)(C)C)Cc2ccccc2)CCN(CC(=O)OC(C)(C)C)CC1]

The compound was synthesized according to the procedure described in example 1-2 starting from 16.00 g (31.09 mmol, 1 eq.) tri-tert-butyl 2,2',2"-(1,4,7,10-tetraazacyclododecane-1,4,7-triyl)triacetate, 12.89 g (93.26 mmol, 3 eq.) potassium carbonate, and 10.64 g (31.09 mmol, 1 eq.) tert-butyl N-benzyl-N-(bromoacetyl)glycinate [see U. Saha et al., THL 36(21), 3635-3638 (1995)] yielding 19.32 g (80%, 24.9 mmol).

$^1$H-NMR (400 MHz, CDCl$_3$): δ=1.29-1.61 (m, 36H), 1.77-5.14 (m, 28H), 7.12-7.40 (m, 5H) ppm.
LC-MS (ES$^+$): m/z=776.6 (M+H)$^+$; R$_t$=1.11 min.

Example 10-2

N-benzyl-N-{[4,7,10-tris(carboxymethyl)-1,4,7,10-tetraazacyclododecan-1-yl]acetyl}glycine

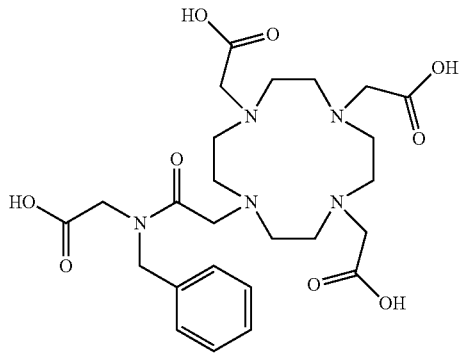 [SMILES: O=C(O)CN1CCN(CC(=O)O)CCN(CC(=O)N(CC(=O)O)Cc2ccccc2)CCN(CC(=O)O)CC1]

The compound was synthesized according to the procedure described in example 1-3 starting from 18.80 g (24.23 mmol) tert-butyl N-benzyl-N-{[4,7,10-tris(2-tert-butoxy-2-oxoethyl)-1,4,7,10-tetraazacyclododecan-1-yl]acetyl}glycinate (example 10-1) in 376 ml formic acid yielding 14.14 g (106%, 25.63 mmol).

$^1$H-NMR (400 MHz, D$_2$O): δ=2.80-4.19 (m, 26H), 4.44-4.58 (m, 2H), 7.12-7.45 (m, 5H) ppm.
LC-MS (ES$^+$): m/z=552.1 (M+H)$^+$; R$_t$=0.49 min.

Example 10-3

Gadolinium 2,2',2"-(10-{2-[benzyl(carboxymethyl)amino]-2-oxoethyl}-1,4,7,10-tetraaza-cyclododecane-1,4,7-triyl)triacetate

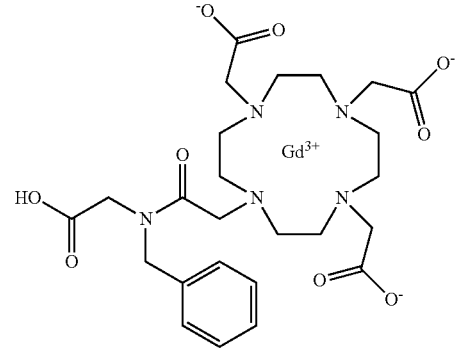

The compound was synthesized according to the procedure described in example 1-4 starting from 14.10 g (25.56 mmol, 1 eq.) N-benzyl-N-{[4,7,10-tris(carboxymethyl)-1,4,7,10-tetraazacyclododecan-1-yl]acetyl}glycine (example 10-2) and 4.17 g (11.50 mmol, 0.45 eq.) gadolinium(III) oxide yielding 17.05 g (85%, 21.74 mmol).

LC-MS (ES$^+$): m/z=707.1 (M+H)$^+$; R$_t$=0.45 and 0.53 min.

Example 10-4

Gadolinium 2,2',2"-[10-(2-{benzyl[2-(4-nitrophenoxy)-2-oxoethyl]amino}-2-oxoethyl)-1,4,7,10-tetraazacyclododecane-1,4,7-triyl]triacetate

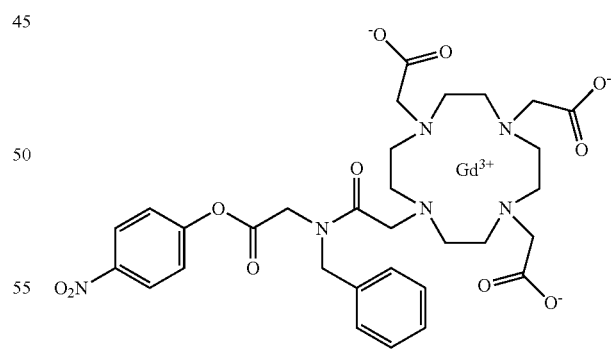

The compound was synthesized according to the procedure described in example 1-5 starting from 6.50 g (9.21 mmol, 1 eq.) gadolinium 2,2',2"-(10-{2-[benzyl(carboxymethyl)amino]-2-oxoethyl}-1,4,7,10-tetraazacyclododecane-1,4,7-triyl)triacetate (example 10-3), 2.56 g (18.42 mmol, 2 eq.) 4-nitrophenol, and 1.74 g (13.81 mmol, 1.5 eq.) N,N'-diisopropyl carbodiimide yielding 6.42 g (84%, 7.76 mmol).

LC-MS (ES$^+$): m/z=828.2 (M+H)$^+$; R$_t$=0.78 min.

Example 10

Tetragadolinium [4,10-bis(carboxylatomethyl)-7-{3,13-dibenzyl-8,8-bis({[(benzyl{[4,7,10-tris(carboxylatomethyl)-1,4,7,10-tetraazacyclododecan-1-yl]acetyl}amino)-acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate The compound was synthesized according to the procedure described in example 1 starting from 191.9 mg (0.69 mmol, 1 eq.) 2,2-bis(ammoniomethyl)propane-1,3-diaminium tetrachloride, 714.0 mg (5.52 mmol, 8 eq.) N,N-diisopropyl ethylamine, and 6.85 g (8.28 mmol, 12 eq.) gadolinium 2,2',2''-[10-(2-{benzyl[2-(4-nitrophenoxy)-2-oxoethyl]amino}-2-oxoethyl)-1,4,7,10-tetraazacyclododecane-1,4,7-triyl]triacetate (example 10-4) yielding 738 mg (35%, 0.24 mmol).

UPLC (ACN-HCOOH): $R_t$=0.61 min.
MS (ES$^+$): m/z (z=2)=1442.6 (M+H)$^{2+}$, m/z (z=3)=961.9 (M+H)$^{3+}$ Reference Compound 1
Gadovist® (gadobutrol, Bayer AG, Leverkusen, Germany)
Reference Compound 2
Magnevist® (gadopentetate dimeglumine, Bayer AG, Leverkusen, Germany)
Reference Compound 3
Primovist® (gadoxetate disodium, Bayer AG, Leverkusen, Germany)
Reference Compound 4
Gadomer-17 was synthesized as described in EP0836485B1, Example 1k.

In Vitro and In Vivo Characterization of Example Compounds

Examples were tested in selected assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from assays represent average values or median values calculated utilizing data sets obtained from testing of one or more synthetic batch.

Example A

Relaxivity Measurements at 1.4 T

Relaxivity measurements at 1.41 T were performed using a MiniSpec mq60 spectrometer (Bruker Analytik, Karlsruhe, Germany) operating at a resonance frequency of 60 MHz and a temperature of 37° C. The $T_1$ relaxation times were determined using the standard inversion recovery (IR) method with a fixed relaxation delay of at least $5 \times T_1$. The variable inversion time (TI) was calculated automatically by the standard software of the MiniSpec mq60 (8 steps). The $T_2$ measurements were done by using a Carr-Purcell-Meiboom-Gill (CPMG) pulse sequence, applying a relaxation delay of at least $5 \times T_1$.

Each relaxivity measurement was performed using three different Gd concentrations (3 concentrations between 0.05 and 2 mM). The $T_1$ and $T_2$ relaxation times of the example compounds 1 to 10 were measured in different media for example in water and human plasma. Human plasma preparation: For each experiment fresh blood was taken from a volunteer using 10 mL citrate-tubes (Sarstedt S-Monovette 02.1067.001, 10 mL, Citrate). The 10 mL citrate-tubes were carefully inverted 10 times to mix blood and anticoagulant and centrifuged for 15 minutes at 1811 g at room temperature (Eppendorf, Centrifuge 5810R).

The relaxivities $r_i$ (where i=1, 2) were calculated on the basis of the measured relaxation rates $R_i$ in water and plasma:

$$R_i = R_{i(0)} + r_i [C_{Gd}],$$

where $R_{i(0)}$ represent the relaxation rate of the respective solvent and $C_{Gd}$ the concentration of the compound normalized to the Gadolinium. The Gadolinium concentrations of the investigated solutions were verified by Inductively Coupled Plasma Mass Spectrometry (ICP-MS Agilent 7500a, Waldbronn, Germany).

The determined relaxivity values are summarized in Table 1.

TABLE 1

Relaxivities of investigated compounds in water and human plasma at 1.41 T and relaxivities of Reference compounds 1-4 (RC1-RC4) at 1.5 T in water. All values were measured at 37° C., are normalized to Gd and given in L mmol$^{-1}$ s$^{-1}$.

| Example No | $r_1$ water* | $r_2$ water* | $r_1$ human plasma* | $r_2$ human plasma* |
| --- | --- | --- | --- | --- |
| 1 | 10.1 | 11.5 | 11.7 | 14.3 |
| 2 | 10.4 | 11.8 | 11.6 | 14.1 |
| 3 | 10.3 | 11.7 | 11.7 | 14.5 |
| 4 | 11.1 | 12.6 | 12.5 | 15.1 |
| 5 | 11.1 | 12.8 | 13.1 | 16.4 |
| 6 | 11.6 | 13.6 | 14.1 | 17.5 |
| 7 | 10.6 | 12.1 | 12.1 | 15.1 |
| 8 | 11.7 | 13.5 | 14.1 | 17.6 |
| 9 | 11.0 | 12.7 | 12.0 | 14.9 |
| 10 | 11.5 | 13.3 | 13.3 | 17.0 |
| RC1^ | 3.3 | 3.9 | 5.2 | 6.1 |
| RC2^ | 3.3 | 3.9 | 4.1 | 4.6 |
| RC3^ | 4.7 | 5.1 | 6.9 | 8.7 |
| RC4^ | 17.3 | 22 | 16 | 19 |

*values are depicted in L mmol$^{-1}$ s$^{-1}$
^Relaxivities from reference compounds from Rohrer et. al. at 1.5 T (Invest. Radiol. 2005; 40, 11: 715-724) and in bovine plasma (Kreaber GmbH, Pharmaceutical Raw Material, Ellerbek, Germany) instead of human plasma Relaxivity Measurements at 3.0 T Relaxivity measurements at 3.0 T were performed with a whole body 3.0 T MRI Scanner (Philips Intera, Philips Healthcare, Hamburg, Germany) using a knee-coil (SENSE-Knee-8, Philips Healthcare, Hamburg, Germany). The sample tubes (CryoTube™ Vials, Thermo Scientific 1.8 mL, Roskilde, Denmark) were positioned in 3 rows of 4 and 5 tubes in a plastic holder in a box filled with water. The temperature was adjusted to 37° C. For the MRI sequence the shortest possible echo-time (TE) with 7.46 milliseconds was used. The inversion times were chosen to optimize the sequence to measure $T_1$ values corresponding to the estimated $T_1$ range of all relaxation times of contrast media containing solutions. The following inversion times (TIs) were applied: 50, 100, 150, 200, 300, 500, 700, 1000, 1400, 2100, 3200, and 4500 milliseconds. The sequence was run with a constant relaxation delay of 3.4 seconds after the registration of the last echo (variable TR in the range from 3450 to 7900 milliseconds). For details of the fit procedure, see Rohrer et.al. (Invest. Radiol. 2005; 40, 11: 715-724). The experimental matrix of the phantom measurement was 320× 320.

The relaxivities were evaluated using three different concentrations of each compound (3 concentrations between 0.05 and 2 mM).

The $T_1$ relaxation times of Example compounds were measured in water and human plasma. Human plasma preparation: For each experiment fresh blood was taken from a volunteer using 10 mL citrate-tubes (Sarstedt S-Monovette 02.1067.001, 10 mL, Citrate). The 10 mL citrate-tubes were carefully inverted 10 times to mix blood and anticoagulant and centrifuged for 15 minutes at 1811 g at room temperature (Eppendorf, Centrifuge 5810R).

The relaxivities $r_i$ (where i=1, 2) were calculated on the basis of the measured relaxation rates $R_i$ in water and plasma:

$$R_i = R_{i(0)} + r_i[C_{Gd}],$$

where $R_{i(0)}$ represent the relaxation rate of the respective solvent and $C_{Gd}$ the concentration of the compound normalized to the Gadolinium (Table 2).

TABLE 2

Relaxivities (normalized to Gd) in water and human plasma at 3.0 T and 37° C. [L mmol$^{-1}$ s$^{-1}$]

| Example No | $r_1$ water* | $r_1$ human plasma* |
|---|---|---|
| 1 | 9.1 ± 0.1 | 10.3 ± 0.2 |
| 2 | 9.4 ± 0.1 | 11.3 ± 0.1 |
| 3 | 9.5 ± 0.1 | 10.9 ± 0.1 |
| 4 | 10.1 ± 0.2 | 11.3 ± 0.01 |
| 5 | 10.2 ± 0.1 | 11.6 ± 0.4 |
| 7 | 9.7 ± 0.1 | 11.1 ± 0.1 |

TABLE 2-continued

Relaxivities (normalized to Gd) in water and human plasma at 3.0 T and 37° C. [L mmol$^{-1}$ s$^{-1}$]

| Example No | $r_1$ water* | $r_1$ human plasma* |
|---|---|---|
| 8 | 10.7 ± 0.1 | 12.0 ± 0.4 |
| RC1^ | 3.2 ± 0.3 | 5.0 ± 0.3 |
| RC2^ | 3.1 ± 0.3 | 3.7 ± 0.2 |
| RC3^ | 4.3 ± 0.3 | 6.2 ± 0.3 |
| RC4^ | 13.0 ± 0.7 | 13 ± 1 |

*Average ± standard deviation, values are depicted in L mmol$^{-1}$ s$^{-1}$
n.d. = not determined Example B Pharmacokinetic Parameters Pharmacokinetic parameters of Example 6 were determined in male rats (Han-Wistar, 235-270 g, n=3). The compound was administered as a sterile aqueous solution (53.8 mmol Gd/L) as a bolus in the tail vein of the animals. The dose was 0.1 mmol Gd/kg. Blood was sampled 1, 3, 5, 10, 15, 30, 60, 90, 120, 240, 360, 480, and 1440 min post injection and the Gd concentration was determined by Inductively Coupled Plasma Mass Spectrometry (ICP-MS Agilent 7500a, Waldbronn, Germany). The blood level was converted to plasma concentrations by division by 0.625 (plasma fraction of rat blood, assuming strictly extracellular distribution). As a control, 3 animals (Han-Wistar, 248-289 g), were treated in the same way with Reference Compound 1 (Gadovist®), a low molecular weight contrast agent.

The fit of the obtained data to a three compartment model (Phoenix-WinNonlin) yielded the pharmacokinetic parameters which are shown in Table 3.

The pharmacokinetic of example Example 6 is very similar to that of the reference compound 1.

TABLE 3

Pharmacokinetic parameters of blood plasma levels

| | Parameter | unit | Example 6 mean | Example 6 SD | Reference Compound 1 mean | Reference Compound 1 SD |
|---|---|---|---|---|---|---|
| t½ α | Half-life, compartment V1 | [min] | 2.45 | 0.84 | 1.80 | 0.3 |
| t½ β | Half-life, compartment V2 | [min] | 22.4 | 2.6 | 22.1 | 2.1 |
| t½ γ | Half-life, compartment V3 | [min] | 1041 | 202 | 780 | 187 |
| MRT | Mean residence time | [min] | 40.7 | 5.4 | 40.5 | 4.2 |
| AUC∞ | Area under the curve (to infinity) | [μmol/l * min] | 10801 | 1170 | 11334 | 1346 |
| $V_c$ (V1) | Volume, central compartment V1 | [l/kg] | 0.98% | 0.11% | 1.16% | 0.20% |
| V2 | Volume, compartment V2 | [l/kg] | 0.12 | 0.02 | 0.16 | 0.03 |
| V1 + V2 | Volume, compartments V1 + V2 | [l/kg] | 0.14 | 0.03 | 0.11 | 0.01 |
| $V_{d,ss}$ | Volume of distribution at steady state | [l/kg] | 0.27 | 0.01 | 0.26 | 0.02 |
| $Cl_{tot}$ | Total Clearance | [ml/min * kg] | 0.40 | 0.02 | 0.38 | 0.03 |

Example C

Chemical Stability

Example 1 was separately dissolved in 10 mMTris-HCl buffer, pH7.4 at a final concentration of 5 mmol Gd/L. An aliquot was removed and the rest of the clear and colorless solution was autoclaved at 121° C. for 20 min. After autoclaving, the solution was still clear and colorless. The aliquot removed before and after autoclaving was analyzed by HPLC-ICP-MS to determine the integrity of the compound.

HPLC: Column: Hypercarb 2.5 mm×15 cm. Solvent A: 0.1% formic acid in water. Solvent B: acetonitrile. Gradient from 100% A to 5% A+95% B in 10 min. Flow 1 ml/min. Detection by ICP-MS, tuned to $^{158}$Gd. The chromatograms, displaying the intensity of the detected Gd, were visually compared. No changes in the chromatograms before and after autoclaving were detected. The compound was stable during the autoclaving procedure.

Example 0D

Gd-Complex Stabilities in Human Plasma at 37° C. 15 d

Example 1 was separately dissolved in human plasma at 1 mmol Gd/L. As a reference for released $Gd^{3+}$ 0.1 mmol/L Gadolinium chloride ($GdCl_3$) was dissolved in human plasma. The plasma samples were incubated for 15 days at 37° C. under 5% $CO_2$ atmosphere to maintain the pH at 7.4. Aliquots were taken at the start and end of the incubation. The amount of $Gd^{3+}$ released from the complexes was determined by HPLC-ICP-MS. Column: Chelating Sepharose (HiTrap, 1 mL). Solvent A: 10 mM BisTris-HCl pH 6.0. Solvent B: 15 mM $HNO_3$. Gradient: 3 min at 100% A, from 3 to 10 min at 100% B. Flow 1 mL/min. Detection by ICP-MS, tuned to $^{158}$Gd. The chromatograms, displaying the intensity of the detected Gd, were evaluated by peak area analysis. The size of the peak of $Gd^{3+}$*, eluting after the change from solvent A to B, was recorded. For Example 1 the increase of this peak and thus the release of $Gd^{3+}$ after 15 days was below the limit of quantification (<0.1% of the injected total amount of Gadolinium). Example 1 is stable under physiological conditions.

Example E

Water Solubility

The exploratory water solubilities of the compounds were determined at room temperature (20° C.) in 0.5 mL buffer solution (10 mM Tris-HCl) in the microcentrifuge tubes (Eppendorf, 2.0 mL safe-lock caps). The solid compounds were added stepwise to the buffer solution. The suspension was mixed using a shaker (Heidolph Reax 2000) and treated 5 min in an ultrasound bath (Bandelin, Sonorex Super RK255H). The results are summarized in Table 4.

TABLE 4

| Solubilities of compounds in water at 20° C. (pH 7.4). | |
|---|---|
| Example No | Solubility [mg/100 mL] |
| 1 | >1000 |
| 2 | >1000 |
| 3 | >1000 |
| 4 | >1000 |
| 5 | >1000 |
| 6 | >1000 |

TABLE 4-continued

| Solubilities of compounds in water at 20° C. (pH 7.4). | |
|---|---|
| Example No | Solubility [mg/100 mL] |
| 7 | >1000 |
| 8 | >1000 |
| 9 | >1000 |
| 10 | >1000 |

Example F

Contrast-Enhanced Magnetic Resonance Angiography (CE-MRA)

The potential of a significant dose reduction in CE-MRA was shown by an intraindividual comparison of 100 μmol Gadolinium per kilogram body weight [100 μmol Gd/kg bw], which is comparable to the human standard dose and a low dose protocol using 25 μmol Gadolinium per kilogram body weight in an animal model. Reference compound 1 (Gadovist), as an approved representative of the Gadolinium-based MRI contrast agents, was used in both dose protocols (100 μmol Gd/kg bw and 25 μmol Gd/kg bw) and compared to example compound 6 (25 μmol Gd/kg bw).

The contrast-enhanced magnetic resonance angiography study was performed at a clinical 1.5 T Scanner (Magnetom Avanto Fit, Siemens Healthcare, Erlangen, Germany). For optimal signal exploitation, a spine in combination with a body-flex coil was used for the data acquisition. The study was performed on male New Zealand white rabbits (weight 3.6-3.9 kg, n=4, Charles River Kisslegg). The animals received all 3 contrast protocols within one imaging session. The order of the contrast protocols was randomized between the animals.

All animals are initially anesthetized using a body weight-adjusted intramuscular injection of a mixture (1+2) of xylazine hydrochloride (20 mg/mL, Rompun 2%, Bayer Vital GmbH, Leverkusen, Germany) and ketamine hydrochloride (100 mg/mL, Ketavet, Pfizer, Pharmacia GmbH, Berlin, Germany) using 1 mL/kg body weight. The continuous anesthesia of the intubated animals (endotracheal tube, Rueschelit Super Safe Clear, cuff 3.0 mm, Willy Ruesch AG, Kernen, Germany) is achieved by the intravenous injection of 0.9 mg propofol per kilogram per hour (10 mg/mL, Propofol-Lipuro 1%, B. Braun Melsungen AG, Melsungen, Germany). The continuous intravenous injection is performed using a MR infusion system (Continuum MR Infusion System, Medrad Europe B. V., AE Beek, Germany). The tracheal respiration (SV 900C, Maquet, Rastatt, Germany) is performed with 55% oxygen, forty breaths per minute, and a breathing volume of 4 mL per kilogram body weight per minute.

Based on a localizer MRI sequence oriented in coronal, axial, and sagittal directions the anatomic course of the aorta is acquired. A small intravenous test bolus (0.2 mL, Reference compound 1 followed by 1.3 mL saline) was administered to determine the time to peak interval (descending aorta) using a test bolus sequence. The MRA delay time between the start of the contrast injection and the start of image acquisition was calculated by subtracting the time to k-space center from the time to peak interval. For MRA a 3D FLASH sequence (TR=3.3 ms, TE=1.2 ms, flip=25°) was acquired before and after injection of the contrast agent considering the delay time. Both measurements were performed within expiratory breath hold. The time interval for the intraindividual comparison between the different contrast agent applications was twenty to thirty minutes.

Figure 3:
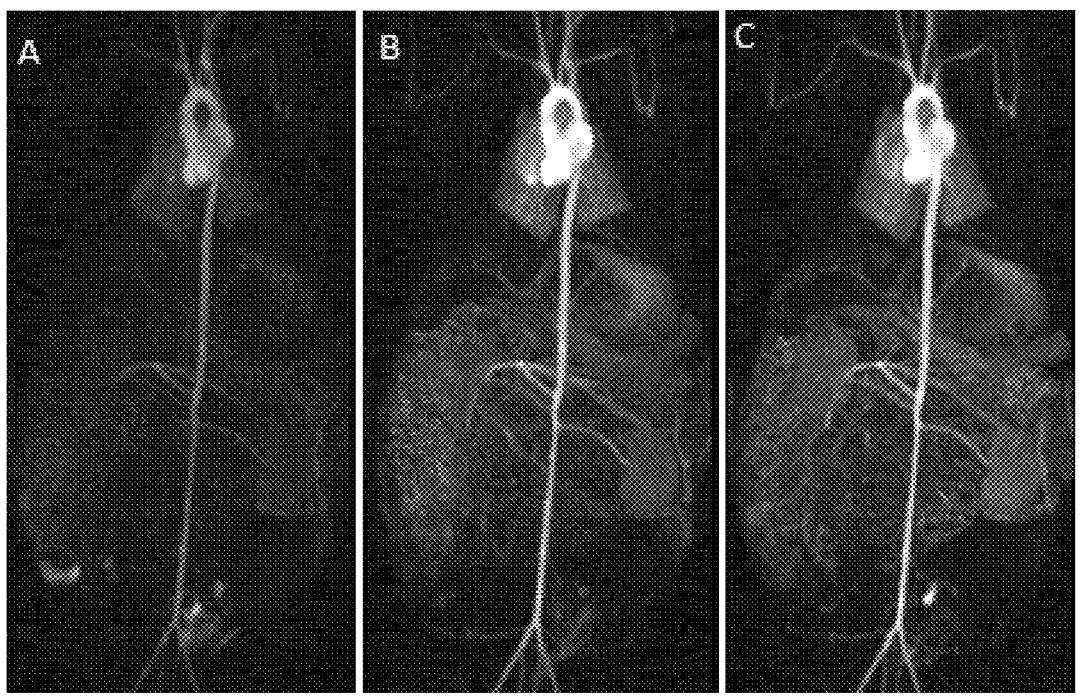

FIG. 3 displays representative MR-Angiograms (maximum intensity projection) for

B (middle): example compound 6 at 25 µmol/kg, compared to

C (right): reference compound 1 (Gadovist) at standard dose (100 µmol/kg), and

A (left) reference compound 1 (Gadovist) at reduced dose (25 µmol/kg).

No qualitative difference in the vascular contrast was found for the example compound 6 at 25 µmol/kg compared to the reference compound 1 at 100 µmol/kg. The vascular contrast at the reduced dose of the reference compound is considerable lower.

Quantitative image evaluation was performed on the subtraction images (post contrast-baseline). Regions of interest were placed in the carotid artery (left and right), the ascending aorta, the descending aorta (thoracic level, liver level, kidney level, bifurcation level), and the renal arteries (left and right).

The respective signal enhancements for all regions are shown in FIG. 4. For the example compound 6 similar signal enhancements were found at 25% of the dose of the reference compound 1. At identical doses the signal enhancement of the example compound 6 was significantly higher. That demonstrated the high efficacy of example compound 6 and the potential for significant dose reduction in contrast enhance MRA.

Example G

Dynamic CT Diffusion Phantom Study

As indicated in Example A the Reference compound 4 has a relaxivity which is in a similar range as the compounds of the present invention. Following intravenous injection, all clinically approved small monomer GBCAs (gadopentetate dimeglumine, gadoterate meglumine, gadoteridol, gadodiamide, gadobutrol, and gadoversetamide) distribute in the blood and extravascular/extracellular space by passive distribution (Aime S et. al., J. Magn. Reson. Imaging. 2009; 30, 1259-1267). Contrast agents with a high protein binding, for example gadofosveset trisodium with a prolonged period in the blood vessels caused by the reversible binding to HSA, or large hydrodynamic sizes as for example Reference compound 4 are hindered to pass the vessel wall. For good imaging results a fast diffusion through the vessel walls is required due to the fast renal excretion of GBCAs.

The described dynamic CT diffusion study compares the ability of Examples 1-10 and Reference compounds 1 and 4 to pass a semipermeable membrane (20 kDa). A 128-row clinical CT device (SOMATOM Definition, 128; Siemens Healthcare, Forchheim, Germany) was used to monitor the diffusion through a semipermeable membrane at 100 kV and 104 mA. Single measurements were performed at 0 min, 1 min, 2 min, 3 min, 5 min, 10 min, 15 min, 20 min, 30 min, 45 min, 60 min, 2 h, 3 h, 5 h, 7 h, 22 h, 24 h, 30 h after placing the dialysis cassette (Slide-A-Lyser, 20,000 MWCO, 0.1-0.5 mL Capacity, Thermo Scientific, Roskilde, Denmark) filled with contrast agent in fetal bovine serum solution (FBS, Sigma, F7524). The images were reconstructed with a slice thickness of 2.4 mm and a B30 convolution kernel. The used concentration in the dialysis cassettes of the investigated Examples 1-10 and Reference compounds 1 and 4 was 20 mmol Gd/L.

Figure 1:
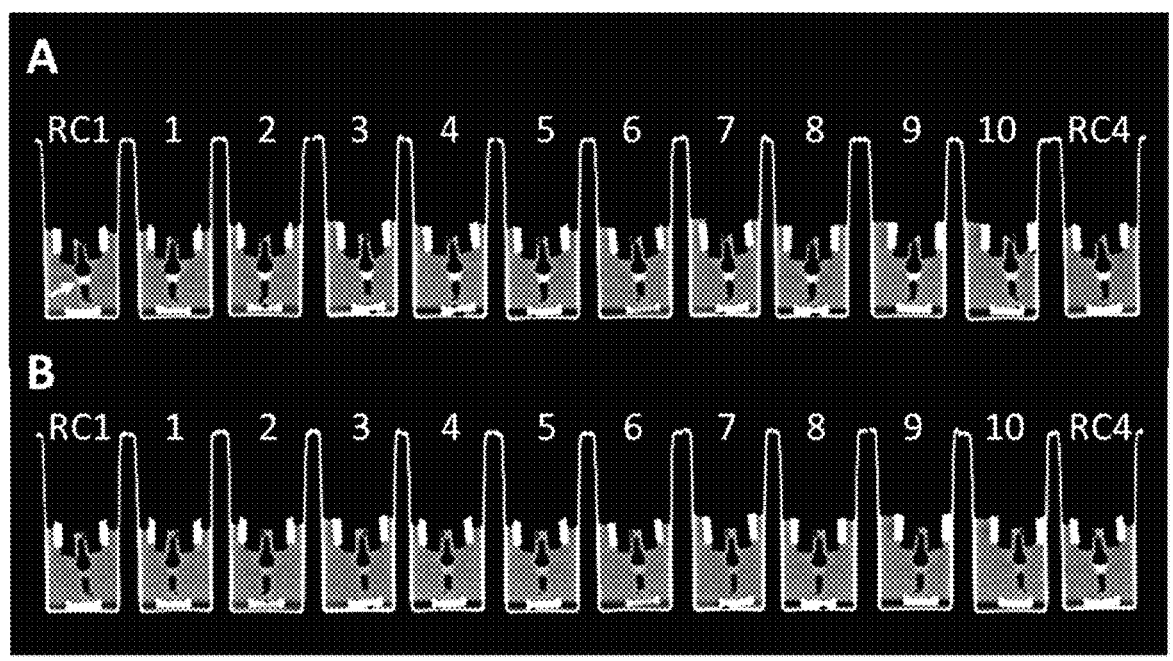
FIG. 1 Diffusion of different contrast agents through semipermeable membranes (20 kDa). Dynamic CT measurements were performed to show the ability of different contrast agents to diffuse through a semipermeable membrane. (A) CT images of Example 1-10 in comparison to that of Reference compound 1 (Gadovist®) and 4 (Gadomer). A representative measurement region for the signal evaluation overtime is indicated in the image RC1. (B) CT images of Example 1-10 in comparison to that of Reference compound 1 (Gadovist®) and 4 (Gadomer) after 30 h.
Figure 2:
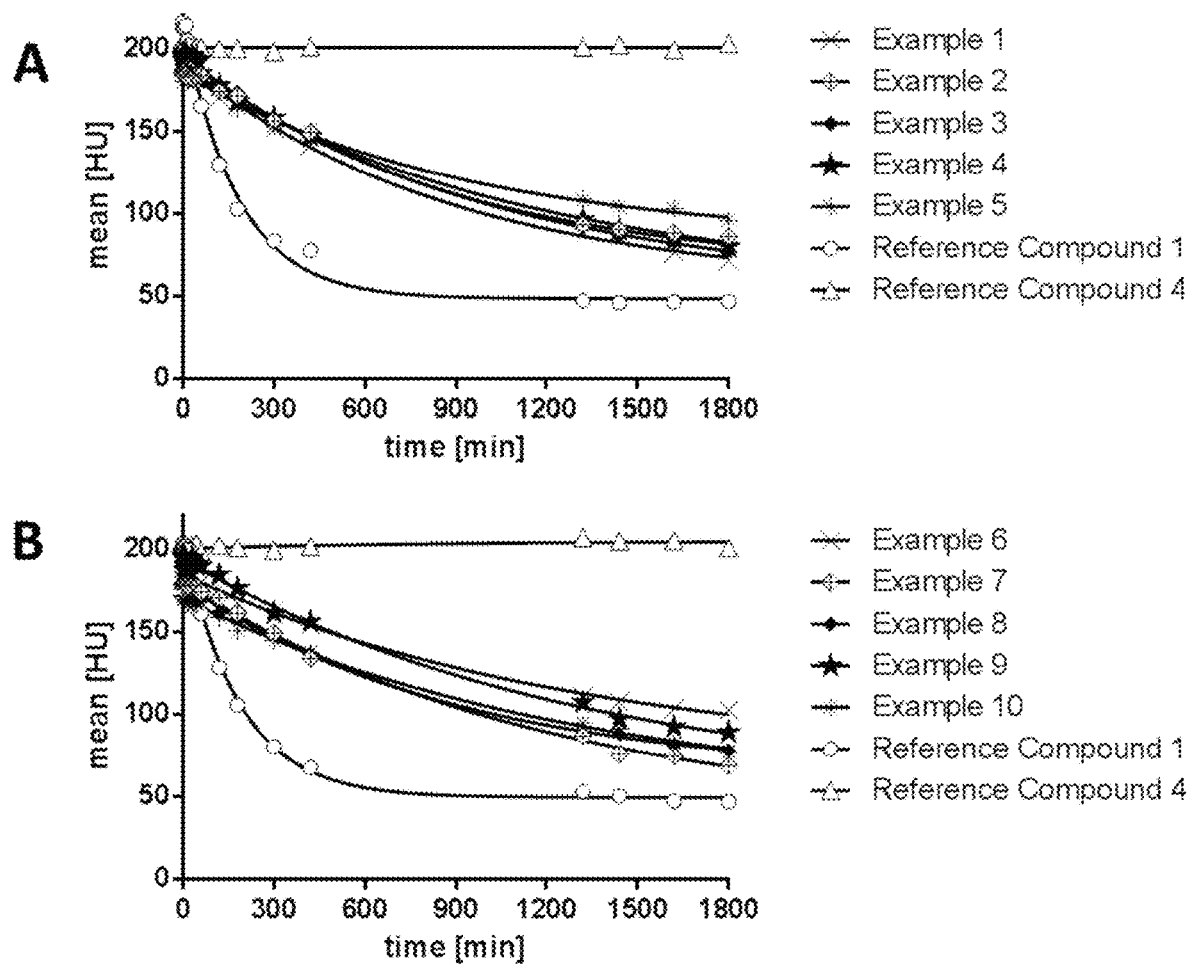
FIG. 2 Signal analysis of dynamic CT diffusion phantom study over time. Signal in Hounsfield units (HU) over time of the dialysis cassette in fetal bovine solution for (A) Example 1-5 and (B) for Example 6-10 compared with Reference compounds 1 and 4. The results demonstrate that contrary to Reference compound 4 (Gadomer) all of the investigated compounds are able to pass the semipermeable membrane (20 kDa).

The imaging results for all investigated Examples and the Reference compounds 1 and 4 for the time points 0 min and 30 h after placing the cassettes in the FBS solution are depicted in FIG. 1. For image analysis, regions of interest were manually drawn on 1 centrally located slice for each time point (a representative measurement region is indicated in FIG. 1: Image RC1). The results of the Hounsfield units (HU) of the analyzed regions over time are shown in FIG. 2. The calculated diffusion half-lifes of the investigated Examples and Reference compounds are summarized in Table 4.

TABLE 4

| Diffusion half-live through a semipermeable membrane (20 kDa) | |
| --- | --- |
| Example No | Diffusion half-live (20 kDa) [h] |
| 1 | 10.4 |
| 2 | 13.3 |
| 3 | 11.6 |
| 4 | 10.1 |
| 5 | 10.8 |
| 6 | 15.0 |
| 7 | 14.0 |
| 8 | 10.5 |
| 9 | 15.1 |
| 10 | 15.0 |
| RC 1 | 2.1 |
| RC 4 | No diffusion |

The FIG. 1 and the calculated half-life data show, similar to the Reference compound 1 (Gadovist®) and in contrast to the Reference compound 4, that the Examples 1-10 are able to pass the semipermeable membrane. Furthermore the data of the investigated compounds show contrary to other high relaxivity agents, which have a high protein binding or very slow tumbling rates (e.g. Reference compound 4), that the compounds of the present invention have hydrodynamic dimensions which can overcome barriers in a timely manner. These findings indicate the ability of the compounds of the invention to overcome barriers as for example endothelial walls in the vascular system, which is a requirement for whole body imaging.

We claim:

1. An aqueous pharmaceutical solution comprising a tetrameric gadolinium compound of general formula (I),

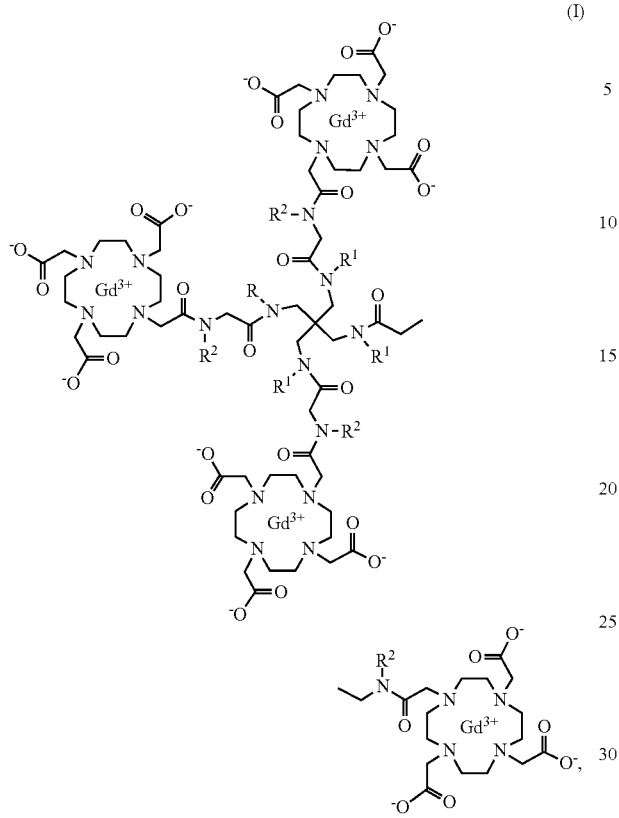

wherein:
R¹ represents, independently from each other, a hydrogen atom or a methyl group;
R² represents, independently from each other, a substituent selected from the group consisting of:
$C_1$-$C_6$-alkyl, $C_3$-$C_6$-cycloalkyl, $C_2$-$C_6$-hydroxyalkyl, ($C_1$-$C_3$-alkoxy)-($C_2$-$C_4$-alkyl)-, 2-(2-methoxyethoxy)ethyl, 2-(2-ethoxyethoxy)ethyl, oxetan-3-yl, tetrahydro-2H-pyran-4-yl, and phenyl,
  wherein said $C_1$-$C_6$-alkyl group is optionally substituted, identically or differently, with a phenyl group, wherein the phenyl group is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy, and
  wherein when R² represents phenyl, the phenyl is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

2. The aqueous pharmaceutical solution according to claim 1, wherein:
R¹ represents a hydrogen atom;
R² represents a substituent selected from the group consisting of:
$C_1$-$C_6$-alkyl, $C_3$-$C_6$-cycloalkyl, $C_2$-$C_4$-hydroxyalkyl, ($C_1$-$C_3$-alkoxy)-($C_2$-$C_4$-alkyl)-, oxetan-3-yl, tetrahydro-2H-pyran-4-yl, and phenyl,
  wherein said $C_1$-$C_6$-alkyl group is optionally substituted, identically or differently, with a phenyl group, wherein the phenyl group is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy, and
  wherein when R² represents phenyl, the phenyl is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

3. The aqueous pharmaceutical solution according to claim 1, wherein:
R¹ represents a hydrogen atom;
R² represents a substituent selected from the group consisting of:
$C_1$-$C_6$-alkyl, $C_3$-$C_6$-cycloalkyl, ($C_1$-$C_3$-alkoxy)-($C_2$-$C_4$-alkyl)-, and phenyl,
  wherein said $C_1$-$C_6$-alkyl group is optionally substituted, identically or differently, with a phenyl group, wherein the phenyl group is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy, and
  wherein when R² represents phenyl, the phenyl is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

4. The aqueous pharmaceutical solution according to claim 1, wherein:
R¹ represents a hydrogen atom;
R² represents a substituent selected from the group consisting of:
$C_1$-$C_4$-alkyl, $C_3$-$C_5$-cycloalkyl, ($C_1$-$C_2$-alkoxy)-($C_2$-$C_3$-alkyl)-, and phenyl,
  wherein said $C_1$-$C_4$-alkyl group is optionally substituted, identically or differently, with a phenyl group, wherein the phenyl group is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy, and
  wherein when R² represents phenyl, the phenyl is optionally substituted, one, two, or three times, identically or differently, with a halogen atom or a group selected from:
   $C_1$-$C_3$-alkyl, $C_1$-$C_3$-haloalkyl, and $C_1$-$C_3$-alkoxy;
or a stereoisomer, a tautomer, an N-oxide, a hydrate, a solvate, or a salt thereof, or a mixture of same.

5. The aqueous pharmaceutical solution according to claim 1, wherein:
R¹ represents a hydrogen atom;
R² represents a substituent selected from the group consisting of:
methyl, ethyl, isopropyl, 2-methylpropyl, benzyl, cyclopropyl, cyclopentyl, 2-methoxyethyl, 2-ethoxyethyl, and phenyl,
or a stereoisomer, a tautomer, an N-oxide, a hydrate, a solvate, or a salt thereof, or a mixture of same.

6. The aqueous pharmaceutical solution according to claim 1, wherein the compound has a structure selected from the group consisting of:

Tetragadolinium [4,10-bis(carboxylatomethyl)-7-{3,13-dimethyl-8,8-bis({[(methyl{[4,7,10-tris(carboxylatomethyl)-1,4,7,10-tetraazacyclododecan-1-yl]acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{3,13-diethyl-8,8-bis({[(ethyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl]acetate, Tetragadolinium {4,10-bis(carboxylatomethyl)-7-[15-(2-methoxyethyl)-10,10-bis[({[(2-methoxyethyl){[4,7,10-tris(carboxylatomethyl)-1,4,7,10-tetraazacyclododecan-1-yl]-acetyl}amino]acetyl}amino)methyl]-7,13,16-trioxo-5-{[4,7,10-tris(carboxylatomethyl)-1,4,7,10-tetraazacyclododecan-1-yl]acetyl}-2-oxa-5,8,12,15-tetraazaheptadecan-17-yl]-1,4,7,10-tetraazacyclododecan-1-yl}acetate, Tetragadolinium {4,10-bis(carboxylatomethyl)-7-[16-(2-ethoxyethyl)-11,11-bis[({[(2-ethoxyethyl){[4,7,10-tris(carboxylatomethyl)-1,4,7,10-tetraazacyclododecan-1-yl]-acetyl}amino]acetyl}amino)methyl]-8,14,17-trioxo-6-{[4,7,10-tris(carboxylatomethyl)-1,4,7,10-tetraazacyclododecan-1-yl]acetyl}-3-oxa-6,9,13,16-tetraazaoctadecan-18-yl]-1,4,7,10-tetraazacyclododecan-1-yl}acetate, Tetragadolinium [4,10-bis(carboxylatomethyl)-7-{3,13-diisopropyl-8,8-bis({[(isopropyl-{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraaza-cyclododecan-1-yl]-3,6,10,13-tetraazapentadec-1-yl}-1,4,7,10-tetraazacyclododecan-1-yl]acetate, Tetragadolinium {4,10-bis(carboxylatomethyl)-7-[3-isobutyl-8,8-bis({[(isobutyl{[4,7,10-tris(carboxylatomethyl)-1,4,7,10-tetraazacyclododecan-1-yl]acetyl}amino)acetyl]amino}-methyl)-15-methyl-2,5,11-trioxo-13-{[4,7,10-tris(carboxylatomethyl)-1,4,7,10-tetraaza-cyclododecan-1-yl]acetyl}-3,6,10,13-tetraazahexadec-1-yl]-1,4,7,10-tetraazacyclododecan-1-yl}acetate, Tetragadolinium [4,10-bis(carboxylatomethyl)-7-{3,13-dicyclopropyl-8,8-bis({[(cyclopropyl{[4,7,10-tris(carboxylatomethyl)-1,4,7,10-tetraazacyclododecan-1-yl]acetyl}amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{3,13-dicyclopentyl-8,8-bis({[(cyclopentyl{[4,7,10-tris(carboxylatomethyl)-1,4,7,10-tetraazacyclododecan-1-yl]acetyl}amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{2,5,11,14-tetraoxo-3,13-diphenyl-8,8-bis({[(phenyl{[4,7,10-tris(carboxylatomethyl)-1,4,7,10-tetraazacyclododecan-1-yl]acetyl}-amino)acetyl]amino}methyl)-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, and Tetragadolinium [4,10-bis(carboxylatomethyl)-7-{3,13-dibenzyl-8,8-bis({[(benzyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl], acetate, or a stereoisomer, a tautomer, an N-oxide, a hydrate, a solvate, or a salt thereof, or a mixture of same.

7. A method of preparing an aqueous pharmaceutical solution of a compound of general formula (I) where $R^1$ and $R^2$ are as defined in claim 1, the method comprising:

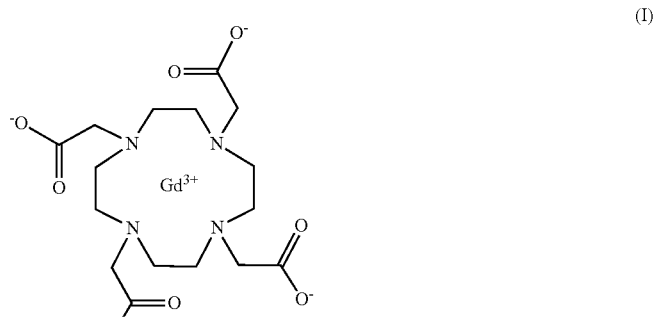

(I)

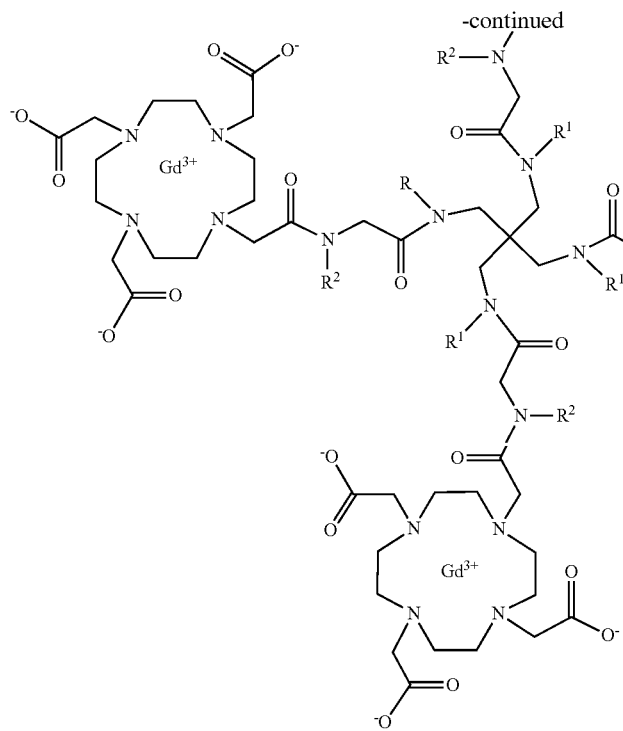
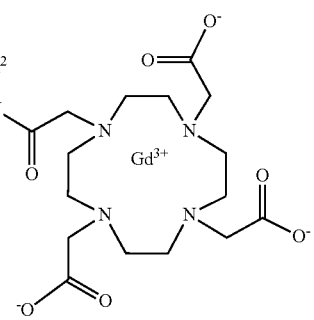

dissolving the compound of general formula (I) in a sufficient volume of a 10 mM Tris-HCl buffer solution to provide the aqueous pharmaceutical solution having a pH of 7.4 and a final concentration of gadolinium of 5 mmol Gd/L.

8. The method of claim 7, wherein the compound of general formula (I) has a structure selected from the group consisting of:

Tetragadolinium [4,10-bis(carboxylatomethyl)-7-{3,13-dimethyl-8,8-bis({[(methyl {[4,7,10-tris(carboxylatomethyl)-1,4,7,10-tetraazacyclododecan-1-yl]acetyl}amino) acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{3,13-diethyl-8,8-bis({[(ethyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl]acetate, Tetragadolinium {4,10-bis(carboxylatomethyl)-7-[15-(2-methoxyethyl)-10,10-bis[({[(2-methoxyethyl){[4,7,10-tris(carboxylatomethyl)-1,4,7,10-tetraazacyclododecan-1-yl]-acetyl}amino]acetyl}amino)methyl]-7,13,16-trioxo-5-{[4,7,10-tris(carboxylatomethyl)-1,4,7,10-tetraazacyclododecan-1-yl]acetyl}-2-oxa-5,8,12,15-tetraazaheptadecan-17-yl]-1,4,7,10-tetraazacyclododecan-1-yl}acetate, Tetragadolinium {4,10-bis(carboxylatomethyl)-7-[16-(2-ethoxyethyl)-11,11-bis[({[(2-ethoxyethyl){[4,7,10-tris(carboxylatomethyl)-1,4,7,10-tetraazacyclododecan-1-yl]-acetyl}amino]acetyl}amino)methyl]-8,14,17-trioxo-6-{[4,7,10-tris(carboxylatomethyl)-1,4,7,10-tetraazacyclododecan-1-yl]acetyl}-3-oxa-6,9,13,16-tetraazaoctadecan-18-yl]-1,4,7,10-tetraazacyclododecan-1-yl}acetate, Tetragadolinium [4,10-bis(carboxylatomethyl)-7-{3,13-diisopropyl-8,8-bis({[(isopropyl-{[4,7,10-tris(carboxylatomethyl)-1,4,7,10-tetraazacyclododecan-1-yl]acetyl}amino)acetyl]-amino}methyl)-2,5,11,14-tetraoxo-15-[4,7,10-tris(carboxylatomethyl)-1,4,7,10-tetraaza-cyclododecan-1-yl]-3,6,10,13-tetraazapentadec-1-yl]-1,4,7,10-tetraazacyclododecan-1-yl]acetate, Tetragadolinium {4,10-bis(carboxylatomethyl)-7-[3-isobutyl-8,8-bis({[(isobutyl{[4,7,10-tris(carboxylatomethyl)-1,4,7,10-tetraazacyclododecan-1-yl]acetyl}amino)acetyl]amino}-methyl)-15-methyl-2,5,11-trioxo-13-{[4,7,10-tris(carboxylatomethyl)-1,4,7,10-tetraaza-cyclododecan-1-yl]acetyl}-3,6,10,13-tetraazahexadec-1-yl]-1,4,7,10-tetraazacyclododecan-1-yl}acetate, Tetragadolinium [4,10-bis(carboxylatomethyl)-7-{3,13-dicyclopropyl-8,8-bis({[(cyclopropyl{[4,7,10-tris(carboxylatomethyl)-1,4,7,10-tetraazacyclododecan-1-yl]acetyl}amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{3,13-dicyclopentyl-8,8-bis({[(cyclopentyl{[4,7,10-tris(carboxylatomethyl)-1,4,7,10-tetraazacyclododecan-1-yl]acetyl}amino)acetyl]amino}methyl)-2,5,11,14-tetraoxo-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, Tetragadolinium [4,10-bis(carboxylatomethyl)-7-{2,5,11,14-tetraoxo-3,13-diphenyl-8,8-bis({[(phenyl{[4,7,10- tris(carboxylatomethyl)-1,4,7,10-tetraazacyclododecan-1-yl]acetyl}-amino)acetyl]amino}methyl)-15-[4,7,10-tris(carboxylatomethyl)-1,4,7,10-tetraazacyclododecan-1-yl]-3,6,10,13-tetraazapentadec-1-yl}-1,4,7,10-tetraazacyclododecan-1-yl]acetate, and Tetragadolinium [4,10-bis(carboxylatomethyl)-7-{3,13-dibenzyl-8,8-bis({[(benzyl{[4,7,10-tris(carboxylatomethyl)-1,4,7,10-tetraazacyclododecan-1-yl]acetyl}amino)acetyl]amino}-methyl)-2,5,11,14-tetraoxo-15-[4,7,10-tris(carboxylatomethyl)-1,4,7,10-tetraazacyclo-dodecan-1-yl]-3,6,10,13-tetraazapentadec-1-yl}-1,4,7,10-tetraazacyclododecan-1-yl], acetate, or a stereoisomer, a tautomer, an N-oxide, a hydrate, a solvate, or a salt thereof, or a mixture of same.

9. A method of imaging body tissue in a mammal, comprising:

administering to the mammal an effective amount of the aqueous pharmaceutical solution according to claim 1 in an amount sufficient to provide from 25 µmol Gadolinium per kilogram body weight and 100 µmol Gadolinium per kilogram body weight; and subjecting the mammal to magnetic resonance imaging.

10. A compound having a structure selected from the group consisting of:

Gadolinium 2,2',2"-(10-{2-[(carboxymethyl)(methyl)amino]-2-oxoethyl}-1,4,7,10-tetra-azacyclododecane-1,4,7-triyl)triacetate;

Gadolinium 2,2',2"-(10-{2-[(carboxymethyl)(ethyl)amino]-2-oxoethyl}-1,4,7,10-tetra-azacyclododecane-1,4,7-triyl)triacetate;

Gadolinium 2,2',2"-(10-{2-[(carboxymethyl)(2-methoxyethyl)amino]-2-oxoethyl}-1,4,7,10-tetraazacyclododecane-1,4,7-triyl)triacetate;

Gadolinium 2,2',2"-(10-{2-[(carboxymethyl)(2-ethoxyethyl)amino]-2-oxoethyl}-1,4,7,10-tetraazacyclododecane-1,4,7-triyl)triacetate;

Gadolinium 2,2',2"-(10-{2-[(carboxymethyl)(isopropyl)amino]-2-oxoethyl}-1,4,7,10-tetra-azacyclododecane-1,4,7-triyl)triacetate;

Gadolinium 2,2',2"-(10-{2-[(carboxymethyl)(isobutyl)amino]-2-oxoethyl}-1,4,7,10-tetra-azacyclododecane-1,4,7-triyl)triacetate;

Gadolinium 2,2',2"-(10-{2-[(carboxymethyl)(cyclopropyl)amino]-2-oxoethyl}-1,4,7,10-tetraazacyclododecane-1,4,7-triyl)triacetate;

Gadolinium 2,2',2"-(10-{2-[(carboxymethyl)(cyclopentyl)amino]-2-oxoethyl}-1,4,7,10-tetraazacyclododecane-1,4,7-triyl)triacetate;

Gadolinium 2,2',2"-(10-{2-[(carboxymethyl)(phenyl)amino]-2-oxoethyl}-1,4,7,10-tetra-azacyclododecane-1,4,7-triyl)triacetate; and Gadolinium 2,2',2"-(10-{2-[(carboxymethyl)(benzyl)amino]-2-oxoethyl}-1,4,7,10-tetra-azacyclododecane-1,4,7-triyl)triacetate; or a hydrate, a solvate, or a salt thereof, or a mixture of same.

11. A compound having a structure selected from the group consisting of:

Gadolinium 2,2',2"-(10-{2-(methyl)[2-(4-nitrophenoxy)-2-oxoethyl]amino]-2-oxoethyl}-1,4,7,10-tetraazacyclododecane-1,4,7-triyl)triacetate;

Gadolinium 2,2',2"-(10-{2-(ethyl)[2-(4-nitrophenoxy)-2-oxoethyl]amino]-2-oxoethyl}-1,4,7,10-tetraazacyclododecane-1,4,7-triyl)triacetate;

Gadolinium 2,2',2"-(10-{2-{(2-methoxyethyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(2-ethoxyethyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(isopropyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(isobutyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(cyclopropyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(cyclopentyl)[2-(4-nitrophenoxy)-2-oxoethyl]}amino]-2-oxoethyl}-1,4,7,10-tetraazacyclododecane-1,4,7-triyl)triacetate;

Gadolinium 2,2',2"-(10-{2-{(phenyl)[2-(4-nitrophenoxy)-2-oxoethyl]}amino]-2-oxoethyl}-1,4,7,10-tetraazacyclododecane-1,4,7-triyl)triacetate; and Gadolinium 2,2',2"-(10-{2-{(benzyl)[2-(4-nitrophenoxy)-2-oxoethyl]}amino]-2-oxoethyl}-1,4,7,10-tetraazacyclododecane-1,4,7-triyl)triacetate; or a hydrate, a solvate, or a salt thereof, or a mixture of same.

\* \* \* \* \*